United States Patent [19]
Diaz-Torres et al.

[11] Patent Number: 6,136,576
[45] Date of Patent: Oct. 24, 2000

[54] METHOD FOR THE RECOMBINANT PRODUCTION OF 1,3-PROPANEDIOL

[75] Inventors: Maria Diaz-Torres, San Mateo; Nigel S Dunn-Coleman, Los Gatos; Matthew W. Chase, Belmont; Donald Trimbur, Redwood City, all of Calif.

[73] Assignee: Genencor International, Inc., Rochester, N.Y.

[21] Appl. No.: 08/969,683

[22] Filed: Nov. 13, 1997

Related U.S. Application Data
[60] Provisional application No. 60/030,601, Nov. 13, 1996.

[51] Int. Cl.$^7$ ....................................................... C12P 7/18
[52] U.S. Cl. .......................... 435/158; 435/232; 530/350; 536/23.2; 536/23.1; 536/23.7
[58] Field of Search .................................... 435/158, 183, 435/189, 232, 320.1, 257.3, 252.33; 536/23.2, 23.1, 23.7; 530/350

[56] References Cited

U.S. PATENT DOCUMENTS

| | | | |
|---|---|---|---|
| 5,633,362 | 5/1997 | Nagarajan et al. | 536/23.1 |
| 5,686,276 | 11/1997 | Laffend et al. | 435/158 |

FOREIGN PATENT DOCUMENTS

| | | |
|---|---|---|
| 0373230 | 2/1993 | European Pat. Off. |
| WO 96/35795 | 11/1996 | Japan . |
| WO 96/35796 | 11/1996 | WIPO . |

OTHER PUBLICATIONS

Willard, B. L. "Investigation of the *Klebsiella pneumoniae* 1,3–prpanediol pathway: Characterization and expression of glycerol dehydrtatase and 1,3–propanediol oxidoreductase" Thesis, University of Wisconsin–Madison, 1994.
Willard, B. L. Sptrembl9 data base, Accession No. Q59474, Nov. 1996.
Willard, B. L. Sptrembl9 data base, Accession No. Q48422, Nov. 1996.
Willard, B. L. Sptrembl9 data base, Accession No. Q48423, Nov. 1996.
Willard, B. L. Sptrembl9 data base, Accession No. Q484242, Nov. 1996.
Albertyn et al., *Mol. Cell. Biol.* 14, 4135–4144, (1994).
Ben–Amotz et al., *Experientia* 38, 49–52, (1982).
Bobik et al., 1992, J. Bacteriol. 174:2253–2266.
Daniel et al., "Purification of 1,3–Propanediol Dehydrogenase Drom Citrobachter Freundii and Cloning, Sequencing, And Overexpression of the Corresponding Gene In *Escherichia coli*," Year????.
Larason et al., *Mol. Microbiol.* 10, 1101, (1993).
Luers et al. 1997, FEMS Microbiology Letters 154:337–345.
McGee et al., 1982, Biochem. Biophys. Res. Comm. 108:547–551.
Norbeck et al., *J. Biol. Chem.* 271, 13875, (1996).
Seyfried et al., "Cloning, Sequencing, and Overexpression of the Genes Encoding Coenzyme $B_{12}$–Dependent Glycerol Dehydratase of *Citrobacter freundii*," *J. Bacteriol.*, V. 178 (19), pp. 5793–5796, Oct. 1996.
Skraly, F.A., 1997, Thesis entitled "Metabolic Engineering of an Improved 1,3–Propanediol Fermentation" pp. 53–84.
Steib et al., *Arch. Microbiol.* 140, 139 (1984).
Tobimatsu et al., "Molecular cloning, sequencing, and expression of the genes encoding adenosylcobalamin—dependent diol dehydrase of *Klebsiella oxytoca*," *J. Biol. Chem.*, V. 270, pp. 7142–7148 1995.
Tobimatsu et al., "Cloning, sequencing and high level expression of the genes encoding adenosylcobalamin—dependent glycerol dehydrase of *Klebsiella pneumoniae*," *J. Biol. Chem.*, V. 271, No. 37, pp. 22352–23357 1996.
Tong et al., *Appl. Biochem. Biotech.* 34, 149 (1992).
Tong, et al., "1,3–propanediol production by *Escherichia coli* expressing genes from the *Klebsiella pneumoniae* dha regulon," *Applied and Environmental Microbiology*, V. 57, pp. 3541–35476 1991.
Veiga DA Cunha et al., *J. Bacteriol.* 174, 1013 (1992).
Wang et al., *J. Bact.* 176, 7091–7095 (1994.

*Primary Examiner*—Nashaat T. Nashed

[57] ABSTRACT

The present invention provides an improved method for the production of 1,3-propanediol from a variety of carbon sources in an organism capable of 1,3-propanediol production and comprising DNA encoding protein X of a microorganismal dehydratase or protein X in combination with at least one of protein 1, protein 2 and protein 3, which proteins are comparable to those encoded by orfY, orfX and orfW, respectively from a microorganismal dha regulon. The protein X may be isolated from a diol dehydratase or a glycerol dehydratase. The present invention also provides host cells comprising protein X that are capable of increased production of 1,3-propanediol.

17 Claims, 27 Drawing Sheets

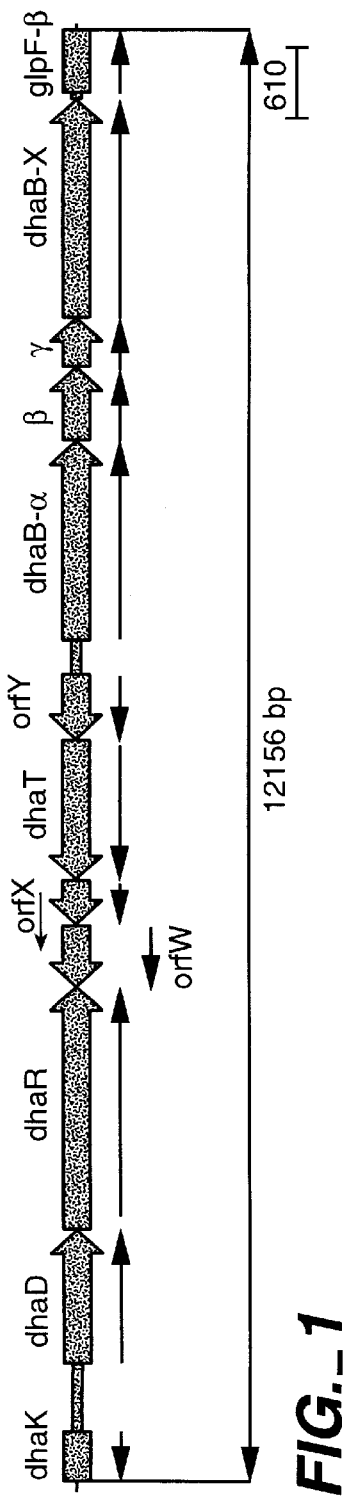

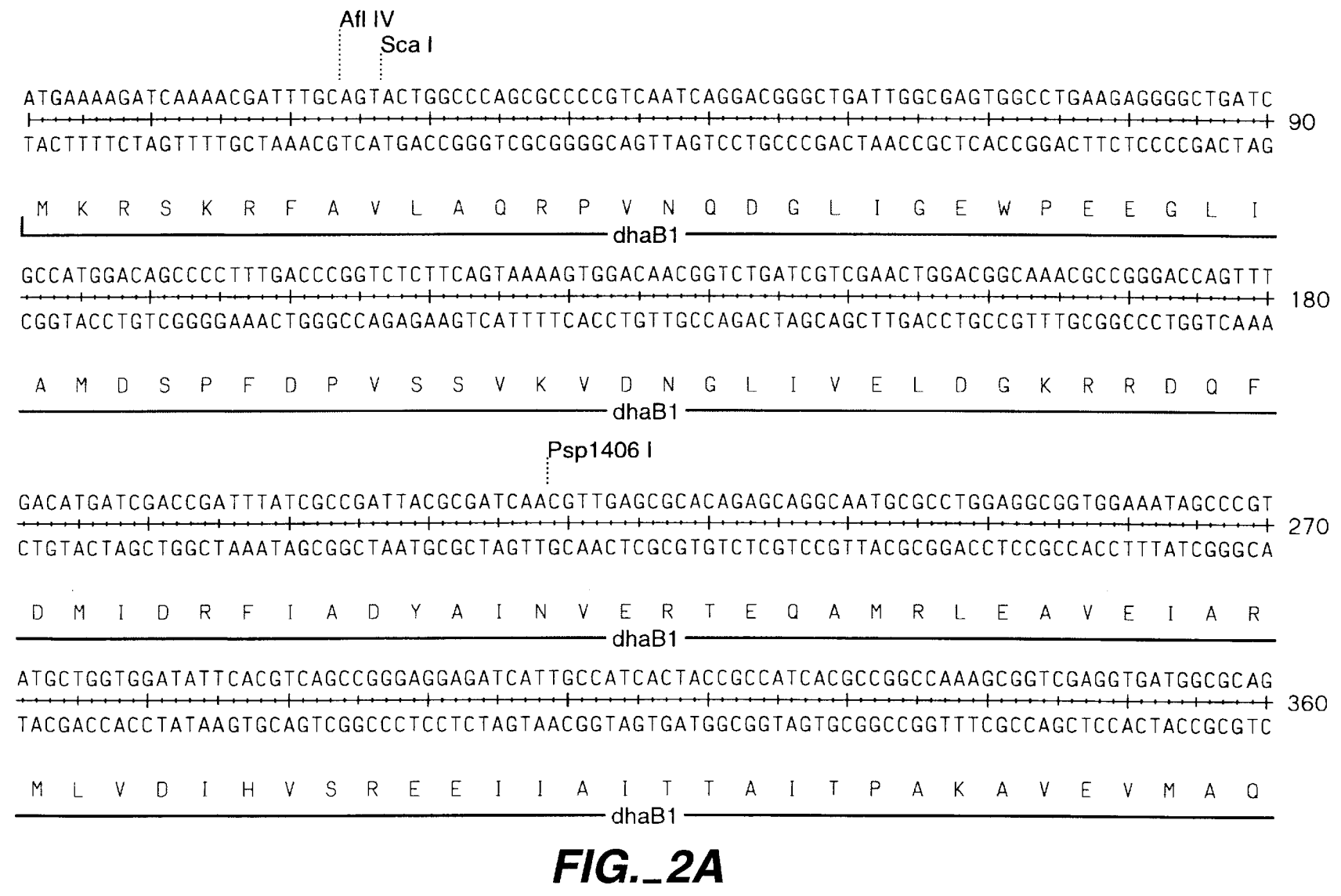

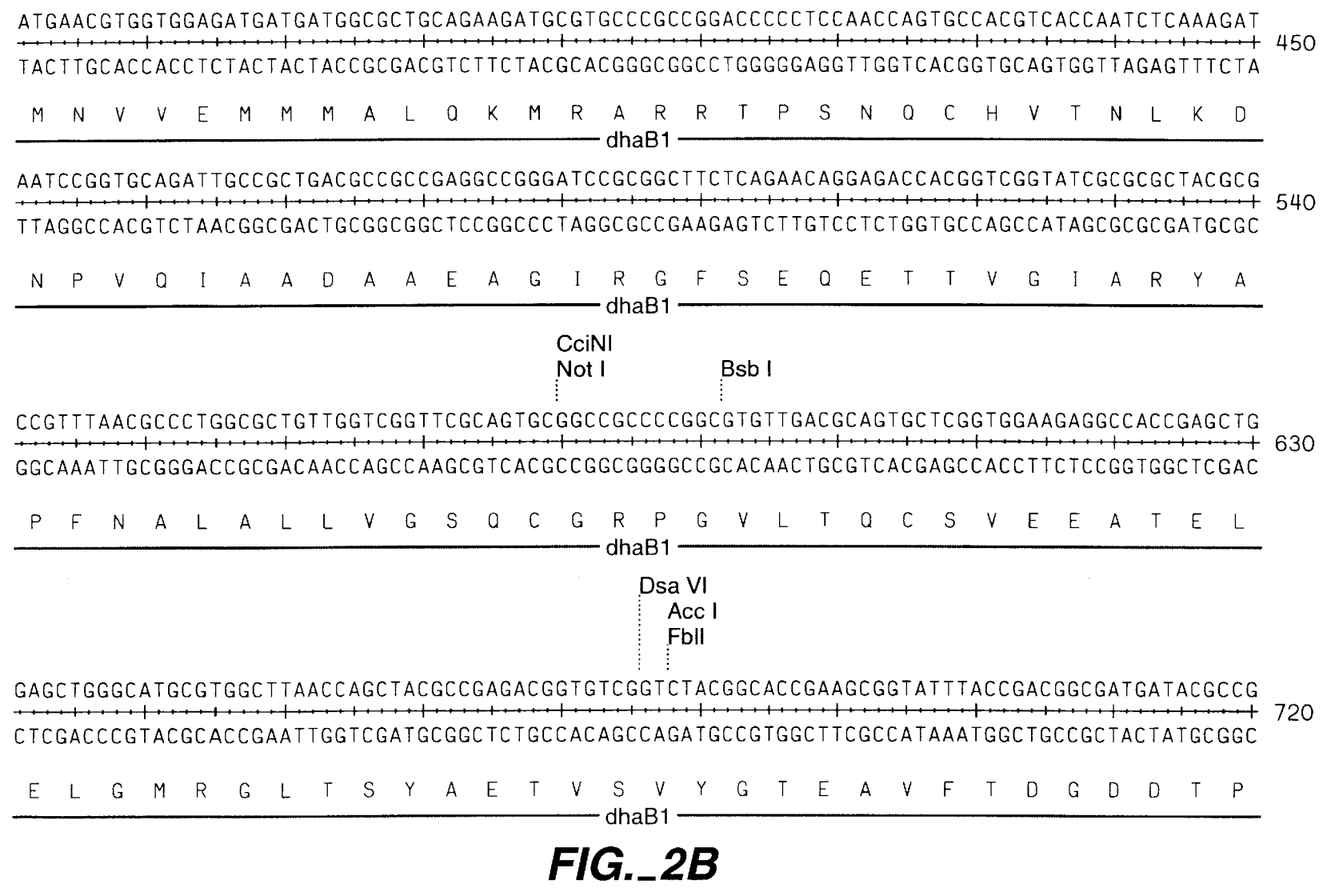

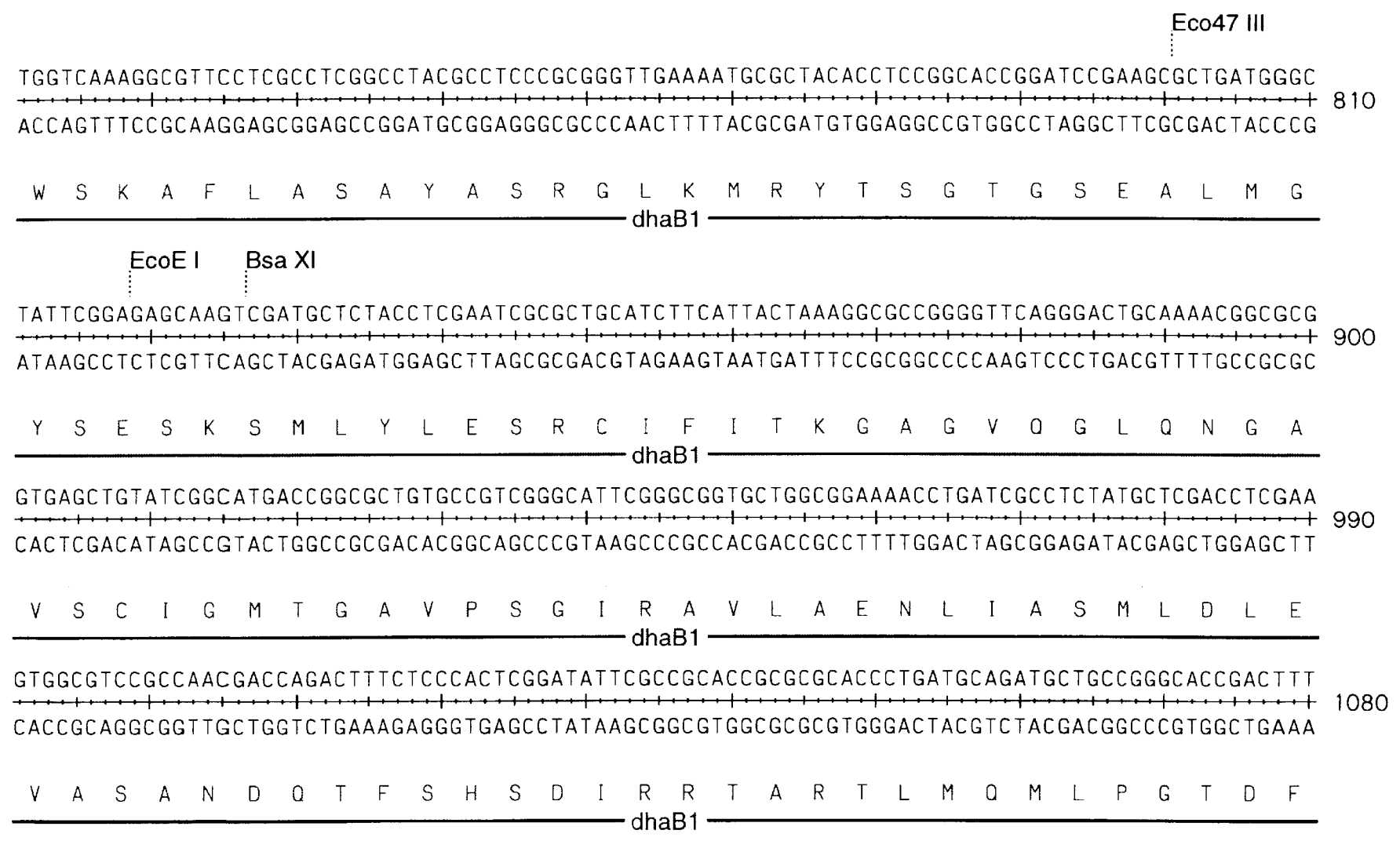

```
                     Pfl1108 I
ATTTCTCCGGCTACAGCGCGGTGCCGAACTACGACAACATGTTCGCGGGCTCGAACTTCGATGCGGAAGATTTTGATGATTACAACATC
                                                                                         ─┼─ 1170
TAAAAGAGGCCGATGTCGCGCCACGGCTTGATGCTGTTGTACAAGCGCCCGAGCTTGAAGCTACGCCTTCTAAAACTACTAATGTTGTAG

I  F  S  G  Y  S  A  V  P  N  Y  D  N  M  F  A  G  S  N  F  D  A  E  D  F  D  D  Y  N  I
                                                      ────────── dhaB1 ──────────

CTGCAGGCGGTGACCTGATGGTTGACGGCGGCCTGCGCCCTGACGGAGGCGGAAACCATTGCCATTCGCCAGAAAGCGGCGGGGCGATC
                                                                                         ─┼─ 1260
GACGTCGCCACTGGACTACCAACTGCCGCCGGACGCGGGACTGCCTCCGCCTTTGGTAACGGTAAGCGGTCTTTCGCCGCCCCGCCTAG

L  Q  R  D  L  M  V  D  G  G  L  R  P  V  T  E  A  E  T  I  A  I  R  Q  K  A  A  R  A  I
              ───────────────────────────────── dhaB1 ─────────────────────────────────

CAGGCGGTTTTCCGCGAGCTGGGGCTGCCGCCAATCGCCGACGAGGAGGTGGAGGCCGCCACCTACGCGCCACCTCCCGGCTGGATGCCG
                                                                                         ─┼─ 1350
GTCCGCCAAAAGGCGCTCGACCCCGACGGCGGTTAGCGGCTGCTCCTCCACCTCCGGCGGTGGATGCGCCGGTGGAGGGCCGACCTACGGC

Q  A  V  F  R  E  L  G  L  P  P  I  A  D  E  E  V  E  A  A  T  Y  A  H  G  S  N  E  M  P
              ───────────────────────────────── dhaB1 ─────────────────────────────────

CCGCGTAACGTGGTGGAGGATCTGAGTGCGGTGGAAGAGATGATGAAGCGCAACATCACCGGCCTCGATATTGTCGGCGAGCCG
                                                                                         ─┼─ 1440
GGCGCATTGCACCACCTCCTAGACTCACGCCACCTTCTCTACTACTTCGCGTTGTAGTGGCCGGAGCTATAACAGCCGCTCGGCG

P  R  N  V  V  E  D  L  S  A  V  E  E  M  M  K  R  N  I  T  G  L  D  I  V  G  A  L  S  R
              ───────────────────────────────── dhaB1 ─────────────────────────────────
```

```
                                                        Uba1220 I
                                                        Cfr9I
                                                        PspAI
                                                        XmaI
                                                            CfrJ4I
                                                             SmaI
                                                        ......
CACCAGCATCACACTCTGATCGATATGCCCCATGGGCGATCCTCAAAGAGCTGATTGCCGGGGTGGAAGAAGAGGGGCTTCACGCCCGG  1890
----+----+----+----+----+----+----+----+----+----+----+----+----+----+----+----+----+----+
GTGGTCGTAGTGTGAGACTAGCTATACGGGGTACCCGCTAGGAGTTTCTCGACTAACGGCCCCACCTTCTTCTCCCGAAGTGCGGGCC

H  Q  H  H  T  L  I  D  M  P  H  G  A  I  L  K  E  L  I  A  G  V  E  E  E  G  L  H  A  R
                                          ───────────────────────────────────────────────────
                                                                  dhaB2

Ppu1253 I
                 Aat II
                 .......
GTGGTGCGGCATTCTGGCGACGTCCGACGTGCTCTCCTTTATGGCCTGGGATGCGGCCAACCTGAGCGGCTCGGGCATCGGCTATCCAG  1980
----+----+----+----+----+----+----+----+----+----+----+----+----+----+----+----+----+----+
CACCACGCGCCGTAAGACCGCTGCAGGCTGCACGAGAGGAAATACCGGACCCTACGCCGGTTGGACTCGCCGAGCCCTAGCCGATAGGTC

V  V  R  I  L  R  T  S  D  V  S  F  M  A  W  D  A  A  N  L  S  G  S  G  I  G  I  G  I  Q
  ─────────────────────────────────────────────────────────────────────────────────────────
                                              dhaB2

TCGAAGGGGACCACGGTCATCCATCAGCGCGATCTGCTGCCCTCAGCAACCTGGAGCTGTTCTCCCAGGCGCCTGCTGACGCTGGAG  2070
----+----+----+----+----+----+----+----+----+----+----+----+----+----+----+----+----+----+
AGCTTCCCCTGGTGCCAGTAGGTAGTCGCGCTAGACGACGGGAGTCGTTGGACCTCGACAAGAGGGTCCGCGGACGACTGCGACCTC

S  K  G  T  T  V  I  H  Q  R  D  L  L  P  L  S  N  L  E  L  F  S  Q  A  P  L  L  T  L  E
  ─────────────────────────────────────────────────────────────────────────────────────────
                                              dhaB2
```

*FIG._2F*

```
ACCTACCGGCAGATTGGCCAAAACGCTGCGCTATGCGCCAAAGAGTCACCTTCGCCGGTGCCGGTGGTGAACGATCAGATGGTCGG
     +         +         +         +         +         +         +         +         + 2160
TGGATGGCCGTCTAACCGGTTTTGCGACGCGATACGCGGTTTCTCAGTGGAAGCGGCCACGGCCACCACTTGCTAGTCTACCAGCC

T  Y  R  Q  I  G  K  N  A  A  R  Y  A  R  K  E  S  P  S  P  V  P  V  V  N  D  Q  M  V  R
                                             ———————————dhaB2

CCGAAATTTATGGCCAAAGCCGCGCTATTTCATATCAAAGAGACCAAACATGTGGTGCAGGACGCCGAGCCCGTCACCCTGCACATCGAC
     +         +         +         +         +         +         +         +         + 2250
GGCTTTAAATACCGGTTTCGGCGCGATAAAGTATAGTTTCTCTGGTTTGTACACCACGTCCTGCGGCTCGGGCAGTGGGACGTGTAGCTG

P  K  F  M  A  K  A  A  L  F  H  I  K  E  T  K  H  V  V  Q  D  A  E  P  V  T  L  H  I  D
                                                                         ———————————dhaB2

TTAGTAAGGGAGTGACCATGAGCGAGAAAACCATGCGCGTGCAGGATTATCCGTTAGCCACCCGCTGCCCGGAGCATATCCTGACGCCTA
     +         +         +         +         +         +         +         +         + 2340
AATCATTCCCTCACTGGTACTCGCTCTTTTGGTACGCGCACGTCCTAATAGGCAATCGGTGGGCGACGGGCCTCGTATAGGACTGCGGAT

M  S  E  K  T  M  R  V  Q  D  Y  P  L  A  T  R  C  P  E  H  I  L  T  P
                                            ———————————dhaB3

L  V  R  E
———————————dhaB2
```

FIG._2G

```
                             EciE I
                             Bsp120 I
                              Apa I
                              Ppe I
CCGGCAAACCATTGACCGATATTACCCTCGAGAAGGTGTCTCTGGCGAGGTGGGCCCGCAGGATGTGCGGATCTCCCGCCAGACCCTTG   2430
+---------+---------+---------+---------+---------+---------+---------+---------+---------+
GGCCGTTTGGTAACTGGCTATAATGGGAGCTCTTCCACGAGAGACCGCTCCACCCGGGCGTCCTACACGCCTAGAGGGCGGTCTGGGAAC

T  G  K  P  L  T  D  I  T  L  E  K  V  L  S  G  E  V  G  P  Q  D  V  R  I  S  R  Q  T  L
 ─────────────────────────────────────────── dhaB3 ────────────────────────────────────────
                      Van91 I AGTACCAGGCGCAGATTGCCGAGCAGATGCAGCGCCATGCGGTGGCGCGGAGCAATTTCCGCCGCGGGAGCTTATGCCATTCCTGACG    2520
+---------+---------+---------+---------+---------+---------+---------+---------+---------+
TCATGGTCCGCGTCTAACGGCTCGTCTACGTCGCGGTACGCCACCGCGCCTCGTTAAAGGCGGCGCCCTCGAATAGCGGTAAGGACTGC E  Y  Q  A  Q  I  A  E  Q  M  Q  R  H  A  V  A  R  N  F  R  R  A  A  E  L  I  A  I  P  D
 ─────────────────────────────────────────── dhaB3 ────────────────────────────────────────
                                                                       Sgf I AGGCGCATTCTGGCTATCTATAACGCGCTGCGCCCGTTCCGCTCCTCGCAGGAGCTGCTGGCCATCGCCGACGAGCTGGAGCACACCT    2610
+---------+---------+---------+---------+---------+---------+---------+---------+---------+
TCGCGTAAGACCGATAGATATTGCGCGACGCGGGCAAGGCGAGGAGCGTCCTCGACGACCGGTAGCGGCTGCTCGACCTCGTGTGGA E  R  I  L  A  I  Y  N  A  L  R  P  F  R  S  S  Q  A  E  L  L  A  I  A  D  E  L  E  H  T
 ─────────────────────────────────────────── dhaB3 ────────────────────────────────────────
```

```
AGACCATTATCACCGAATCGACCATGATCGGTCATAAACCCGCAGACGCCGGGCGGGGTTGGCGTGGGGACGACTATCGCCCTCG
----+----+----+----+----+----+----+----+----+----+----+----+----+----+----+----+----+    3060
TCTGGTAATAGTGGCTTAGCTGGTACTAGCCAGTATTGGGCGTCTGCGGCCCCGCCACCCGCAACCGCACCCCTGCTGATAGCGGGAGC

E  T  I  I  T  E  S  T  M  I  G  H  N  P  Q  T  P  G  G  V  G  V  G  T  T  I  A  L
                                                └──── dhaB4 ────                              Drd I GGCGGCTGGCCGACGCTGCCGGCGGCGCAGTATGCCGAGGGGTGGATCGTACTGATTGACGACGCCGTCGATTTCCTTGACGCCGTGTGGT
----+----+----+----+----+----+----+----+----+----+----+----+----+----+----+----+----+    3150
CCGCCGACCGGCTGCGACGGCCGCCGCGTCATACGGCTCCCCACCTAGCATGACTAACTGCTGCGGCAGCTAAAGGAACTGCGGCACACCA G  R  L  A  T  L  P  A  A  Q  Y  A  E  G  W  I  V  L  I  D  D  A  V  D  F  L  D  A  V  W
                                          └──── dhaB4 ────

GGCTCAATGAGGCGCTCGACCGGGGAATCAACGTGGTGGCGGCGATCCTCAAAAAGGACGACGGCGTGCTGGTGAACAACCGCCTGCGTA
----+----+----+----+----+----+----+----+----+----+----+----+----+----+----+----+----+    3240
CCGAGTTACTCCGCGAGCTGGCCCCTTAGTTGCACCACCGCCGCTAGGAGTTTTTCCTGCTGCCGCACGACCACTTGTTGGCGGACGCAT
      └ EcoB I
 W  L  N  E  A  L  D  R  G  I  N  V  V  A  A  I  L  K  K  D  D  G  V  L  V  N  N  R  L  R
                                          └──── dhaB4 ────

AAACCCTGCCGGTGGTGGATGAAGTGACGCTGCTGGAGCAGGTTCCCGAGGGGGTAATGGCGGCGGTGGAAGTGGCCGCGGGCCCAGG
----+----+----+----+----+----+----+----+----+----+----+----+----+----+----+----+----+    3330
TTTGGGACGGCCACCACCTACTTCACTGCGACGACCTCGTCCAAGGGCTCCCCCATTACCGCCGCCACCTTCACCGGCGCCCGGGTCC

K  T  L  P  V  V  D  E  V  T  L  L  E  Q  V  P  E  G  V  M  A  A  V  E  V  A  A  P  G  Q
                                          └──── dhaB4 ────
```

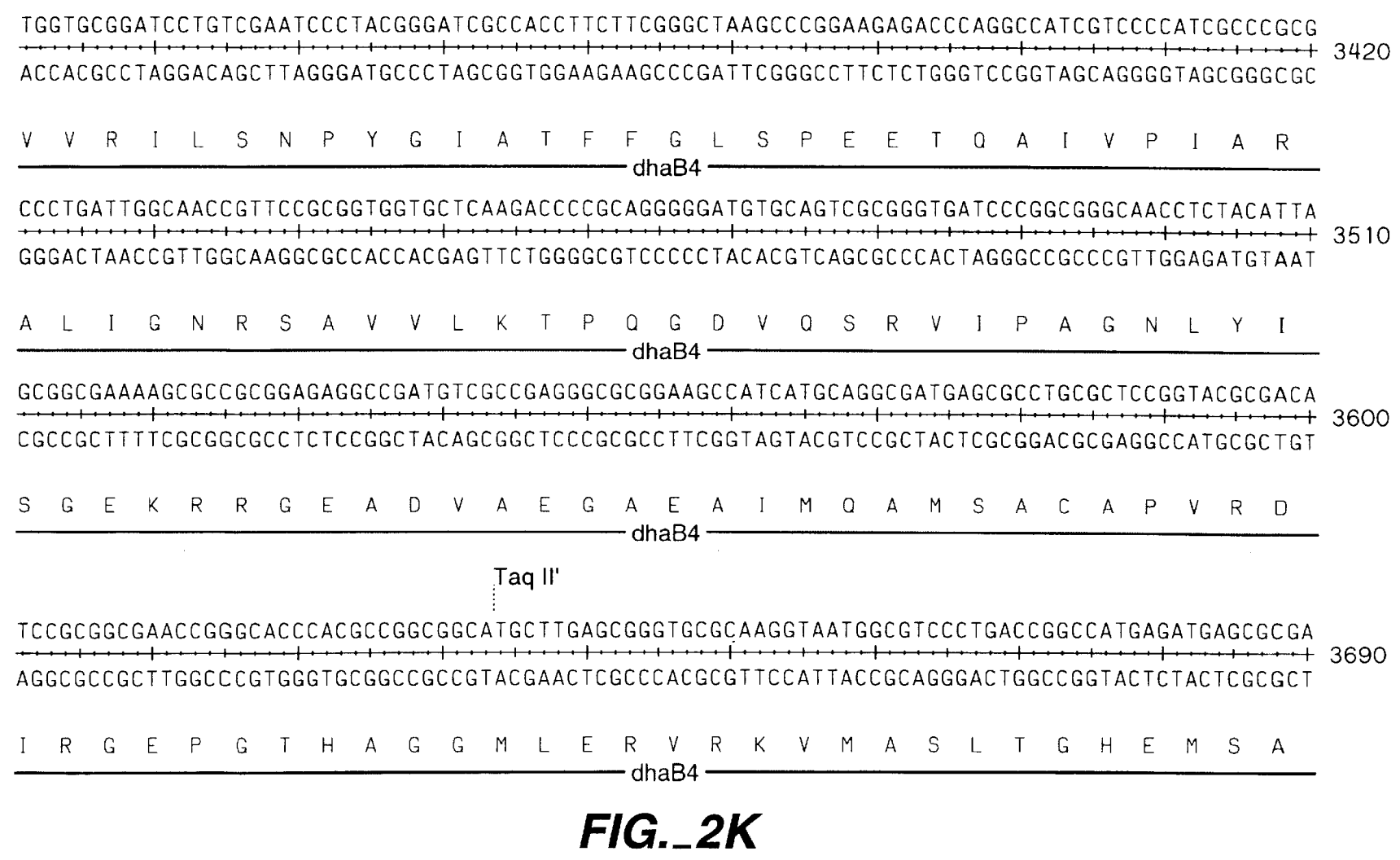

```
TATACATCCAGGATCTGCTGGCGGTGGATACGTTTATTCCGCGCAAGGTGCAGGGCGGGATGGCCGGCGAGTGCGCCATGGAGAATGCCG
                                                                                          3780
ATATGTAGGTCCTAGACGACGCCACCTACCTATGCAAATAAGGCGCGTTCCACGTCCCGCCCTCACGCCGGTACCTCTTACGGC
   I   Y   I   Q   D   L   L   A   V   D   T   F   I   P   R   K   V   Q   G   G   M   A   G   E   C   A   M   E   N   A
                                                                       ─────dhaB4

TCGGGGATGGCGGGCGGCGATGGTGAAAGCGGATCGTCTGCAAATGCAGGTTATCGCCCGCGAACTGAGCGCGAGACTGAGGTGGTGG
                                                                                          3870
AGCCCTACCGCCCGCCGCTACCACTTTCGCCTAGCAGACGTTTACGTCCAATAGCGGGCGCTTGACTCGCGCTCTGACTCCACCACC
   V   G   M   A   A   M   V   K   A   D   R   L   Q   M   Q   V   I   A   R   E   L   S   A   R   L   Q   T   E   V   V
                                                   ───────────────dhaB4

SdiI            BsaKI
                                          SfiI            BstHPI
                                                          HpaI
                                          ....            ....
TGGGCGGGCGTGGAGGCCAACATGGCCATCGCCGGGGCGCTGACCACTCCCGGGTGTTAACCACTCCCGGATCCTCTTGACCTCGGCCG
                                                                                          3960
ACCCGCCCGCACCTCCGGTTGTACCGGTAGCGGCCCCGCGACTGGTGAGGGCCCCACAATTGGTGAGGGCCTAGGAGACTGGAGCCGGC
   V   G   G   V   E   A   N   M   A   I   A   G   A   L   T   T   P   G   C   A   A   P   L   A   I   L   D   L   G   A
                                                   ───────────────dhaB4

GCTCGACGGATGCGGCGATCGTCAACGCGGAGGGCCAGATAACGGGCGGTCCATCTCGCCGGGAATATGGTCAGCCTGTTGATTA
                                                                                          4050
CGAGCTGCCTACGCCGCTAGCAGTTGCGCCTCCCGGTCTATTGCCCGCCAGGTAGAGCGGCCCTTATACCAGTCGGACAACTAAT
   G   S   T   D   A   A   I   V   N   A   E   G   Q   I   T   A   V   H   L   A   G   A   G   N   M   V   S   L   L   I
                                                   ───────────────dhaB4
```

*FIG._2L*

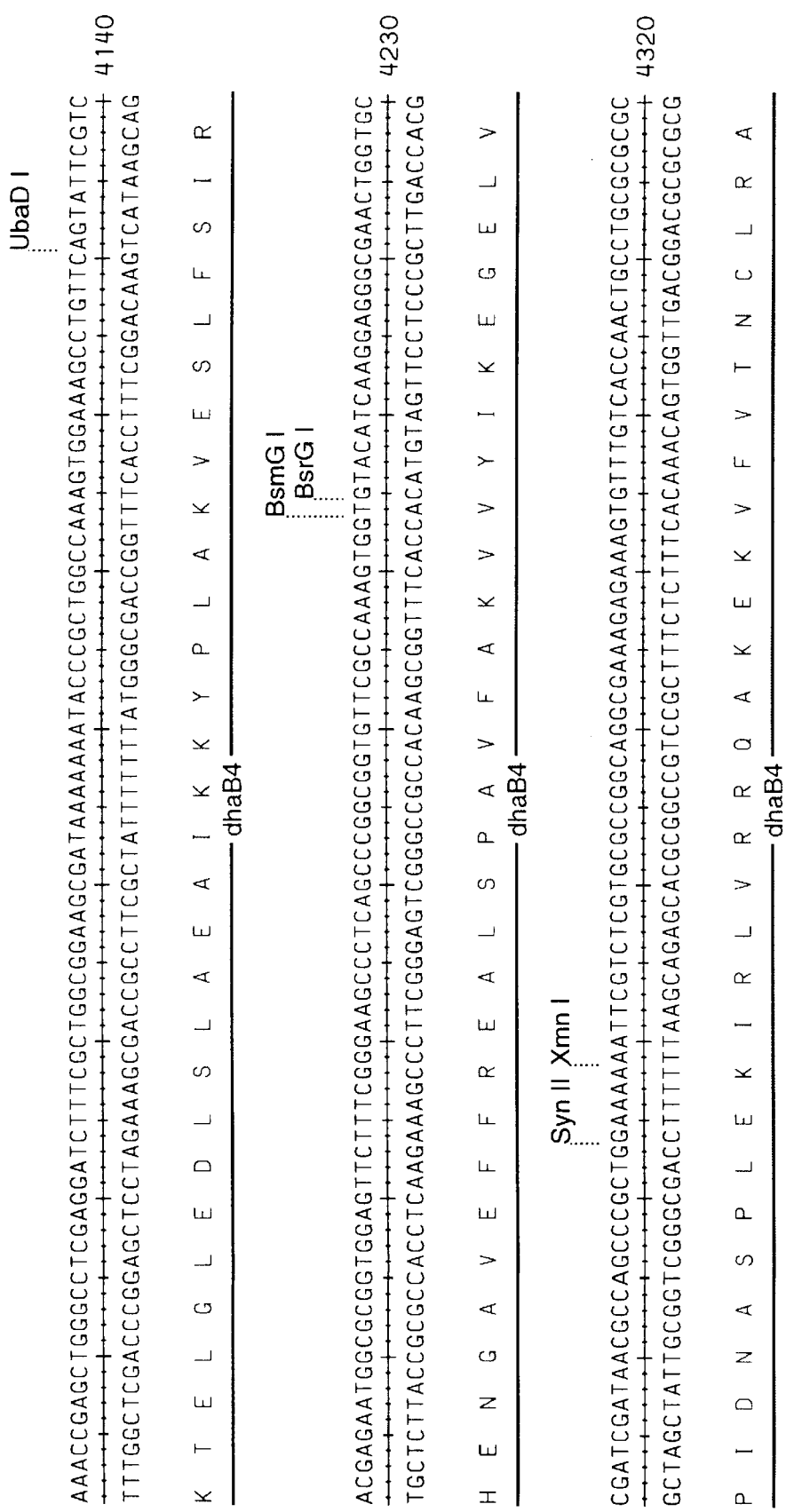
FIG._2M

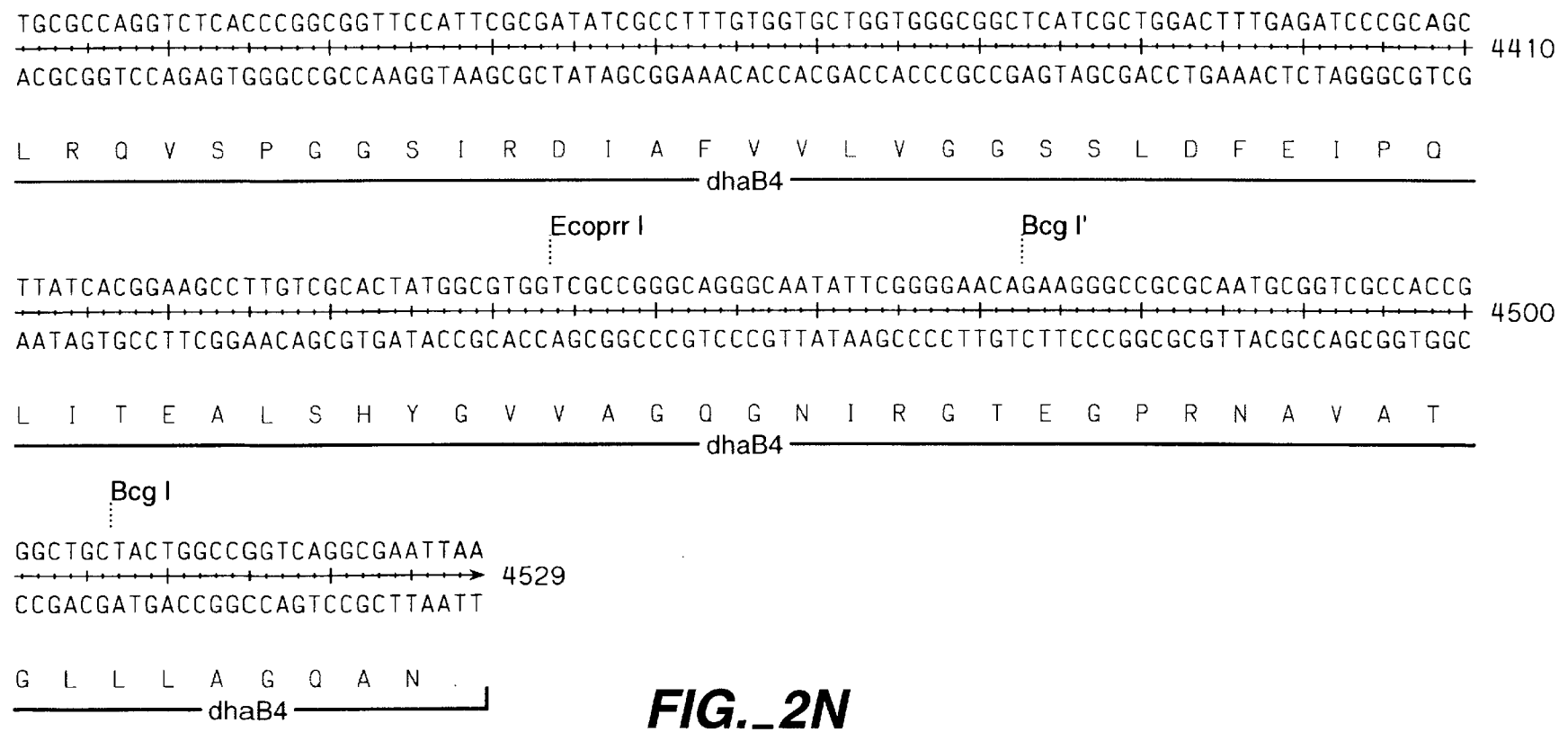

FIG._2N

```
            M M N K S Q Q V A T I T L A A A Q Q M A A A V E A K A K A L E I N V A V V F S V V D   Majority
                      10                  20                  30                  40

1    M - N K S Q Q I A T I T L A A A K K M A Q A V E A K A L E I N V P V V F S V V D   cfu_orfY.aa
  1    M M N K S Q Q V Q T I T L A A A A Q Q M A A A V E K K A T E I N V A V V F S V V D   Kpn_orfY.aa H G G N T L L I Q R M D D A F V S S C D I S L N K A Y S A C S L K Q G T H E I T   Majority
                      50                  60                  70                  80

40    H G G N T L L M Q R M D D A F V T S C D I S L N K A Y T A C C L R Q G T H E I T   cfu_orfY.aa
 41    R G G N T L L I Q R M D E A F V S S C D I S L N K A W S A C S L K Q G T H E I T   Kpn_orfY.aa S A V Q P G A S L Y G L Q L T N Q Q R I V I F G G G L P V I L N G Q V I G A V G   Majority
                      90                  100                 110                 120

80    D A V Q P G A S L Y G L Q L T N Q Q R I V I F G G G L P V I L N G K V I G A V G   cfu_orfY.aa
 81    S A V Q P G Q S L Y G L Q L T N Q Q R I I I F G G G L P V I F N E Q V I G A V G   Kpn_orfY.aa V S G G T V E Q D Q L L A E T A L D C F S A L   Majority
                      130                 140

120    V S G G T V E Q D R L L A E T A L D C F S E L   cfu_orfY.aa
121    V S G G T V E Q D Q L L A Q C A L D C F S A L   Kpn_orfY.aa
```

FIG._3

```
        M Y R I Y T R T G D N G T T A L F G G S R I D K D D I R V E A Y G T V D E L I S   Majority
                          10                  20                  30            40
  1     M Y R I Y T R T G D N G T T A L F G G S R I D K D D I R V E A Y G T V D E L I S   cfu_orfW.aa
  1     M Y R I Y T R T G D K G T T A L Y G G S R I E K D H I R V E A Y G T V D E L I S   kpn_orfW.aa Q L G V C Y A S T R D A G L R E S L H A I Q Q T L F V L G A E L A S D A K G L T   Majority
                          50                  60                  70            80
 41     Q L G V C Y A S T R Q A E L R Q E L H A M Q K M L F V L G A E L A S D Q K G L T   cfu_orfW.aa
 41     Q L G V C Y A T T R D A G L R E S L H H I Q Q T L F V L G A E L A S D A R G L T   kpn_orfW.aa R L S Q T I G E E D I T A L E Q L I D R N M A E S G P L K E F V I P G K N L A S   Majority
                          90                  100                 110           120
 81     R L K Q R I G E E D I Q A L E Q L I D R N M A Q S G P L K E F V I P G K N L A S   cfu_orfW.aa
 81     R L S Q T I G E E E I T A L E R L I D R N M A E S G P L K Q F V I P G R N L A S   kpn_orfW.aa A Q L H V A R T L S R R L E R L L I A M G R A L T L R D A A K R Y I N R L S D A   Majority
                          130                 140                 150           160
121     A Q L H V A R T L T R R L E R I L I A M G R T L T L R D E A R R Y I N R L S D A   cfu_orfW.aa
121     A Q L H V A R T Q S R R L E R L L T A M D R A H P L R D A L K R Y S N R L S D A   kpn_orfW.aa L F S M A R I E E T T P D A C A -                                                 Majority
                          170
161     L F S M A R I E E T T P D V C A                                                   cfu_orfW.aa
161     L F S M A R I E E T R P D A C A .                                                 kpn_orfW.aa
```

*FIG. 5*

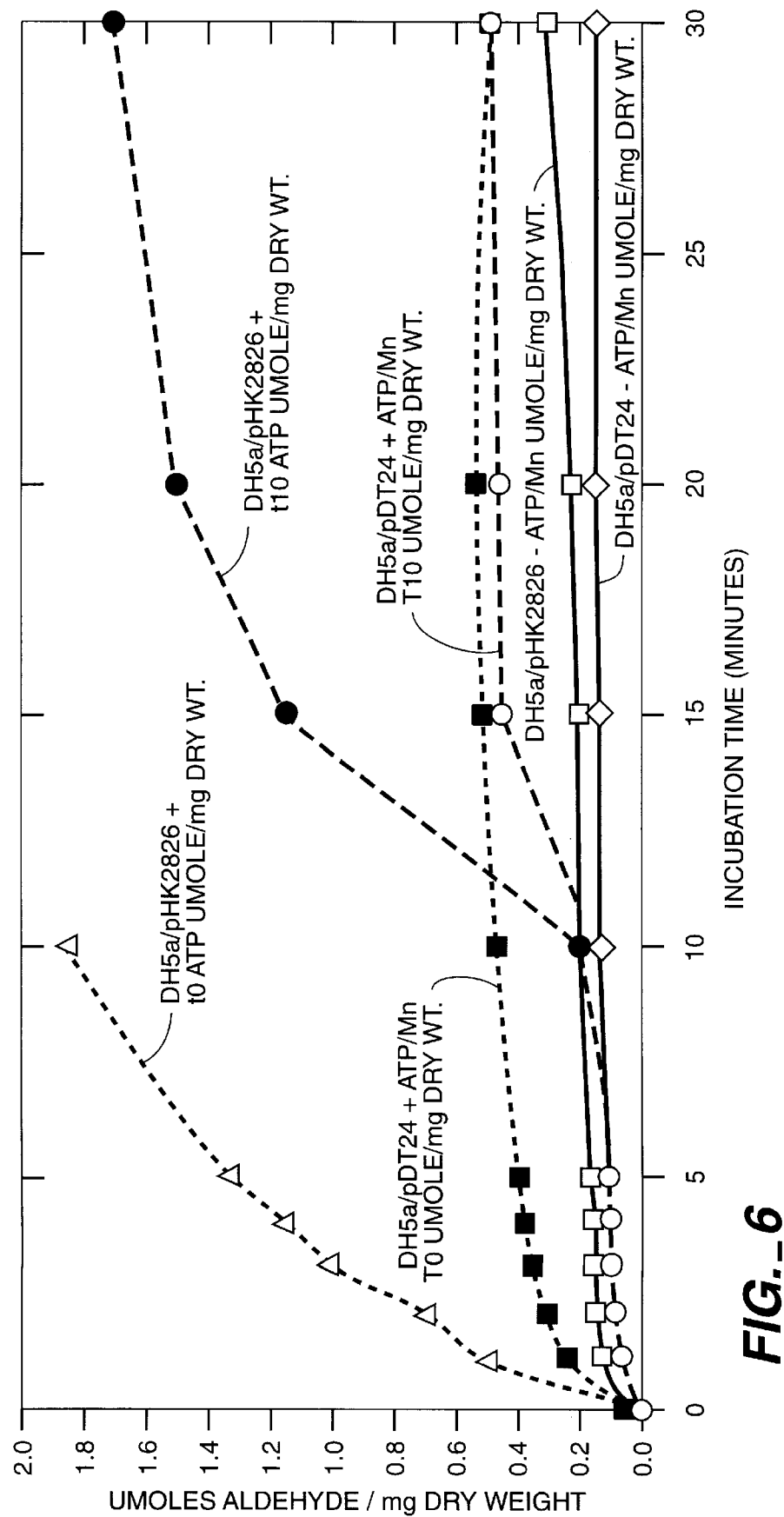
FIG._6

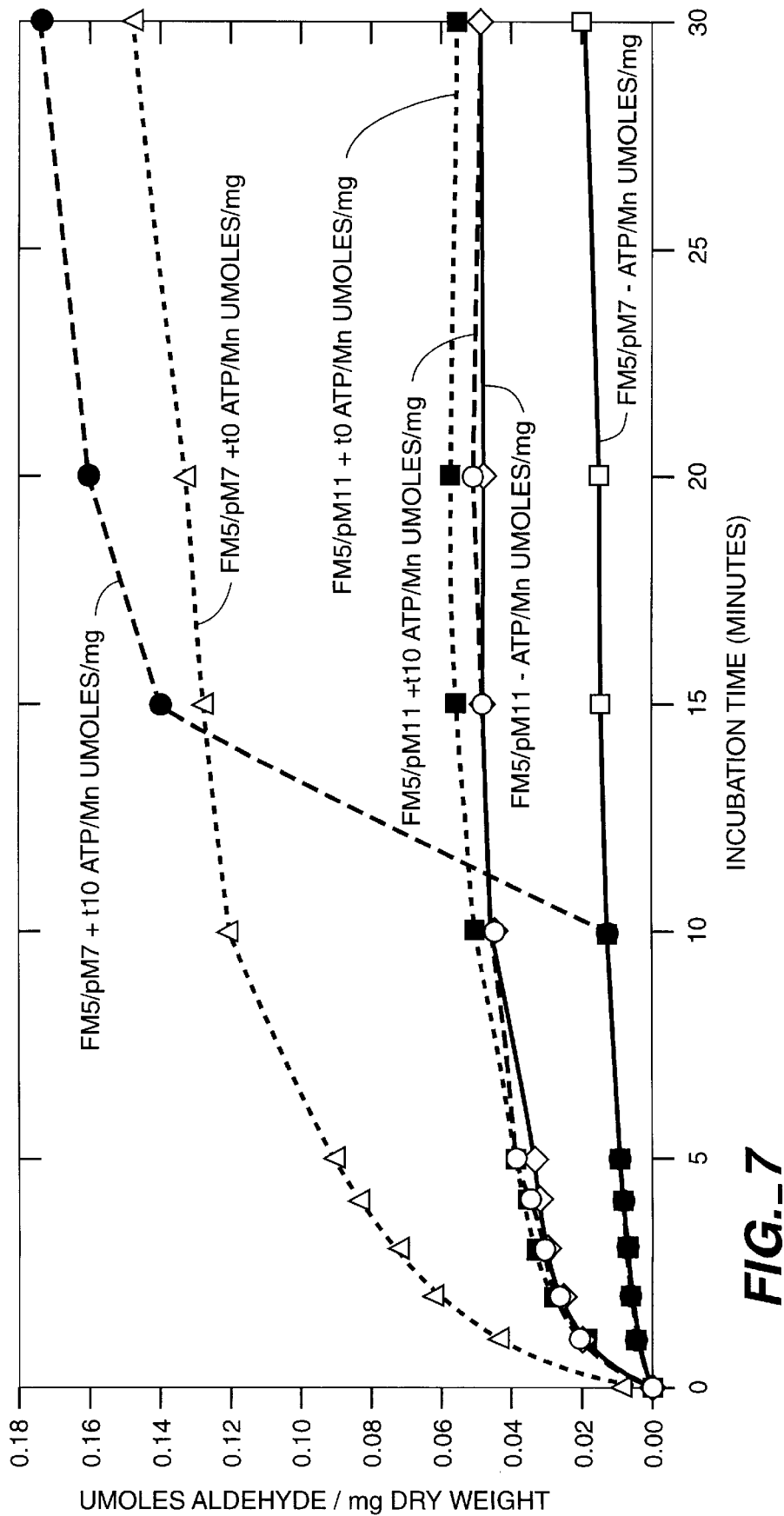
FIG._7

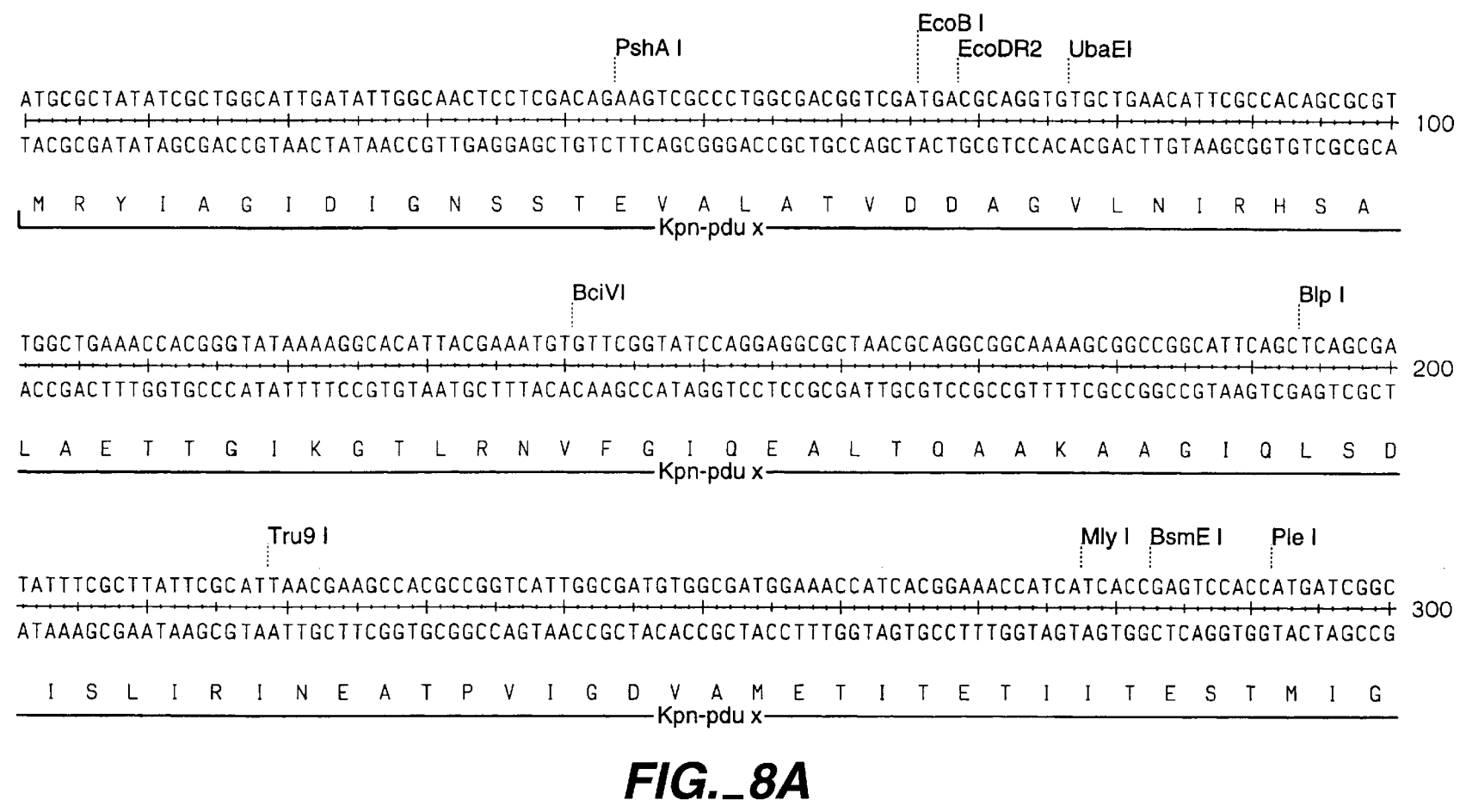

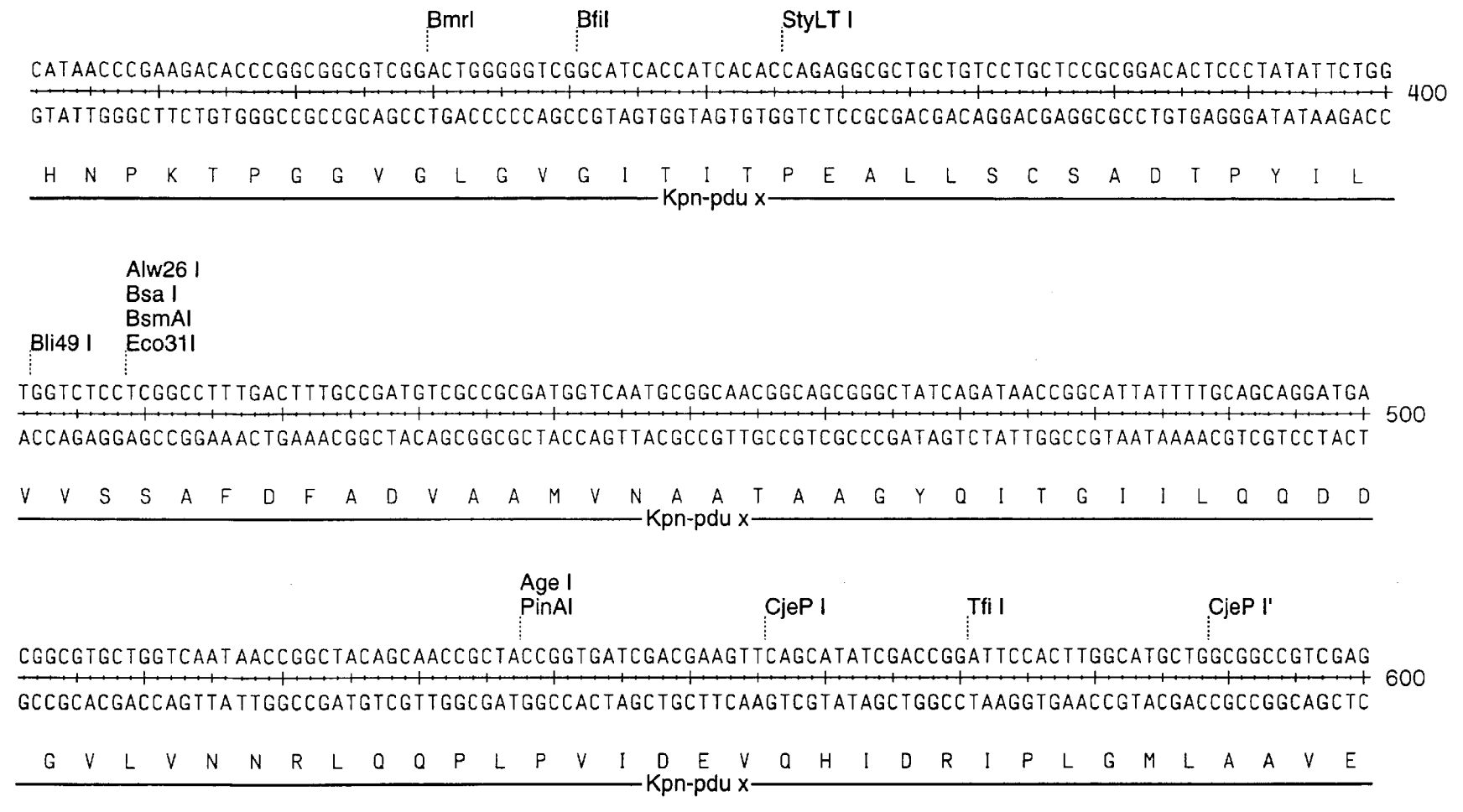

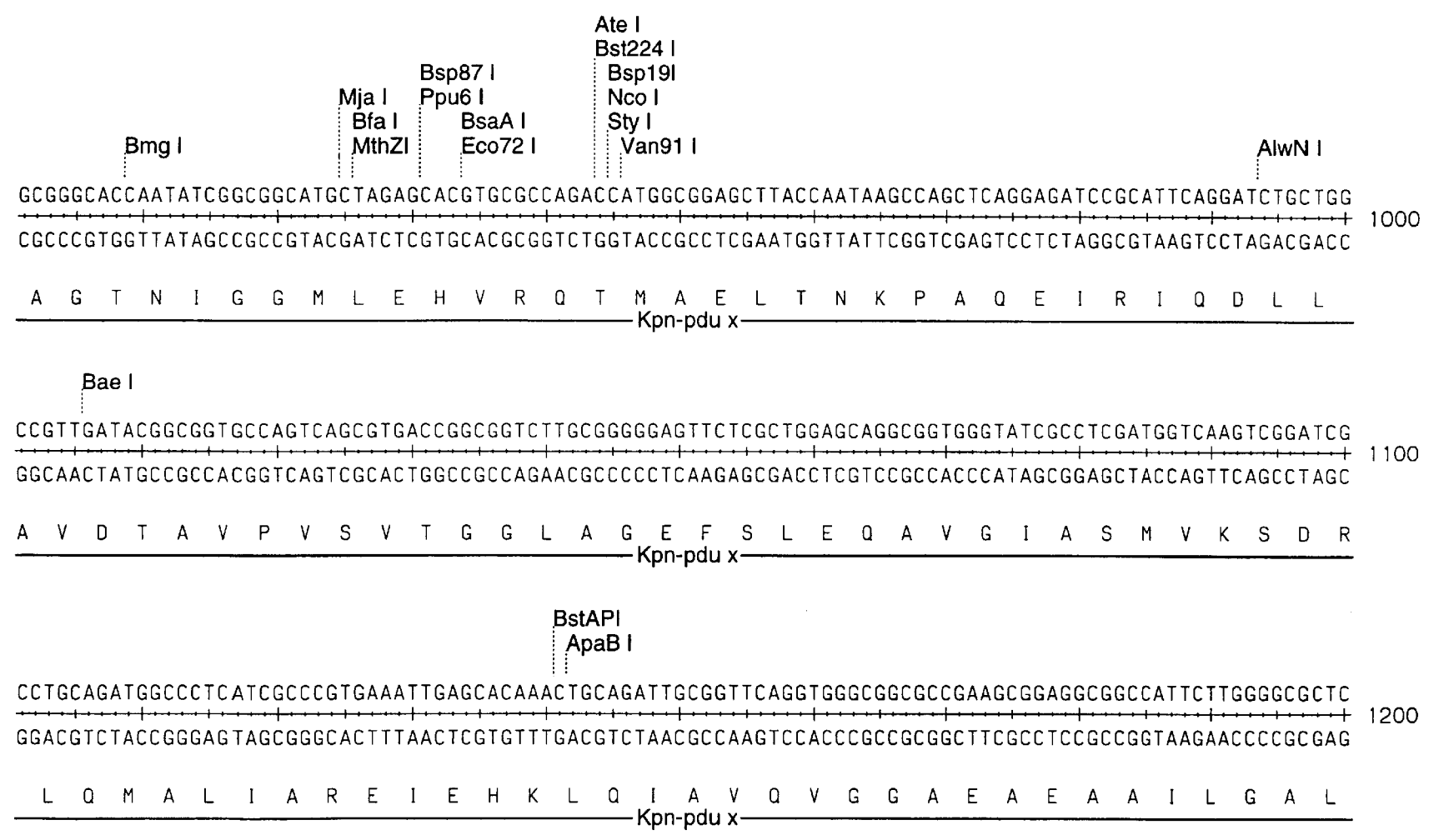

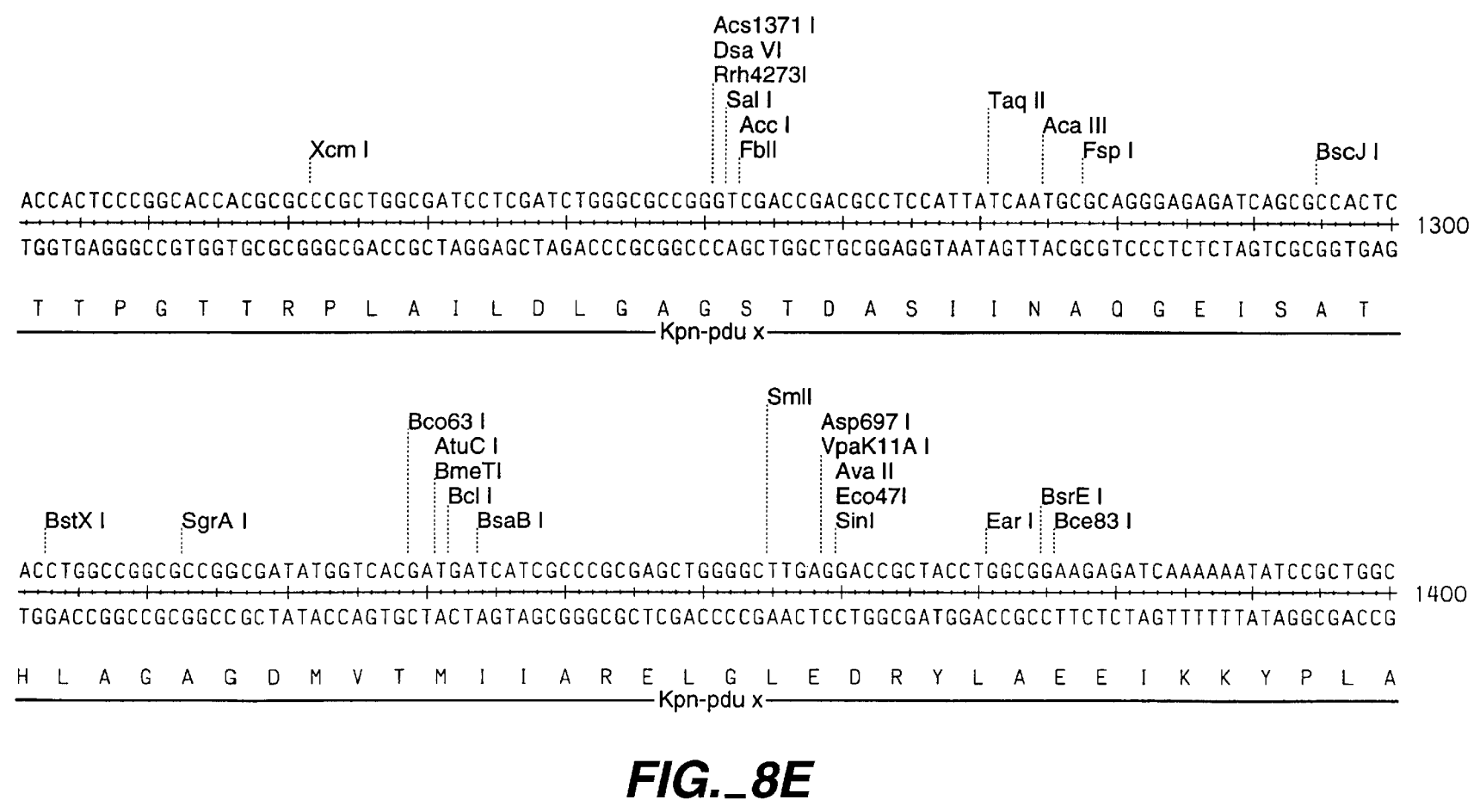

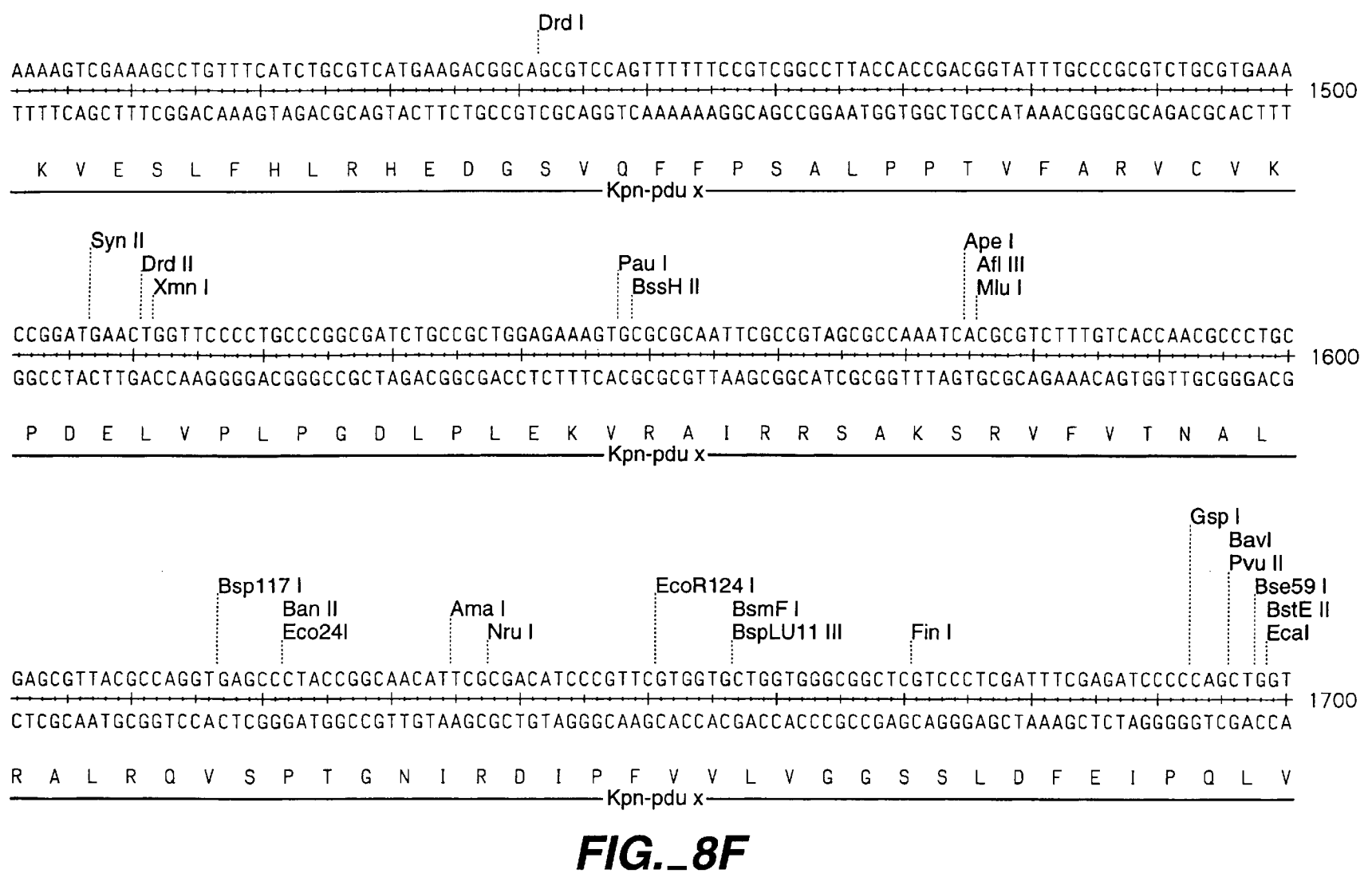

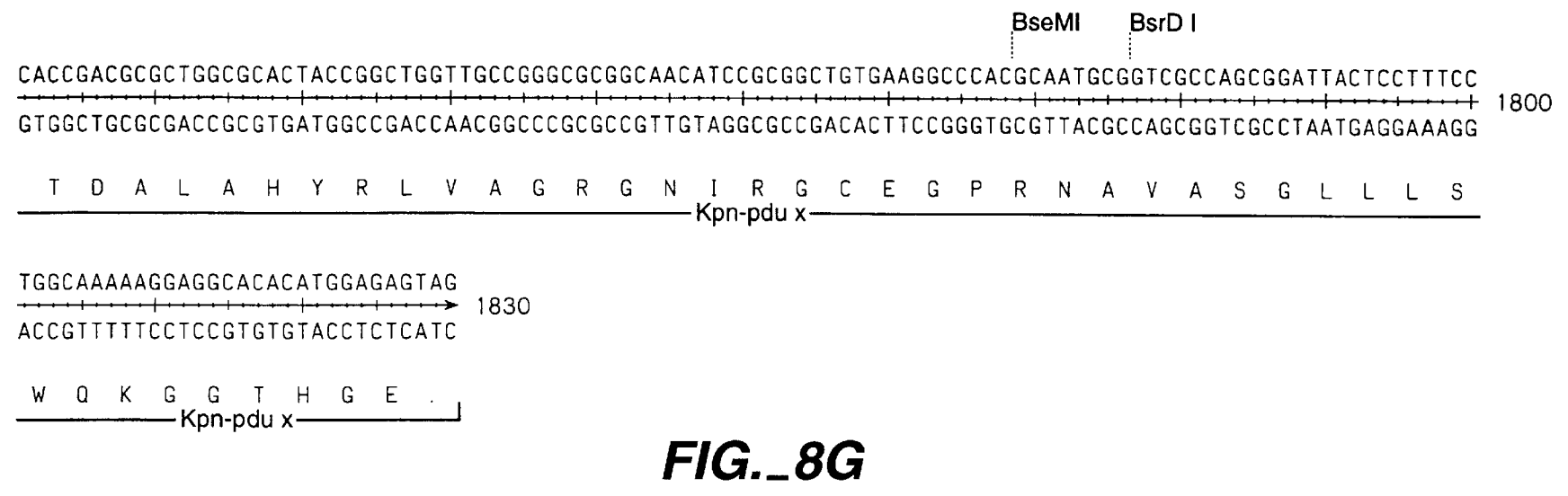

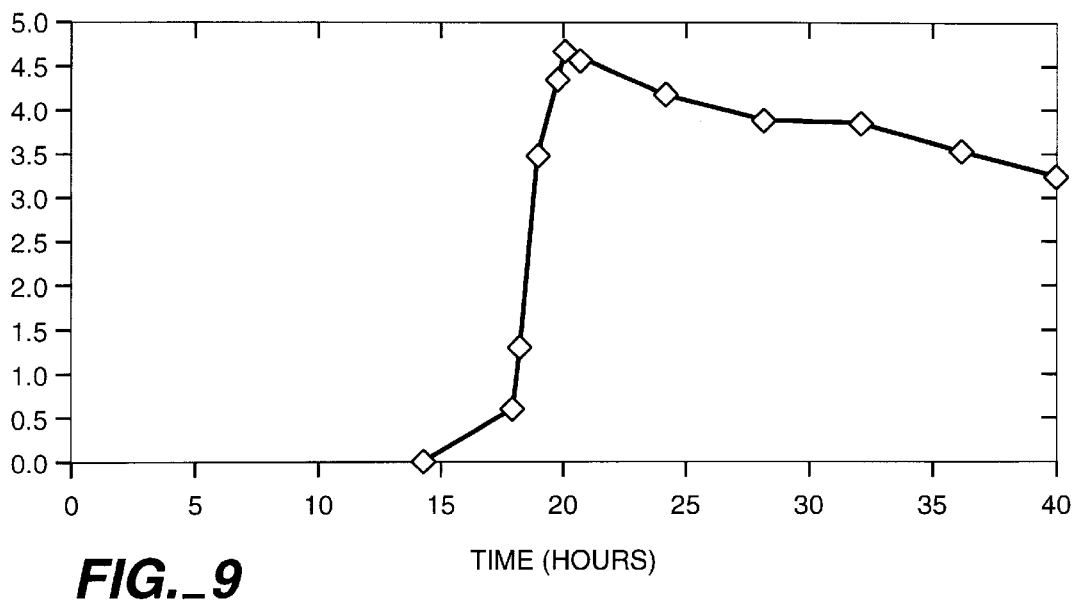
FIG._9  TIME (HOURS)
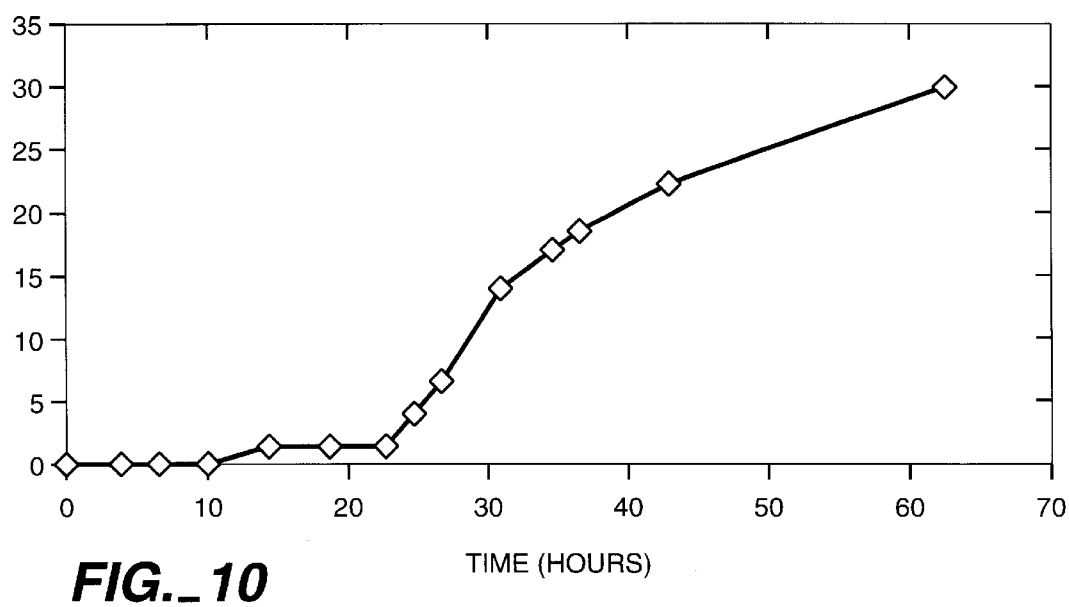
FIG._10  TIME (HOURS)

SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
      (A) LENGTH:  1668 base pairs
      (B) TYPE:  nucleic acid
      (C) STRANDEDNESS:  single
      (D) TOPOLOGY:  linear (ii) MOLECULE TYPE:  DNA (genomic)

(iii) HYPOTHETICAL:  NO (iv) ANTI-SENSE:  NO (vi) ORIGINAL SOURCE:
            (A) ORGANISM: DHAB1

(xi) SEQUENCE DESCRIPTION: SEQ ID NO:1:

ATGAAAAGAT CAAAACGATT TGCAGTACTG GCCCAGCGCC CCGTCAATCA GGACGGGCTG      60

ATTGGCGAGT GGCCTGAAGA GGGGCTGATC GCCATGGACA GCCCCTTTGA CCCGGTCTCT     120

TCAGTAAAAG TGGACAACGG TCTGATCGTC GAACTGGACG GCAAACGCCG GGACCAGTTT     180

GACATGATCG ACCGATTTAT CGCCGATTAC GCGATCAACG TTGAGCGCAC AGAGCAGGCA     240

ATGCGCCTGG AGGCGGTGGA AATAGCCCGT ATGCTGGTGG ATATTCACGT CAGCCGGGAG     300

GAGATCATTG CCATCACTAC CGCCATCACG CCGGCCAAAG CGGTCGAGGT GATGGCGCAG     360

ATGAACGTGG TGGAGATGAT GATGGCGCTG CAGAAGATGC GTGCCCGCCG GACCCCCTCC     420

AACCAGTGCC ACGTCACCAA TCTCAAAGAT AATCCGGTGC AGATTGCCGC TGACGCCGCC     480

GAGGCCGGGA TCCGCGGCTT CTCAGAACAG GAGACCACGG TCGGTATCGC GCGCTACGCG     540

CCGTTTAACG CCCTGGCGCT GTTGGTCGGT TCGCAGTGCG GCCGCCCCGG CGTGTTGACG     600

CAGTGCTCGG TGGAAGAGGC CACCGAGCTG GAGCTGGGCA TGCGTGGCTT AACCAGCTAC     660

GCCGAGACGG TGTCGGTCTA CGGCACCGAA GCGGTATTTA CCGACGGCGA TGATACGCCG     720

TGGTCAAAGG CGTTCCTCGC CTCGGCCTAC GCCTCCCGCG GGTTGAAAAT GCGCTACACC     780

TCCGGCACCG GATCCGAAGC GCTGATGGGC TATTCGGAGA GCAAGTCGAT GCTCTACCTC     840

GAATCGCGCT GCATCTTCAT TACTAAAGGC GCCGGGGTTC AGGGACTGCA AAACGGCGCG     900

GTGAGCTGTA TCGGCATGAC CGGCGCTGTG CCGTCGGGCA TTCGGGCGGT GCTGGCGGAA     960

AACCTGATCG CCTCTATGCT CGACCTCGAA GTGGCGTCCG CCAACGACCA GACTTTCTCC    1020

CACTCGGATA TTCGCCGCAC CGCGCGCACC CTGATGCAGA TGCTGCCGGG CACCGACTTT    1080

ATTTTCTCCG GCTACAGCGC GGTGCCGAAC TACGACAACA TGTTCGCCGG CTCGAACTTC    1140

GATGCGGAAG ATTTTGATGA TTACAACATC CTGCAGCGTG ACCTGATGGT TGACGGCGGC    1200

CTGCGTCCGG TGACCGAGGC GGAAACCATT GCCATTCGCC AGAAAGCGGC GCGGGCGATC    1260

CAGGCGGTTT TCCGCGAGCT GGGGCTGCCG CCAATCGCCG ACGAGGAGGT GGAGGCCGCC    1320

ACCTACGCGC ACGGCAGCAA CGAGATGCCG CCGCGTAACG TGGTGGAGGA TCTGAGTGCG    1380

GTGGAAGAGA TGATGAAGCG CAACATCACC GGCCTCGATA TTGTCGGCGC GCTGAGCCGC    1440

AGCGGCTTTG AGGATATCGC CAGCAATATT CTCAATATGC TGCGCCAGCG GGTCACCGGC    1500

GATTACCTGC AGACCTCGGC CATTCTCGAT CGGCAGTTCG AGGTGGTGAG TGCGGTCAAC    1560

GACATCAATG ACTATCAGGG GCCGGGCACC GGCTATCGCA TCTCTGCCGA ACGCTGGGCG    1620

GAGATCAAAA ATATTCCGGG CGTGGTTCAG CCCGACACCA TTGAATAA                 1668

(2) INFORMATION FOR SEQ ID NO:2:

(i) SEQUENCE CHARACTERISTICS:
         (A) LENGTH: 585 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: DHAB2

(xi) SEQUENCE DESCRIPTION: SEQ ID NO:2:

GTGCAACAGA CAACCCAAAT TCAGCCCTCT TTTACCCTGA AACCCGCGA GGGCGGGTA       60

```
GCTTCTGCCG ATGAACGCGC CGATGAAGTG GTGATCGGCG TCGGCCCTGC CTTCGATAAA      120

CACCAGCATC ACACTCTGAT CGATATGCCC CATGGCGCGA TCCTCAAAGA GCTGATTGCC      180

GGGGTGGAAG AAGAGGGGCT TCACGCCCGG GTGGTGCGCA TTCTGCGCAC GTCCGACGTC      240

TCCTTTATGG CCTGGGATGC GGCCAACCTG AGCGGCTCGG GGATCGGCAT CGGTATCCAG      300

TCGAAGGGGA CCACGGTCAT CCATCAGCGC GATCTGCTGC CGCTCAGCAA CCTGGAGCTG      360

TTCTCCCAGG CGCCGCTGCT GACGCTGGAG ACCTACCGGC AGATTGGCAA AAACGCTGCG      420

CGCTATGCGC GCAAAGAGTC ACCTTCGCCG GTGCCGGTGG TGAACGATCA GATGGTGCGG      480

CCGAAATTTA TGGCCAAAGC CGCGCTATTT CATATCAAAG AGACCAAACA TGTGGTGCAG      540

GACGCCGAGC CCGTCACCCT GCACATCGAC TTAGTAAGGG AGTGA                     585

(2) INFORMATION FOR SEQ ID NO:3:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: DHAB3

(xi) SEQUENCE DESCRIPTION: SEQ ID NO:3:

ATGAGCGAGA AAACCATGCG CGTGCAGGAT TATCCGTTAG CCACCCGCTG CCCGGAGCAT       60

ATCCTGACGC CTACCGGCAA ACCATTGACC GATATTACCC TCGAGAAGGT GCTCTCTGGC      120

GAGGTGGGCC CGCAGGATGT GCGGATCTCC CGCCAGACCC TTGAGTACCA GGCGCAGATT      180

GCCGAGCAGA TGCAGCGCCA TGCGGTGGCG CGCAATTTCC GCCGCGCGGC GGAGCTTATC      240

GCCATTCCTG ACGAGCGCAT TCTGGCTATC TATAACGCGC TGCCCCGTT CCGCTCCTCG       300

CAGGCGGAGC TGCTGGCGAT CGCCGACGAG CTGGAGCACA CCTGGCATGC GACAGTGAAT      360

GCCGCCTTTG TCCGGGAGTC GGCGGAAGTG TATCAGCAGC GGCATAAGCT GCGTAAAGGA      420

AGCTAA                                                                426

(2) INFORMATION FOR SEQ ID NO:4:

(i) SEQUENCE CHARACTERISTICS:
        (A) LENGTH: 1164 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: DHAT (xi) SEQUENCE DESCRIPTION: SEQ ID NO:4:

ATGAGCTATC GTATGTTTGA TTATCTGGTG CCAAACGTTA ACTTTTTTGG CCCCAACGCC       60

ATTTCCGTAG TCGGCGAACG CTGCCAGCTG CTGGGGGGGA AAAAAGCCCT GCTGGTCACC      120

GACAAAGGCC TGCGGGCAAT TAAAGATGGC GCGGTGGACA AAACCCTGCA TTATCTGCGG      180

GAGGCCGGGA TCGAGGTGGC GATCTTTGAC GGCGTCGAGC CGAACCCGAA AGACACCAAC      240

GTGCGCGACG GCCTCGCCGT GTTTCGCCGC GAACAGTGCG ACATCATCGT CACCGTGGGC      300

GGCGGCAGCC CGCACGATTG CGGCAAAGGC ATCGGCATCG CCGCCACCCA TGAGGGCGAT      360

CTGTACCAGT ATGCCGGAAT CGAGACCCTG ACCAACCCGC TGCCGCCTAT CGTCGCGGTC      420
```

```
AATACCACCG CCGGCACCGC CAGCGAGGTC ACCCGCCACT GCGTCCTGAC CAACACCGAA      480

ACCAAAGTGA AGTTTGTGAT CGTCAGCTGG CGCAAACTGC CGTCGGTCTC TATCAACGAT      540

CCACTGCTGA TGATCGGTAA ACCGGCCGCC CTGACCGCGG CGACCGGGAT GGATGCCCTG      600

ACCCACGCCG TAGAGGCCTA TATCTCCAAA GACGCTAACC CGGTGACGGA CGCCGCCGCC      660

ATGCAGGCGA TCCGCCTCAT CGCCCGCAAC CTGCGCCAGG CCGTGGCCCT CGGCAGCAAT      720

CTGCAGGCGC GGGAAAACAT GGCCTATGCT TCTCTGCTGG CCGGGATGGC TTTCAATAAC      780

GCCAACCTCG GCTACGTGCA CGCCATGGCG CACCAGCTGG GCGGCCTGTA CGACATGCCG      840

CACGGCGTGG CCAACGCTGT CCTGCTGCCG CATGTGGCGC GCTACAACCT GATCGCCAAC      900

CCGGAGAAAT TCGCCGATAT CGCTGAACTG ATGGGCGAAA ATATCACCGG ACTGTCCACT      960

CTCGACGCGG CGGAAAAAGC CATCGCCGCT ATCACGCGTC TGTCGATGGA TATCGGTATT     1020

CCGCAGCATC TGCGCGATCT GGGGGTAAAA GAGGCCGACT TCCCCTACAT GGCGGAGATG     1080

GCTCTAAAAG ACGGCAATGC GTTCTCGAAC CCGCGTAAAG GCAACGAGCA GGAGATTGCC     1140

GCGATTTTCC GCCAGGCATT CTGA                                           1164

(2) INFORMATION FOR SEQ ID NO:5:

(i) SEQUENCE CHARACTERISTICS:
        (A) LENGTH:  1380 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (A) ORGANISM:  GPD1

(xi) SEQUENCE DESCRIPTION:  SEQ ID NO:5:

CTTTAATTTT CTTTTATCTT ACTCTCCTAC ATAAGACATC AAGAAACAAT TGTATATTGT       60

ACACCCCCCC CCTCCACAAA CACAAATATT GATAATATAA AGATGTCTGC TGCTGCTGAT      120

AGATTAAACT TAACTTCCGG CCACTTGAAT GCTGGTAGAA AGAGAAGTTC CTCTTCTGTT      180

TCTTTGAAGG CTGCCGAAAA GCCTTTCAAG GTTACTGTGA TTGGATCTGG TAACTGGGGT      240

ACTACTATTG CCAAGGTGGT TGCCGAAAAT TGTAAGGGAT ACCCAGAAGT TTTCGCTCCA      300

ATAGTACAAA TGTGGGTGTT CGAAGAAGAG ATCAATGGTG AAAAATTGAC TGAAATCATA      360

AATACTAGAC ATCAAAACGT GAAATACTTG CCTGGCATCA CTCTACCCGA CAATTTGGTT      420

GCTAATCCAG ACTTGATTGA TTCAGTCAAG GATGTCGACA TCATCGTTTT CAACATTCCA      480

CATCAATTTT TGCCCCGTAT CTGTAGCCAA TTGAAAGGTC ATGTTGATTC ACACGTCAGA      540

GCTATCTCCT GTCTAAAGGG TTTTGAAGTT GGTGCTAAAG GTGTCCAATT GCTATCCTCT      600

TACATCACTG AGGAACTAGG TATTCAATGT GGTGCTCTAT CTGGTGCTAA CATTGCCACC      660

GAAGTCGCTC AAGAACACTG GTCTGAAACA ACAGTTGCTT ACCACATTCC AAAGGATTTC      720

AGAGGCGAGG GCAAGGACGT CGACCATAAG GTTCTAAAGG CCTTGTTCCA CAGACCTTAC      780

TTCCACGTTA GTGTCATCGA AGATGTTGCT GGTATCTCCA TCTGTGGTGC TTTGAAGAAC      840

GTTGTTGCCT TAGGTTGTGG TTTCGTCGAA GGTCTAGGCT GGGGTAACAA CGCTTCTGCT      900

GCCATCCAAA GAGTCGGTTT GGGTGAGATC ATCAGATTCG GTCAAATGTT TTTCCCAGAA      960

TCTAGAGAAG AAACATACTA CCAAGAGTCT GCTGGTGTTT CTGATTTGAT CACCACCTGC     1020

GCTGGTGGTA GAAACGTCAA GGTTGCTAGG CTAATGGCTA CTTCTGGTAA GGACGCCTGG     1080
```

-continued

```
GAATGTGAAA AGGAGTTGTT GAATGGCCAA TCCGCTCAAG GTTTAATTAC CTGCAAAGAA    1140

GTTCACGAAT GGTTGGAAAC ATGTGGCTCT GTCGAAGACT TCCCATTATT TGAAGCCGTA    1200

TACCAAATCG TTTACAACAA CTACCCAATG AAGAACCTGC CGGACATGAT TGAAGAATTA    1260

GATCTACATG AAGATTAGAT TTATTGGAGA AGATAACAT  ATCATACTTC CCCCACTTTT    1320

TTCGAGGCTC TTCTATATCA TATTCATAAA TTAGCATTAT GTCATTTCTC ATAACTACTT    1380
```

(2) INFORMATION FOR SEQ ID NO:6:

(i) SEQUENCE CHARACTERISTICS:
        (A) LENGTH: 2946 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: GPD2

(xi) SEQUENCE DESCRIPTION: SEQ ID NO:6:

```
GAATTCGAGC CTGAAGTGCT GATTACCTTC AGGTAGACTT CATCTTGACC CATCAACCCC      60

AGCGTCAATC CTGCAAATAC ACCACCCAGC AGCACTAGGA TGATAGAGAT AATATAGTAC     120

GTGGTAACGC TTGCCTCATC ACCTACGCTA TGGCCGGAAT CGGCAACATC CCTAGAATTG     180

AGTACGTGTG ATCCGGATAA CAACGGCAGT GAATATATCT TCGGTATCGT AAAGATGTGA     240

TATAAGATGA TGTATACCCA ATGAGGAGCG CCTGATCGTG ACCTAGACCT TAGTGGCAAA     300

AACGACATAT CTATTATAGT GGGGAGAGTT TCGTGCAAAT AACAGACGCA GCAGCAAGTA     360

ACTGTGACGA TATCAACTCT TTTTTTATTA TGTAATAAGC AAACAAGCAC GAATGGGGAA     420

AGCCTATGTG CAATCACCAA GGTCGTCCCT TTTTTCCCAT TTGCTAATTT AGAATTTAAA     480

GAAACCAAAA GAATGAAGAA AGAAAACAAA TACTAGCCCT AACCCTGACT TCGTTTCTAT     540

GATAATACCC TGCTTTAATG AACGGTATGC CCTAGGGTAT ATCTCACTCT GTACGTTACA     600

AACTCCGGTT ATTTTATCGG AACATCCGAG CACCCGCGCC TTCCTCAACC CAGGCACCGC     660

CCCAGGTAAC CGTGCGCGAT GAGCTAATCC TGAGCCATCA CCCACCCCAC CCGTTGATGA     720

CAGCAATTCG GGAGGGCGAA AATAAAACTG GAGCAAGGAA TTACCATCAC CGTCACCATC     780

ACCATCATAT CGCCTTAGCC TCTAGCCATA GCCATCATGC AAGCGTGTAT CTTCTAAGAT     840

TCAGTCATCA TCATTACCGA GTTTGTTTTC CTTCACATGA TGAAGAAGGT TTGAGTATGC     900

TCGAAACAAT AAGACGACGA TGGCTCTGCC ATTGGTTATA TTACGCTTTT GCGGCGAGGT     960

GCCGATGGGT TGCTGAGGGG AAGAGTGTTT AGCTTACGGA CCTATTGCCA TTGTTATTCC    1020

GATTAATCTA TTGTTCAGCA GCTCTTCTCT ACCCTGTCAT TCTAGTATTT TTTTTTTTT     1080

TTTTTGGTTT TACTTTTTTT TCTTCTTGCC TTTTTTTCTT GTTACTTTTT TTCTAGTTTT    1140

TTTTCCTTCC ACTAAGCTTT TTCCTTGATT TATCCTTGGG TTCTTCTTTC TACTCCTTTA    1200

GATTTTTTTT TTATATATTA ATTTTTAAGT TTATGTATTT TGGTAGATTC AATTCTCTTT    1260

CCCTTTCCTT TTCCTTCGCT CCCCTTCCTT ATCAATGCTT GCTGTCAGAA GATTAACAAG    1320

ATACACATTC CTTAAGCGAA CGCATCCGGT GTTATATACT CGTCGTGCAT ATAAAATTTT    1380

GCCTTCAAGA TCTACTTTCC TAAGAAGATC ATTATTACAA ACACAACTGC ACTCAAAGAT    1440

GACTGCTCAT ACTAATATCA AACAGCACAA ACACTGTCAT GAGGACCATC CTATCAGAAG    1500

ATCGGACTCT GCCGTGTCAA TTGTACATTT GAAACGTGCG CCCTTCAAGG TTACAGTGAT    1560

TGGTTCTGGT AACTGGGGGA CCACCATCGC CAAAGTCATT GCGGAAAACA CAGAATTGCA    1620
```

-continued

```
TTCCCATATC TTCGAGCCAG AGGTGAGAAT GTGGGTTTTT GATGAAAAGA TCGGCGACGA    1680

AAATCTGACG GATATCATAA ATACAAGACA CCAGAACGTT AAATATCTAC CCAATATTGA    1740

CCTGCCCCAT AATCTAGTGG CCGATCCTGA TCTTTTACAC TCCATCAAGG GTGCTGACAT    1800

CCTTGTTTTC AACATCCCTC ATCAATTTTT ACCAAACATA GTCAAACAAT TGCAAGGCCA    1860

CGTGGCCCCT CATGTAAGGG CCATCTCGTG TCTAAAAGGG TTCGAGTTGG GCTCCAAGGG    1920

TGTGCAATTG CTATCCTCCT ATGTTACTGA TGAGTTAGGA ATCCAATGTG GCGCACTATC    1980

TGGTGCAAAC TTGGCACCGG AAGTGGCCAA GGAGCATTGG TCCGAAACCA CCGTGGCTTA    2040

CCAACTACCA AAGGATTATC AAGGTGATGG CAAGGATGTA GATCATAAGA TTTTGAAATT    2100

GCTGTTCCAC AGACCTTACT TCCACGTCAA TGTCATCGAT GATGTTGCTG GTATATCCAT    2160

TGCCGGTGCC TTGAAGAACG TCGTGGCACT TGCATGTGGT TTCGTAGAAG GTATGGGATG    2220

GGGTAACAAT GCCTCCGCAG CCATTCAAAG GCTGGGTTTA GGTGAAATTA TCAAGTTCGG    2280

TAGAATGTTT TTCCCAGAAT CCAAAGTCGA GACCTACTAT CAAGAATCCG CTGGTGTTGC    2340

AGATCTGATC ACCACCTGCT CAGGCGGTAG AAACGTCAAG GTTGCCACAT ACATGGCCAA    2400

GACCGGTAAG TCAGCCTTGG AAGCAGAAAA GGAATTGCTT AACGGTCAAT CCGCCCAAGG    2460

GATAATCACA TGCAGAGAAG TTCACGAGTG GCTACAAACA TGTGAGTTGA CCCAAGAATT    2520

CCCAATTATT CGAGGCAGTC TACCAGATAG TCTACAACAA CGTCCGCATG GAAGACCTAC    2580

CGGAGATGAT TGAAGAGCTA GACATCGATG ACGAATAGAC ACTCTCCCCC CCCTCCCCC    2640

TCTGATCTTT CCTGTTGCCT CTTTTTCCCC CAACCAATTT ATCATTATAC ACAAGTTCTA    2700

CAACTACTAC TAGTAACATT ACTACAGTTA TTATAATTTT CTATTCTCTT TTTCTTTAAG    2760

AATCTATCAT TAACGTTAAT TTCTATATAT ACATAACTAC CATTATACAC GCTATTATCG    2820

TTTACATATC ACATCACCGT TAATGAAAGA TACGACACCC TGTACACTAA CACAATTAAA    2880

TAATCGCCAT AACCTTTTCT GTTATCTATA GCCCTTAAAG CTGTTTCTTC GAGCTTTTCA    2940

CTGCAG                                                                2946
```

(2) INFORMATION FOR SEQ ID NO:7:

(i) SEQUENCE CHARACTERISTICS:
        (A) LENGTH: 3178 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: GUT2

(xi) SEQUENCE DESCRIPTION: SEQ ID NO:7:

```
CTGCAGAACT TCGTCTGCTC TGTGCCCATC CTCGCGGTTA GAAAGAAGCT GAATTGTTTC     60

ATGCGCAAGG GCATCAGCGA GTGACCAATA ATCACTGCAC TAATTCCTTT TTAGCAACAC    120

ATACTTATAT ACAGCACCAG ACCTTATGTC TTTTCTCTGC TCCGATACGT TATCCCACCC    180

AACTTTTATT TCAGTTTTGG CAGGGAAAT TTCACAACCC CGCACGCTAA AAATCGTATT    240

TAAACTTAAA AGAGAACAGC CACAAATAGG GAACTTTGGT CTAAACGAAG GACTCTCCCT    300

CCCTTATCTT GACCGTGCTA TTGCCATCAC TGCTACAAGA CTAAATACGT ACTAATATAT    360

GTTTTCGGTA ACGAGAAGAA GAGCTGCCGG TGCAGCTGCT GCCATGGCCA CAGCCACGGG    420

GACGCTGTAC TGGATGACTA GCCAAGGTGA TAGGCCGTTA GTGCACAATG ACCCGAGCTA    480
```

-continued

| | | | |
|---|---|---|---|
| CATGGTGCAA | TTCCCCACCG CCGCTCCACC | GGCAGGTCTC TAGACGAGAC CTGCTGGACC | 540 |
| GTCTGGACAA | GACGCATCAA TTCGACGTGT | TGATCATCGG TGGCGGGGCC ACGGGGACAG | 600 |
| GATGTGCCCT | AGATGCTGCG ACCAGGGGAC | TCAATGTGGC CCTTGTTGAA AAGGGGGATT | 660 |
| TTGCCTCGGG | AACGTCGTCC AAATCTACCA | AGATGATTCA CGGTGGGGTG CGGTACTTAG | 720 |
| AGAAGGCCTT | CTGGGAGTTC TCCAAGGCAC | AACTGGATCT GGTCATCGAG GCACTCAACG | 780 |
| AGCGTAAACA | TCTTATCAAC ACTGCCCCTC | ACCTGTGCAC GGTGCTACCA ATTCTGATCC | 840 |
| CCATCTACAG | CACCTGGCAG GTCCCGTACA | TCTATATGGG CTGTAAATTC TACGATTTCT | 900 |
| TTGGCGGTTC | CCAAAACTTG AAAAAATCAT | ACCTACTGTC CAAATCCGCC ACCGTGGAGA | 960 |
| AGGCTCCCAT | GCTTACCACA GACAATTTAA | AGGCCTCGCT TGTGTACCAT GATGGGTCCT | 1020 |
| TTAACGACTC | GCGTTTGAAC GCCACTTTAG | CCATCACGGG TGTGGAGAAC GGCGCTACCG | 1080 |
| TCTTGATCTA | TGTCGAGGTA CAAAAATTGA | TCAAAGACCC AACTTCTGGT AAGGTTATCG | 1140 |
| GTGCCGAGGC | CCGGGACGTT GAGACTAATG | AGCTTGTCAG AATCAACGCT AAATGTGTGG | 1200 |
| TCAATGCCAC | GGGCCCATAC AGTGACGCCA | TTTTGCAAAT GGACCGCAAC CCATCCGGTC | 1260 |
| TGCCGGACTC | CCCGCTAAAC GACAACTCCA | AGATCAAGTC GACTTTCAAT CAAATCTCCG | 1320 |
| TCATGGACCC | GAAAATGGTC ATCCCATCTA | TTGGCGTTCA CATCGTATTG CCCTCTTTTT | 1380 |
| ACTCCCCGAA | GGATATGGGT TGTTGGACG | TCAGAACCTC TGATGGCAGA GTGATGTTCT | 1440 |
| TTTTACCTTG | GCAGGGCAAA GTCCTTGCCG | GCACCACAGA CATCCCACTA AAGCAAGTCC | 1500 |
| CAGAAAACCC | TATGCCTACA GAGGCTGATA | TTCAAGATAT CTTGAAAGAA CTACAGCACT | 1560 |
| ATATCGAATT | CCCCGTGAAA AGAGAAGACG | TGCTAAGTGC ATGGGCTGGT GTCAGACCTT | 1620 |
| TGGTCAGAGA | TCCACGTACA ATCCCCGCAG | ACGGGAAGAA GGGCTCTGCC ACTCAGGGCG | 1680 |
| TGGTAAGATC | CCACTTCTTG TTCACTTCGG | ATAATGGCCT AATTACTATT GCAGGTGGTA | 1740 |
| AATGGACTAC | TTCAGACAA ATGGCTGAGG | AAACAGTCGA CAAAGTTGTC GAAGTTGGCG | 1800 |
| GATTCCACAA | CCTGAAACCT TGTCACACAA | GAGATATTAA GCTTGCTGGT GCAGAAGAAT | 1860 |
| GGACGCAAAA | CTATGTGGCT TTATTGGCTC | AAAACTACCA TTTATCATCA AAAATGTCCA | 1920 |
| ACTACTTGGT | TCAAAACTAC GGAACCCGTT | CCTCTATCAT TTGCGAATTT TCAAAGAAT | 1980 |
| CCATGGAAAA | TAAACTGCCT TTGTCCTTAG | CCGACAAGGA AAATAACGTA ATCTACTCTA | 2040 |
| GCGAGGAGAA | CAACTTGGTC AATTTTGATA | CTTTCAGATA TCCATTCACA ATCGGTGAGT | 2100 |
| TAAAGTATTC | CATGCAGTAC GAATATTGTA | GAACTCCCTT GGACTTCCTT TTAAGAAGAA | 2160 |
| CAAGATTCGC | CTTCTTGGAC GCCAAGGAAG | CTTTGAATGC CGTGCATGCC ACCGTCAAAG | 2220 |
| TTATGGGTGA | TGAGTTCAAT TGGTCGGAGA | AAAAGAGGCA GTGGGAACTT GAAAAAACTG | 2280 |
| TGAACTTCAT | CCAAGGACGT TTCGGTGTCT | AAATCGATCA TGATAGTTAA GGGTGACAAA | 2340 |
| GATAACATTC | ACAAGAGTAA TAATAATGGT | AATGATGATA ATAATAATAA TGATAGTAAT | 2400 |
| AACAATAATA | ATAATGGTGG TAATGGCAAT | GAAATCGCTA TTATTACCTA TTTTCCTTAA | 2460 |
| TGGAAGAGTT | AAAGTAAACT AAAAAAAACTA | CAAAAATATA TGAAGAAAAA AAAAAAAGA | 2520 |
| GGTAATAGAC | TCTACTACTA CAATTGATCT | TCAAATTATG ACCTTCCTAG TGTTTATATT | 2580 |
| CTATTTCCAA | TACATAATAT AATCTATATA | ATCATTGCTG GTAGACTTCC GTTTTAATAT | 2640 |
| CGTTTTAATT | ATCCCCTTTA TCTCTAGTCT | AGTTTTATCA TAAAATATAG AAACACTAAA | 2700 |
| TAATATTCTT | CAAACGGTCC TGGTGCATAC | GCAATACATA TTTATGGTGC AAAAAAAAAA | 2760 |
| ATGGAAAATT | TTGCTAGTCA TAAACCCTTT | CATAAAACAA TACGTAGACA TCGCTACTTG | 2820 |
| AAATTTTCAA | GTTTTTATCA GATCCATGTT | TCCTATCTGC CTTGACAACC TCATCGTCGA | 2880 |

```
AATAGTACCA TTTAGAACGC CCAATATTCA CATTGTGTTC AAGGTCTTTA TTCACCAGTG    2940

ACGTGTAATG GCCATGATTA ATGTGCCTGT ATGGTTAACC ACTCCAAATA GCTTATATTT    3000

CATAGTGTCA TTGTTTTTCA ATATAATGTT TAGTATCAAT GGATATGTTA CGACGGTGTT    3060

ATTTTTCTTG GTCAAATCGT AATAAAATCT CGATAAATGG ATGACTAAGA TTTTTGGTAA    3120

AGTTACAAAA TTTATCGTTT TCACTGTTGT CAATTTTTTG TTCTTGTAAT CACTCGAG     3178
```

(2) INFORMATION FOR SEQ ID NO:8:

(i) SEQUENCE CHARACTERISTICS:
        (A) LENGTH:  816 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (A) ORGANISM:  GPP1

(xi) SEQUENCE DESCRIPTION:  SEQ ID NO:8:

```
ATGAAACGTT TCAATGTTTT AAAATATATC AGAACAACAA AAGCAAATAT ACAAACCATC      60

GCAATGCCTT TGACCACAAA ACCTTTATCT TTGAAAATCA ACGCCGCTCT ATTCGATGTT     120

GACGGTACCA TCATCATCTC TCAACCAGCC ATTGCTGCTT TCTGGAGAGA TTTCGGTAAA     180

GACAAGCCTT ACTTCGATGC CGAACACGTT ATTCACATCT CTCACGGTTG GAGAACTTAC     240

GATGCCATTG CCAAGTTCGC TCCAGACTTT GCTGATGAAG AATACGTTAA CAAGCTAGAA     300

GGTGAAATCC CAGAAAAGTA CGGTGAACAC TCCATCGAAG TTCCAGGTGC TGTCAAGTTG     360

TGTAATGCTT TGAACGCCTT GCCAAAGGAA AAATGGGCTG TCGCCACCTC TGGTACCCGT     420

GACATGGCCA AGAAATGGTT CGACATTTTG AAGATCAAGA GACCAGAATA CTTCATCACC     480

GCCAATGATG TCAAGCAAGG TAAGCCTCAC CCAGAACCAT ACTTAAAGGG TAGAAACGGT     540

TTGGGTTTCC CAATTAATGA ACAAGACCCA TCCAAATCTA AGGTTGTTGT CTTTGAAGAC     600

GCACCAGCTG GTATTGCTGC TGGTAAGGCT GCTGGCTGTA AAATCGTTGG TATTGCTACC     660

ACTTTCGATT TGGACTTCTT GAAGGAAAAG GGTTGTGACA TCATTGTCAA GAACCACGAA     720

TCTATCAGAG TCGGTGAATA CAACGCTGAA ACCGATGAAG TCGAATTGAT CTTTGATGAC     780

TACTTATACG CTAAGGATGA CTTGTTGAAA TGGTAA                              816
```

(2) INFORMATION FOR SEQ ID NO:9:

(i) SEQUENCE CHARACTERISTICS:
        (A) LENGTH:  753 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (A) ORGANISM:  GPP2

(xi) SEQUENCE DESCRIPTION:  SEQ ID NO:9:

```
ATGGGATTGA CTACTAAACC TCTATCTTTG AAAGTTAACG CCGCTTTGTT CGACGTCGAC      60

GGTACCATTA TCATCTCTCA ACCAGCCATT GCTGCATTCT GGAGGGATTT CGGTAAGGAC     120

AAACCTTATT TCGATGCTGA ACACGTTATC CAAGTCTCGC ATGGTTGGAG AACGTTTGAT     180

GCCATTGCTA AGTTCGCTCC AGACTTTGCC AATGAAGAGT ATGTTAACAA ATTAGAAGCT     240
```

-continued

```
GAAATTCCGG TCAAGTACGG TGAAAAATCC ATTGAAGTCC CAGGTGCAGT TAAGCTGTGC      300

AACGCTTTGA ACGCTCTACC AAAAGAGAAA TGGGCTGTGG CAACTTCCGG TACCCGTGAT      360

ATGGCACAAA ATGGTTCGA GCATCTGGGA ATCAGGAGAC CAAAGTACTT CATTACCGCT       420

AATGATGTCA AACAGGGTAA GCCTCATCCA GAACCATATC TGAAGGGCAG GAATGGCTTA     480

GGATATCCGA TCAATGAGCA AGACCCTTCC AAATCTAAGG TAGTAGTATT TGAAGACGCT     540

CCAGCAGGTA TTGCCGCCGG AAAAGCCGCC GGTTGTAAGA TCATTGGTAT TGCCACTACT    600

TTCGACTTGG ACTTCCTAAA GGAAAAAGGC TGTGACATCA TTGTCAAAAA CCACGAATCC    660

ATCAGAGTTG GCGGCTACAA TGCCGAAACA GACGAAGTTG AATTCATTTT TGACGACTAC   720

TTATATGCTA AGGACGATCT GTTGAAATGG TAA                                 753
```

(2) INFORMATION FOR SEQ ID NO:10:

(i) SEQUENCE CHARACTERISTICS:
        (A) LENGTH: 2520 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: GUT1

(xi) SEQUENCE DESCRIPTION: SEQ ID NO:10:

```
TGTATTGGCC ACGATAACCA CCCTTTGTAT ACTGTTTTTG TTTTTCACAT GGTAAATAAC      60

GACTTTTATT AAACAACGTA TGTAAAAACA TAACAAGAAT CTACCCATAC AGGCCATTTC     120

GTAATTCTTC TCTTCTAATT GGAGTAAAAC CATCAATTAA AGGGTGTGGA GTAGCATAGT    180

GAGGGGCTGA CTGCATTGAC AAAAAAATTG AAAAAAAAAA AGGAAAAGGA AAGGAAAAAA  240

AGACAGCCAA GACTTTTAGA ACGGATAAGG TGTAATAAAA TGTGGGGGGA TGCCTGTTCT   300

CGAACCATAT AAAATATACC ATGTGGTTTG AGTTGTGGCC GGAACTATAC AAATAGTTAT   360

ATGTTTCCCT CTCTCTTCCG ACTTGTAGTA TTCTCCAAAC GTTACATATT CCGATCAAGC   420

CAGCGCCTTT ACACTAGTTT AAAACAAGAA CAGAGCCGTA TGTCCAAAAT AATGGAAGAT  480

TTACGAAGTG ACTACGTCCC GCTTATCGCC AGTATTGATG TAGGAACGAC CTCATCCAGA  540

TGCATTCTGT TCAACAGATG GGGCCAGGAC GTTTCAAAAC ACCAAATTGA ATATTCAACT  600

TCAGCATCGA AGGGCAAGAT TGGGGTGTCT GGCCTAAGGA GACCCTCTAC AGCCCCAGCT  660

CGTGAAACAC CAAACGCCGG TGACATCAAA ACCAGCGGAA AGCCCATCTT TTCTGCAGAA  720

GGCTATGCCA TTCAAGAAAC CAAATTCCTA AAAATCGAGG AATTGGACTT GGACTTCCAT  780

AACGAACCCA CGTTGAAGTT CCCCAAACCG GGTTGGGTTG AGTGCCATCC GCAGAAATTA  840

CTGGTGAACG TCGTCCAATG CCTTGCCTCA AGTTTGCTCT CTCTGCAGAC TATCAACAGC  900

GAACGTGTAG CAAACGGTCT CCCACCTTAC AAGGTAATAT GCATGGGTAT AGCAAACATG  960

AGAGAAACCA CAATTCTGTG GTCCCGCCGC ACAGGAAAAC CAATTGTTAA CTACGGTATT  1020

GTTTGGAACG ACACCAGAAC GATCAAAATC GTTAGAGACA AATGGCAAAA CACTAGCGTC  1080

GATAGGCAAC TGCAGCTTAG ACAGAAGACT GGATTGCCAT TGCTCTCCAC GTATTTCTCC  1140

TGTTCCAAGC TGCGCTGGTT CCTCGACAAT GAGCCTCTGT GTACCAAGGC GTATGAGGAG  1200

AACGACCTGA TGTTCGGCAC TGTGGACACA TGGCTGATTT ACCAATTAAC TAAACAAAAG  1260

GCGTTCGTTT CTGACGTAAC CAACGCTTCC AGAACTGGAT TTATGAACCT CTCCACTTTA  1320

AAGTACGACA ACGAGTTGCT GGAATTTTGG GGTATTGACA AGAACCTGAT TCACATGCCC  1380
```

-continued

```
GAAATTGTGT CCTCATCTCA ATACTACGGT GACTTTGGCA TTCCTGATTG GATAATGGAA    1440

AAGCTACACG ATTCGCCAAA AACAGTACTG CGAGATCTAG TCAAGAGAAA CCTGCCCATA    1500

CAGGGCTGTC TGGGCGACCA AAGCGCATCC ATGGTGGGGC AACTCGCTTA CAAACCCGGT    1560

GCTGCAAAAT GTACTTATGG TACCGGTTGC TTTTTACTGT ACAATACGGG GACCAAAAAA    1620

TTGATCTCCC AACATGGCGC ACTGACGACT CTAGCATTTT GGTTCCCACA TTTGCAAGAG    1680

TACGGTGGCC AAAAACCAGA ATTGAGCAAG CCACATTTTG CATTAGAGGG TTCCGTCGCT    1740

GTGGCTGGTG CTGTGGTCCA ATGGCTACGT GATAATTTAC GATTGATCGA TAAATCAGAG    1800

GATGTCGGAC CGATTGCATC TACGGTTCCT GATTCTGGTG GCGTAGTTTT CGTCCCCGCA    1860

TTTAGTGGCC TATTCGCTCC CTATTGGGAC CCAGATGCCA GAGCCACCAT AATGGGGATG    1920

TCTCAATTCA CTACTGCCTC CCACATCGCC AGAGCTGCCG TGGAAGGTGT TTGCTTTCAA    1980

GCCAGGGCTA TCTTGAAGGC AATGAGTTCT GACGCGTTTG GTGAAGGTTC CAAAGACAGG    2040

GACTTTTTAG AGGAAATTTC CGACGTCACA TATGAAAAGT CGCCCCTGTC GGTTCTGGCA    2100

GTGGATGGCG GGATGTCGAG GTCTAATGAA GTCATGCAAA TTCAAGCCGA TATCCTAGGT    2160

CCCTGTGTCA AAGTCAGAAG GTCTCCGACA GCGGAATGTA CCGCATTGGG GGCAGCCATT    2220

GCAGCCAATA TGGCTTTCAA GGATGTGAAC GAGCGCCCAT TATGGAAGGA CCTACACGAT    2280

GTTAAGAAAT GGGTCTTTTA CAATGGAATG GAGAAAAACG AACAAATATC ACCAGAGGCT    2340

CATCCAAACC TTAAGATATT CAGAAGTGAA TCCGACGATG CTGAAAGGAG AAAGCATTGG    2400

AAGTATTGGG AAGTTGCCGT GGAAAGATCC AAAGGTTGGC TGAAGGACAT AGAAGGTGAA    2460

CACGAACAGG TTCTAGAAAA CTTCCAATAA CAACATAAAT AATTTCTATT AACAATGTAA    2520
```

(2) INFORMATION FOR SEQ ID NO:11:

(i) SEQUENCE CHARACTERISTICS:
        (A) LENGTH: 391 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: GPD1

(xi) SEQUENCE DESCRIPTION: SEQ ID NO:11:

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125
```

-continued

```
Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

(2) INFORMATION FOR SEQ ID NO:12:

(i) SEQUENCE CHARACTERISTICS:
        (A) LENGTH:  384 amino acids
        (B) TYPE:  amino acid
        (C) STRANDEDNESS:  unknown
        (D) TOPOLOGY:  unknown (ii) MOLECULE TYPE:  protein (vi) ORIGINAL SOURCE:
        (A) ORGANISM:  GPD2

(xi) SEQUENCE DESCRIPTION:  SEQ ID NO:12:

Met Thr Ala His Thr Asn Ile Lys Gln His Lys His Cys His Glu Asp
1               5                   10                  15

His Pro Ile Arg Arg Ser Asp Ser Ala Val Ser Ile Val His Leu Lys
            20                  25                  30

Arg Ala Pro Phe Lys Val Thr Val Ile Gly Ser Gly Asn Trp Gly Thr
        35                  40                  45

Thr Ile Ala Lys Val Ile Ala Glu Asn Thr Glu Leu His Ser His Ile
    50                  55                  60
```

```
Phe Glu Pro Glu Val Arg Met Trp Val Phe Asp Glu Lys Ile Gly Asp
 65                  70                  75                  80

Glu Asn Leu Thr Asp Ile Ile Asn Thr Arg His Gln Asn Val Lys Tyr
                 85                  90                  95

Leu Pro Asn Ile Asp Leu Pro His Asn Leu Val Ala Asp Pro Asp Leu
                100                 105                 110

Leu His Ser Ile Lys Gly Ala Asp Ile Leu Val Phe Asn Ile Pro His
                115                 120                 125

Gln Phe Leu Pro Asn Ile Val Lys Gln Leu Gln Gly His Val Ala Pro
130                 135                 140

His Val Arg Ala Ile Ser Cys Leu Lys Gly Phe Glu Leu Gly Ser Lys
145                 150                 155                 160

Gly Val Gln Leu Leu Ser Ser Tyr Val Thr Asp Glu Leu Gly Ile Gln
                165                 170                 175

Cys Gly Ala Leu Ser Gly Ala Asn Leu Ala Pro Glu Val Ala Lys Glu
                180                 185                 190

His Trp Ser Glu Thr Thr Val Ala Tyr Gln Leu Pro Lys Asp Tyr Gln
                195                 200                 205

Gly Asp Gly Lys Asp Val Asp His Lys Ile Leu Lys Leu Leu Phe His
210                 215                 220

Arg Pro Tyr Phe His Val Asn Val Ile Asp Asp Val Ala Gly Ile Ser
225                 230                 235                 240

Ile Ala Gly Ala Leu Lys Asn Val Val Ala Leu Ala Cys Gly Phe Val
                245                 250                 255

Glu Gly Met Gly Trp Gly Asn Asn Ala Ser Ala Ala Ile Gln Arg Leu
                260                 265                 270

Gly Leu Gly Glu Ile Ile Lys Phe Gly Arg Met Phe Phe Pro Glu Ser
                275                 280                 285

Lys Val Glu Thr Tyr Tyr Gln Glu Ser Ala Gly Val Ala Asp Leu Ile
                290                 295                 300

Thr Thr Cys Ser Gly Gly Arg Asn Val Lys Val Ala Thr Tyr Met Ala
305                 310                 315                 320

Lys Thr Gly Lys Ser Ala Leu Glu Ala Glu Lys Glu Leu Leu Asn Gly
                325                 330                 335

Gln Ser Ala Gln Gly Ile Ile Thr Cys Arg Glu Val His Glu Trp Leu
                340                 345                 350

Gln Thr Cys Glu Leu Thr Gln Glu Phe Pro Ile Ile Arg Gly Ser Leu
                355                 360                 365

Pro Asp Ser Leu Gln Gln Arg Pro His Gly Arg Pro Thr Gly Asp Asp
370                 375                 380

(2) INFORMATION FOR SEQ ID NO:13:

(i) SEQUENCE CHARACTERISTICS:
        (A) LENGTH:  614 amino acids
        (B) TYPE:  amino acid
        (C) STRANDEDNESS:  unknown
        (D) TOPOLOGY:  unknown (ii) MOLECULE TYPE:  protein (vi) ORIGINAL SOURCE:
        (A) ORGANISM:  GUT2

(xi) SEQUENCE DESCRIPTION:  SEQ ID NO:13:

Met Thr Arg Ala Thr Trp Cys Asn Ser Pro Pro Leu His Arg Gln
 1               5                  10                  15
```

```
Val Ser Arg Arg Asp Leu Leu Asp Arg Leu Asp Lys Thr His Gln Phe
         20                  25                  30

Asp Val Leu Ile Ile Gly Gly Ala Thr Gly Thr Gly Cys Ala Leu
         35                  40                  45

Asp Ala Ala Thr Arg Gly Leu Asn Val Ala Leu Val Glu Lys Gly Asp
     50                  55                  60

Phe Ala Ser Gly Thr Ser Ser Lys Ser Thr Lys Met Ile His Gly Gly
65                  70                  75                  80

Val Arg Tyr Leu Glu Lys Ala Phe Trp Glu Phe Ser Lys Ala Gln Leu
                 85                  90                  95

Asp Leu Val Ile Glu Ala Leu Asn Glu Arg Lys His Leu Ile Asn Thr
             100                 105                 110

Ala Pro His Leu Cys Thr Val Leu Pro Ile Leu Ile Pro Ile Tyr Ser
         115                 120                 125

Thr Trp Gln Val Pro Tyr Ile Tyr Met Gly Cys Lys Phe Tyr Asp Phe
         130                 135                 140

Phe Gly Gly Ser Gln Asn Leu Lys Lys Ser Tyr Leu Leu Ser Lys Ser
145                 150                 155                 160

Ala Thr Val Glu Lys Ala Pro Met Leu Thr Thr Asp Asn Leu Lys Ala
                 165                 170                 175

Ser Leu Val Tyr His Asp Gly Ser Phe Asn Asp Ser Arg Leu Asn Ala
             180                 185                 190

Thr Leu Ala Ile Thr Gly Val Glu Asn Gly Ala Thr Val Leu Ile Tyr
         195                 200                 205

Val Glu Val Gln Lys Leu Ile Lys Asp Pro Thr Ser Gly Lys Val Ile
         210                 215                 220

Gly Ala Glu Ala Arg Asp Val Glu Thr Asn Glu Leu Val Arg Ile Asn
225                 230                 235                 240

Ala Lys Cys Val Val Asn Ala Thr Gly Pro Tyr Ser Asp Ala Ile Leu
                 245                 250                 255

Gln Met Asp Arg Asn Pro Ser Gly Leu Pro Asp Ser Pro Leu Asn Asp
             260                 265                 270

Asn Ser Lys Ile Lys Ser Thr Phe Asn Gln Ile Ser Val Met Asp Pro
         275                 280                 285

Lys Met Val Ile Pro Ser Ile Gly Val His Ile Val Leu Pro Ser Phe
         290                 295                 300

Tyr Ser Pro Lys Asp Met Gly Leu Leu Asp Val Arg Thr Ser Asp Gly
305                 310                 315                 320

Arg Val Met Phe Phe Leu Pro Trp Gln Gly Lys Val Leu Ala Gly Thr
                 325                 330                 335

Thr Asp Ile Pro Leu Lys Gln Val Pro Glu Asn Pro Met Pro Thr Glu
             340                 345                 350

Ala Asp Ile Gln Asp Ile Leu Lys Glu Leu Gln His Tyr Ile Glu Phe
         355                 360                 365

Pro Val Lys Arg Glu Asp Val Leu Ser Ala Trp Ala Gly Val Arg Pro
         370                 375                 380

Leu Val Arg Asp Pro Arg Thr Ile Pro Ala Asp Gly Lys Lys Gly Ser
385                 390                 395                 400

Ala Thr Gln Gly Val Val Arg Ser His Phe Leu Phe Thr Ser Asp Asn
                 405                 410                 415

Gly Leu Ile Thr Ile Ala Gly Gly Lys Trp Thr Thr Tyr Arg Gln Met
             420                 425                 430

Ala Glu Glu Thr Val Asp Lys Val Val Glu Val Gly Gly Phe His Asn
```

```
                    435                 440                 445
Leu Lys Pro Cys His Thr Arg Asp Ile Lys Leu Ala Gly Ala Glu Glu
450                 455                 460

Trp Thr Gln Asn Tyr Val Ala Leu Leu Ala Gln Asn Tyr His Leu Ser
465                 470                 475                 480

Ser Lys Met Ser Asn Tyr Leu Val Gln Asn Tyr Gly Thr Arg Ser Ser
                485                 490                 495

Ile Ile Cys Glu Phe Phe Lys Glu Ser Met Glu Asn Lys Leu Pro Leu
                500                 505                 510

Ser Leu Ala Asp Lys Glu Asn Val Ile Tyr Ser Ser Glu Glu Asn
            515                 520                 525

Asn Leu Val Asn Phe Asp Thr Phe Arg Tyr Pro Phe Thr Ile Gly Glu
530                 535                 540

Leu Lys Tyr Ser Met Gln Tyr Glu Tyr Cys Arg Thr Pro Leu Asp Phe
545                 550                 555                 560

Leu Leu Arg Arg Thr Arg Phe Ala Phe Leu Asp Ala Lys Glu Ala Leu
                565                 570                 575

Asn Ala Val His Ala Thr Val Lys Val Met Gly Asp Glu Phe Asn Trp
            580                 585                 590

Ser Glu Lys Lys Arg Gln Trp Glu Leu Glu Lys Thr Val Asn Phe Ile
            595                 600                 605

Gln Gly Arg Phe Gly Val
            610

(2) INFORMATION FOR SEQ ID NO:14:

(i) SEQUENCE CHARACTERISTICS:
        (A) LENGTH: 339 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: GPSA (xi) SEQUENCE DESCRIPTION: SEQ ID NO:14:

Met Asn Gln Arg Asn Ala Ser Met Thr Val Ile Gly Ala Gly Ser Tyr
1               5                   10                  15

Gly Thr Ala Leu Ala Ile Thr Leu Ala Arg Asn Gly His Glu Val Val
                20                  25                  30

Leu Trp Gly His Asp Pro Glu His Ile Ala Thr Leu Glu Arg Asp Arg
            35                  40                  45

Cys Asn Ala Ala Phe Leu Pro Asp Val Pro Phe Pro Asp Thr Leu His
50                  55                  60

Leu Glu Ser Asp Leu Ala Thr Ala Leu Ala Ala Ser Arg Asn Ile Leu
65                  70                  75                  80

Val Val Val Pro Ser His Val Phe Gly Glu Val Leu Arg Gln Ile Lys
                85                  90                  95

Pro Leu Met Arg Pro Asp Ala Arg Leu Val Trp Ala Thr Lys Gly Leu
                100                 105                 110

Glu Ala Glu Thr Gly Arg Leu Leu Gln Asp Val Ala Arg Glu Ala Leu
            115                 120                 125

Gly Asp Gln Ile Pro Leu Ala Val Ile Ser Gly Pro Thr Phe Ala Lys
130                 135                 140

Glu Leu Ala Ala Gly Leu Pro Thr Ala Ile Ser Leu Ala Ser Thr Asp
```

-continued

```
                145                 150                 155                 160
Gln Thr Phe Ala Asp Asp Leu Gln Gln Leu Leu His Cys Gly Lys Ser
                    165                 170                 175
Phe Arg Val Tyr Ser Asn Pro Asp Phe Ile Gly Val Gln Leu Gly Gly
                180                 185                 190
Ala Val Lys Asn Val Ile Ala Ile Gly Ala Gly Met Ser Asp Gly Ile
            195                 200                 205
Gly Phe Gly Ala Asn Ala Arg Thr Ala Leu Ile Thr Arg Gly Leu Ala
        210                 215                 220
Glu Met Ser Arg Leu Gly Ala Ala Leu Gly Ala Asp Pro Ala Thr Phe
225                 230                 235                 240
Met Gly Met Ala Gly Leu Gly Asp Leu Val Leu Thr Cys Thr Asp Asn
                245                 250                 255
Gln Ser Arg Asn Arg Arg Phe Gly Met Met Leu Gly Gln Gly Met Asp
                260                 265                 270
Val Gln Ser Ala Gln Glu Lys Ile Gly Gln Val Val Glu Gly Tyr Arg
            275                 280                 285
Asn Thr Lys Glu Val Arg Glu Leu Ala His Arg Phe Gly Val Glu Met
        290                 295                 300
Pro Ile Thr Glu Glu Ile Tyr Gln Val Leu Tyr Cys Gly Lys Asn Ala
305                 310                 315                 320
Arg Glu Ala Ala Leu Thr Leu Leu Gly Arg Ala Arg Lys Asp Glu Arg
                325                 330                 335
Ser Ser His
```

(2) INFORMATION FOR SEQ ID NO:15:

(i) SEQUENCE CHARACTERISTICS:
        (A) LENGTH: 501 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: GLPD (xi) SEQUENCE DESCRIPTION: SEQ ID NO:15:

```
Met Glu Thr Lys Asp Leu Ile Val Ile Gly Gly Gly Ile Asn Gly Ala
1               5                   10                  15
Gly Ile Ala Ala Asp Ala Ala Gly Arg Gly Leu Ser Val Leu Met Leu
                20                  25                  30
Glu Ala Gln Asp Leu Ala Cys Ala Thr Ser Ser Ala Ser Ser Lys Leu
            35                  40                  45
Ile His Gly Gly Leu Arg Tyr Leu Glu His Tyr Glu Phe Arg Leu Val
        50                  55                  60
Ser Glu Ala Leu Ala Glu Arg Glu Val Leu Leu Lys Met Ala Pro His
65                  70                  75                  80
Ile Ala Phe Pro Met Arg Phe Arg Leu Pro His Arg Pro His Leu Arg
                85                  90                  95
Pro Ala Trp Met Ile Arg Ile Gly Leu Phe Met Tyr Asp His Leu Gly
                100                 105                 110
Lys Arg Thr Ser Leu Pro Gly Ser Thr Gly Leu Arg Phe Gly Ala Asn
            115                 120                 125
Ser Val Leu Lys Pro Glu Ile Lys Arg Gly Phe Glu Tyr Ser Asp Cys
        130                 135                 140
```

```
Trp Val Asp Asp Ala Arg Leu Val Leu Ala Asn Ala Gln Met Val Val
145                 150                 155                 160

Arg Lys Gly Gly Glu Val Leu Thr Arg Thr Arg Ala Thr Ser Ala Arg
                165                 170                 175

Arg Glu Asn Gly Leu Trp Ile Val Glu Ala Glu Asp Ile Asp Thr Gly
            180                 185                 190

Lys Lys Tyr Ser Trp Gln Ala Arg Gly Leu Val Asn Ala Thr Gly Pro
        195                 200                 205

Trp Val Lys Gln Phe Phe Asp Asp Gly Met His Leu Pro Ser Pro Tyr
210                 215                 220

Gly Ile Arg Leu Ile Lys Gly Ser His Ile Val Val Pro Arg Val His
225                 230                 235                 240

Thr Gln Lys Gln Ala Tyr Ile Leu Gln Asn Glu Asp Lys Arg Ile Val
                245                 250                 255

Phe Val Ile Pro Trp Met Asp Glu Phe Ser Ile Ile Gly Thr Thr Asp
            260                 265                 270

Val Glu Tyr Lys Gly Asp Pro Lys Ala Val Lys Ile Glu Glu Ser Glu
        275                 280                 285

Ile Asn Tyr Leu Leu Asn Val Tyr Asn Thr His Phe Lys Lys Gln Leu
290                 295                 300

Ser Arg Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335

Asp Ile His Asp Glu Asn Gly Lys Ala Pro Leu Leu Ser Val Phe Gly
            340                 345                 350

Gly Lys Leu Thr Thr Tyr Arg Lys Leu Ala Glu His Ala Leu Glu Lys
        355                 360                 365

Leu Thr Pro Tyr Tyr Gln Gly Ile Gly Pro Ala Trp Thr Lys Glu Ser
370                 375                 380

Val Leu Pro Gly Gly Ala Ile Glu Gly Asp Arg Asp Asp Tyr Ala Ala
385                 390                 395                 400

Arg Leu Arg Arg Arg Tyr Pro Phe Leu Thr Glu Ser Leu Ala Arg His
                405                 410                 415

Tyr Ala Arg Thr Tyr Gly Ser Asn Ser Glu Leu Leu Leu Gly Asn Ala
            420                 425                 430

Gly Thr Val Ser Asp Leu Gly Asp Phe Gly His Glu Phe Tyr Glu
        435                 440                 445

Ala Glu Leu Lys Tyr Leu Val Asp His Glu Trp Val Arg Arg Ala Asp
450                 455                 460

Asp Ala Leu Trp Arg Arg Thr Lys Gln Gly Met Trp Leu Asn Ala Asp
465                 470                 475                 480

Gln Gln Ser Arg Val Ser Gln Trp Leu Val Glu Tyr Thr Gln Gln Arg
                485                 490                 495

Leu Ser Leu Ala Ser
            500
```

(2) INFORMATION FOR SEQ ID NO:16:

(i) SEQUENCE CHARACTERISTICS:
        (A) LENGTH: 542 amino acids
        (B) TYPE: amino acid
        (C) STRANDEDNESS: unknown
        (D) TOPOLOGY: unknown (ii) MOLECULE TYPE: protein (vi) ORIGINAL SOURCE:
    (A) ORGANISM: GLPABC (xi) SEQUENCE DESCRIPTION: SEQ ID NO:16:

```
Met Lys Thr Arg Asp Ser Gln Ser Asp Val Ile Ile Gly Gly
1               5                  10                 15

Gly Ala Thr Gly Ala Gly Ile Ala Arg Asp Cys Ala Leu Arg Gly Leu
                20                  25                  30

Arg Val Ile Leu Val Glu Arg His Asp Ile Ala Thr Gly Ala Thr Gly
            35                  40                  45

Arg Asn His Gly Leu Leu His Ser Gly Ala Arg Tyr Ala Val Thr Asp
        50                  55                  60

Ala Glu Ser Ala Arg Glu Cys Ile Ser Glu Asn Gln Ile Leu Lys Arg
65                  70                  75                  80

Ile Ala Arg His Cys Val Glu Pro Thr Asn Gly Leu Phe Ile Thr Leu
                85                  90                  95

Pro Glu Asp Asp Leu Ser Phe Gln Ala Thr Phe Ile Arg Ala Cys Glu
                100                 105                 110

Glu Ala Gly Ile Ser Ala Glu Ala Ile Asp Pro Gln Gln Ala Arg Ile
            115                 120                 125

Ile Glu Pro Ala Val Asn Pro Ala Leu Ile Gly Ala Val Lys Val Pro
        130                 135                 140

Asp Gly Thr Val Asp Pro Phe Arg Leu Thr Ala Ala Asn Met Leu Asp
145                 150                 155                 160

Ala Lys Glu His Gly Ala Val Ile Leu Thr Ala His Glu Val Thr Gly
                165                 170                 175

Leu Ile Arg Glu Gly Ala Thr Val Cys Gly Val Arg Val Arg Asn His
            180                 185                 190

Leu Thr Gly Glu Thr Gln Ala Leu His Ala Pro Val Val Asn Ala
        195                 200                 205

Ala Gly Ile Trp Gly Gln His Ile Ala Glu Tyr Ala Asp Leu Arg Ile
        210                 215                 220

Arg Met Phe Pro Ala Lys Gly Ser Leu Leu Ile Met Asp His Arg Ile
225                 230                 235                 240

Asn Gln His Val Ile Asn Arg Cys Arg Lys Pro Ser Asp Ala Asp Ile
                245                 250                 255

Leu Val Pro Gly Asp Thr Ile Ser Leu Ile Gly Thr Thr Ser Leu Arg
            260                 265                 270

Ile Asp Tyr Asn Glu Ile Asp Asp Asn Arg Val Thr Ala Glu Glu Val
        275                 280                 285

Asp Ile Leu Leu Arg Glu Gly Glu Lys Leu Ala Pro Val Met Ala Lys
290                 295                 300

Thr Arg Ile Leu Arg Ala Tyr Ser Gly Val Arg Pro Leu Val Ala Ser
305                 310                 315                 320

Asp Asp Asp Pro Ser Gly Arg Asn Leu Ser Arg Gly Ile Val Leu Leu
                325                 330                 335

Asp His Ala Glu Arg Asp Gly Leu Asp Gly Phe Ile Thr Ile Thr Gly
            340                 345                 350

Gly Lys Leu Met Thr Tyr Arg Leu Met Ala Glu Trp Ala Thr Asp Ala
        355                 360                 365

Val Cys Arg Lys Leu Gly Asn Thr Arg Pro Cys Thr Thr Ala Asp Leu
370                 375                 380
```

-continued

```
Ala Leu Pro Gly Ser Gln Glu Pro Ala Glu Val Thr Leu Arg Lys Val
385                 390                 395                 400

Ile Ser Leu Pro Ala Pro Leu Arg Gly Ser Ala Val Tyr Arg His Gly
                405                 410                 415

Asp Arg Thr Pro Ala Trp Leu Ser Glu Gly Arg Leu His Arg Ser Leu
            420                 425                 430

Val Cys Glu Cys Glu Ala Val Thr Ala Gly Val Gln Tyr Ala Val
        435                 440                 445

Glu Asn Leu Asn Val Asn Ser Leu Leu Asp Leu Arg Arg Arg Thr Arg
    450                 455                 460

Val Gly Met Gly Thr Cys Gln Gly Glu Leu Cys Ala Cys Arg Ala Ala
465                 470                 475                 480

Gly Leu Leu Gln Arg Phe Asn Val Thr Thr Ser Ala Gln Ser Ile Glu
                485                 490                 495

Gln Leu Ser Thr Phe Leu Asn Glu Arg Trp Lys Gly Val Gln Pro Ile
            500                 505                 510

Ala Trp Gly Asp Ala Leu Arg Glu Ser Glu Phe Thr Arg Trp Val Tyr
        515                 520                 525

Gln Gly Leu Cys Gly Leu Glu Lys Glu Gln Lys Asp Ala Leu
530                 535                 540
```

(2) INFORMATION FOR SEQ ID NO:17:

(i) SEQUENCE CHARACTERISTICS:
        (A) LENGTH: 250 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: GPP2

(xi) SEQUENCE DESCRIPTION: SEQ ID NO:17:

```
Met Gly Leu Thr Thr Lys Pro Leu Ser Leu Lys Val Asn Ala Ala Leu
1               5                   10                  15

Phe Asp Val Asp Gly Thr Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
                100                 105                 110

Val Ala Thr Ser Gly Thr Arg Asp Met Ala Gln Lys Trp Phe Glu His
            115                 120                 125

Leu Gly Ile Arg Arg Pro Lys Tyr Phe Ile Thr Ala Asn Asp Val Lys
        130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175
```

-continued

```
Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250
```

(2) INFORMATION FOR SEQ ID NO:18:

(i) SEQUENCE CHARACTERISTICS:
        (A) LENGTH: 709 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: GUT1

(xi) SEQUENCE DESCRIPTION: SEQ ID NO:18:

```
Met Phe Pro Ser Leu Phe Arg Leu Val Val Phe Ser Lys Arg Tyr Ile
1               5                   10                  15

Phe Arg Ser Ser Gln Arg Leu Tyr Thr Ser Leu Lys Gln Glu Gln Ser
            20                  25                  30

Arg Met Ser Lys Ile Met Glu Asp Leu Arg Ser Asp Tyr Val Pro Leu
        35                  40                  45

Ile Ala Ser Ile Asp Val Gly Thr Thr Ser Ser Arg Cys Ile Leu Phe
    50                  55                  60

Asn Arg Trp Gly Gln Asp Val Ser Lys His Gln Ile Glu Tyr Ser Thr
65                  70                  75                  80

Ser Ala Ser Lys Gly Lys Ile Gly Val Ser Gly Leu Arg Arg Pro Ser
                85                  90                  95

Thr Ala Pro Ala Arg Glu Thr Pro Asn Ala Gly Asp Ile Lys Thr Ser
            100                 105                 110

Gly Lys Pro Ile Phe Ser Ala Glu Gly Tyr Ala Ile Gln Glu Thr Lys
        115                 120                 125

Phe Leu Lys Ile Glu Glu Leu Asp Leu Asp Phe His Asn Glu Pro Thr
    130                 135                 140

Leu Lys Phe Pro Lys Pro Gly Trp Val Glu Cys His Pro Gln Lys Leu
145                 150                 155                 160

Leu Val Asn Val Val Gln Cys Leu Ala Ser Ser Leu Leu Ser Leu Gln
                165                 170                 175

Thr Ile Asn Ser Glu Arg Val Ala Asn Gly Leu Pro Pro Tyr Lys Val
            180                 185                 190

Ile Cys Met Gly Ile Ala Asn Met Arg Glu Thr Thr Ile Leu Trp Ser
        195                 200                 205

Arg Arg Thr Gly Lys Pro Ile Val Asn Tyr Gly Ile Val Trp Asn Asp
    210                 215                 220

Thr Arg Thr Ile Lys Ile Val Arg Asp Lys Trp Gln Asn Thr Ser Val
225                 230                 235                 240

Asp Arg Gln Leu Gln Leu Arg Gln Lys Thr Gly Leu Pro Leu Leu Ser
                245                 250                 255
```

-continued

```
Thr Tyr Phe Ser Cys Ser Lys Leu Arg Trp Phe Leu Asp Asn Glu Pro
            260                 265                 270

Leu Cys Thr Lys Ala Tyr Glu Glu Asn Asp Leu Met Phe Gly Thr Val
            275                 280                 285

Asp Thr Trp Leu Ile Tyr Gln Leu Thr Lys Gln Lys Ala Phe Val Ser
            290                 295                 300

Asp Val Thr Asn Ala Ser Arg Thr Gly Phe Met Asn Leu Ser Thr Leu
305                 310                 315                 320

Lys Tyr Asp Asn Glu Leu Leu Glu Phe Trp Gly Ile Asp Lys Asn Leu
                    325                 330                 335

Ile His Met Pro Glu Ile Val Ser Ser Gln Tyr Tyr Gly Asp Phe
                340                 345                 350

Gly Ile Pro Asp Trp Ile Met Glu Lys Leu His Asp Ser Pro Lys Thr
            355                 360                 365

Val Leu Arg Asp Leu Val Lys Arg Asn Leu Pro Ile Gln Gly Cys Leu
        370                 375                 380

Gly Asp Gln Ser Ala Ser Met Val Gly Gln Leu Ala Tyr Lys Pro Gly
385                 390                 395                 400

Ala Ala Lys Cys Thr Tyr Gly Thr Gly Cys Phe Leu Leu Tyr Asn Thr
                405                 410                 415

Gly Thr Lys Lys Leu Ile Ser Gln His Gly Ala Leu Thr Thr Leu Ala
            420                 425                 430

Phe Trp Phe Pro His Leu Gln Glu Tyr Gly Gly Gln Lys Pro Glu Leu
            435                 440                 445

Ser Lys Pro His Phe Ala Leu Glu Gly Ser Val Ala Val Ala Gly Ala
        450                 455                 460

Val Val Gln Trp Leu Arg Asp Asn Leu Arg Leu Ile Asp Lys Ser Glu
465                 470                 475                 480

Asp Val Gly Pro Ile Ala Ser Thr Val Pro Asp Ser Gly Gly Val Val
                485                 490                 495

Phe Val Pro Ala Phe Ser Gly Leu Phe Ala Pro Tyr Trp Asp Pro Asp
            500                 505                 510

Ala Arg Ala Thr Ile Met Gly Met Ser Gln Phe Thr Thr Ala Ser His
            515                 520                 525

Ile Ala Arg Ala Ala Val Glu Gly Val Cys Phe Gln Ala Arg Ala Ile
        530                 535                 540

Leu Lys Ala Met Ser Ser Asp Ala Phe Gly Glu Gly Ser Lys Asp Arg
545                 550                 555                 560

Asp Phe Leu Glu Glu Ile Ser Asp Val Thr Tyr Glu Lys Ser Pro Leu
                565                 570                 575

Ser Val Leu Ala Val Asp Gly Gly Met Ser Arg Ser Asn Glu Val Met
            580                 585                 590

Gln Ile Gln Ala Asp Ile Leu Gly Pro Cys Val Lys Val Arg Arg Ser
            595                 600                 605

Pro Thr Ala Glu Cys Thr Ala Leu Gly Ala Ala Ile Ala Ala Asn Met
        610                 615                 620

Ala Phe Lys Asp Val Asn Glu Arg Pro Leu Trp Lys Asp Leu His Asp
625                 630                 635                 640

Val Lys Lys Trp Val Phe Tyr Asn Gly Met Glu Lys Asn Glu Gln Ile
                645                 650                 655

Ser Pro Glu Ala His Pro Asn Leu Lys Ile Phe Arg Ser Glu Ser Asp
            660                 665                 670

Asp Ala Glu Arg Arg Lys His Trp Lys Tyr Trp Glu Val Ala Val Glu
```

```
                   675                 680                 685
Arg Ser Lys Gly Trp Leu Lys Asp Ile Glu Gly Glu His Glu Gln Val
        690                 695                 700
Leu Glu Asn Phe Gln
705
```

(2) INFORMATION FOR SEQ ID NO:19:

(i) SEQUENCE CHARACTERISTICS:
  (A) LENGTH: 12145 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (A) ORGANISM: PHK28-26

(xi) SEQUENCE DESCRIPTION: SEQ ID NO:19:

| | | | | | |
|---|---|---|---|---|---|
| GTCGACCACC | ACGGTGGTGA | CTTTAATGCC | GCTCTCATGC | AGCAGCTCGG | TGGCGGTCTC | 60 |
| AAAATTCAGG | ATGTCGCCGG | TATAGTTTTT | GATAATCAGC | AAGACGCCTT | CGCCGCCGTC | 120 |
| AATTTGCATC | GCGCATTCAA | ACATTTTGTC | CGGCGTCGGC | GAGGTGAATA | TTTCCCCCGG | 180 |
| ACAGGCGCCG | GAGAGCATGC | CCTGGCCGAT | ATAGCCGCAG | TGCATCGGTT | CATGTCCGCT | 240 |
| GCCGCCGCCG | GAGAGCAGGG | CCACCTTGCC | AGCCACCGGC | GCGTCGGTGC | GGGTCACATA | 300 |
| CAGCGGGTCC | TGATGCAGGG | TCAGCTGCGG | ATGGGCTTTA | GCCAGCCCCT | GTAATTGTTC | 360 |
| ATTCAGTACA | TCTTCAACAC | GGTTAATCAG | CTTTTTCATT | ATTCAGTGCT | CCGTTGGAGA | 420 |
| AGGTTCGATG | CCGCCTCTCT | GCTGGCGGAG | GCGGTCATCG | CGTAGGGGTA | TCGTCTGACG | 480 |
| GTGGAGCGTG | CCTGGCGATA | TGATGATTCT | GGCTGAGCGG | ACGAAAAAAA | GAATGCCCCG | 540 |
| ACGATCGGGT | TTCATTACGA | ACATTGCTT | CCTGATTTTG | TTTCTTTATG | GAACGTTTTT | 600 |
| GCTGAGGATA | TGGTGAAAAT | GCGAGCTGGC | GCGCTTTTTT | TCTTCTGCCA | TAAGCGGCGG | 660 |
| TCAGGATAGC | CGGCGAAGCG | GGTGGGAAAA | AATTTTTTGC | TGATTTTCTG | CCGACTGCGG | 720 |
| GAGAAAAGGC | GGTCAAACAC | GGAGGATTGT | AAGGGCATTA | TGCGGCAAAG | GAGCGGATCG | 780 |
| GGATCGCAAT | CCTGACAGAG | ACTAGGGTTT | TTTGTTCCAA | TATGGAACGT | AAAAAATTAA | 840 |
| CCTGTGTTTC | ATATCAGAAC | AAAAAGGCGA | AGATTTTTT | TGTTCCCTGC | CGGCCCTACA | 900 |
| GTGATCGCAC | TGCTCCGGTA | CGCTCCGTTC | AGGCCGCGCT | TCACTGGCCG | GCGCGGATAA | 960 |
| CGCCAGGGCT | CATCATGTCT | ACATGCGCAC | TTATTTGAGG | GTGAAAGGAA | TGCTAAAAGT | 1020 |
| TATTCAATCT | CCAGCCAAAT | ATCTTCAGGG | TCCTGATGCT | GCTGTTCTGT | TCGGTCAATA | 1080 |
| TGCCAAAAAC | CTGGCGGAGA | GCTTCTTCGT | CATCGCTGAC | GATTTCGTAA | TGAAGCTGGC | 1140 |
| GGGAGAGAAA | GTGGTGAATG | CCTGCAGAG | CCACGATATT | CGCTGCCATG | CGGAACGGTT | 1200 |
| TAACGGCGAA | TGCAGCCATG | CGGAAATCAA | CCGTCTGATG | GCGATTTTGC | AAAAACAGGG | 1260 |
| CTGCCGCGGC | GTGGTCGGGA | TCGGCGGTGG | TAAAACCCTC | GATACCGCGA | AGGCGATCGG | 1320 |
| TTACTACCAG | AAGCTGCCGG | TGGTGGTGAT | CCCGACCATC | GCCTCGACCG | ATGCGCCAAC | 1380 |
| CAGCGCGCTG | TCGGTGATCT | ACACCGAAGC | GGGCGAGTTT | GAAGAGTATC | TGATCTATCC | 1440 |
| GAAAAACCCG | GATATGGTGG | TGATGGACAC | GGCGATTATC | GCCAAAGCGC | CGGTACGCCT | 1500 |
| GCTGGTCTCC | GGCATGGGCG | ATGCGCTCTC | CACCTGGTTC | GAGGCCAAAG | CTTGCTACGA | 1560 |
| TGCGCGCGCC | ACCAGCATGG | CCGGAGGACA | GTCCACCGAG | GCGGCGCTGA | GCCTCGCCCG | 1620 |
| CCTGTGCTAT | GATACGCTGC | TGGCGGAGGG | CGAAAAGGCC | CGTCTGGCGG | CGCAGGCCGG | 1680 |

```
GGTAGTGACC GAAGCGCTGG AGCGCATCAT CGAGGCGAAC ACTTACCTCA GCGGCATTGG    1740

CTTTGAAAGC AGTGGCCTGG CCGCTGCCCA TGCAATCCAC AACGGTTTCA CCATTCTTGA    1800

AGAGTGCCAT CACCTGTATC ACGGTGAGAA AGTGGCCTTC GGTACCCTGG CGCAGCTGGT    1860

GCTGCAGAAC AGCCCGATGG ACGAGATTGA AACGGTGCAG GGCTTCTGCC AGCGCGTCGG    1920

CCTGCCGGTG ACGCTCGCGC AGATGGGCGT CAAAGAGGGG ATCGACGAGA AAATCGCCGC    1980

GGTGGCGAAA GCTACCTGCG CGGAAGGGGA AACCATCCAT AATATGCCGT TTGCGGTGAC    2040

CCCGGAGAGC GTCCATGCCG CTATCCTCAC CGCCGATCTG TTAGGCCAGC AGTGGCTGGC    2100

GCGTTAATTC GCGGTGGCTA AACCGCTGGC CCAGGTCAGC GGTTTTTCTT TCTCCCCTCC    2160

GGCAGTCGCT GCCGGAGGGG TTCTCTATGG TACAACGCGG AAAAGGATAT GACTGTTCAG    2220

ACTCAGGATA CCGGGAAGGC GGTCTCTTCC GTCATTGCCC AGTCATGGCA CCGCTGCAGC    2280

AAGTTTATGC AGCGCGAAAC CTGGCAAACG CCGCACCAGG CCCAGGGCCT GACCTTCGAC    2340

TCCATCTGTC GGCGTAAAAC CGCGCTGCTC ACCATCGGCC AGGCGGCGCT GGAAGACGCC    2400

TGGGAGTTTA TGGACGGCCG CCCCTGCGCG CTGTTTATTC TTGATGAGTC CGCCTGCATC    2460

CTGAGCCGTT GCGGCGAGCC GCAAACCCTG GCCCAGCTGG CTGCCCTGGG ATTTCGCGAC    2520

GGCAGCTATT GTGCGGAGAG CATTATCGGC ACCTGCGCGC TGTCGCTGGC CGCGATGCAG    2580

GGCCAGCCGA TCAACACCGC CGGCGATCGG CATTTTAAGC AGGCGCTACA GCCATGGAGT    2640

TTTTGCTCGA CGCCGGTGTT TGATAACCAC GGGCGGCTGT TCGGCTCTAT CTCGCTTTGC    2700

TGTCTGGTCG AGCACCAGTC CAGCGCCGAC CTCTCCCTGA CGCTGGCCAT CGCCCGCGAG    2760

GTGGGTAACT CCCTGCTTAC CGACAGCCTG CTGGCGGAAT CCAACCGTCA CCTCAATCAG    2820

ATGTACGGCC TGCTGGAGAG CATGGACGAT GGGGTGATGG CGTGGAACGA ACAGGGCGTG    2880

CTGCAGTTTC TCAATGTTCA GGCGGCGAGA CTGCTGCATC TTGATGCTCA GGCCAGCCAG    2940

GGGAAAAATA TCGCCGATCT GGTGACCCTC CCGGCGCTGC TGCGCCGCGC CATCAAACAC    3000

GCCCGCGGCC TGAATCACGT CGAAGTCACC TTTGAAAGTC AGCATCAGTT TGTCGATGCG    3060

GTGATCACCT TAAAACCGAT TGTCGAGGCG CAAGGCAACA GTTTTATTCT GCTGCTGCAT    3120

CCGGTGGAGC AGATGCGGCA GCTGATGACC AGCCAGCTCG GTAAAGTCAG CCACACCTTT    3180

GAGCAGATGT CTGCCGACGA TCCGGAAACC CGACGCCTGA TCCACTTTGG CCGCCAGGCG    3240

GCGCGCGGCG GCTTCCCGGT GCTACTGTGC GGCGAAGAGG GGGTCGGGAA AGAGCTGCTG    3300

AGCCAGGCTA TTCACAATGA AAGCGAACGG GCGGGCGGCC CCTACATCTC CGTCAACTGC    3360

CAGCTATATG CCGACAGCGT GCTGGGCCAG GACTTTATGG GCAGCGCCCC TACCGACGAT    3420

GAAAATGGTC GCCTGAGCCG CCTTGAGCTG GCCAACGGCG GCACCCTGTT TCTGGAAAAG    3480

ATCGAGTATC TGGCGCCGGA GCTGCAGTCG GCTCTGCTGC AGGTGATTAA GCAGGGCGTG    3540

CTCACCCGCC TCGACGCCCG GCGCCTGATC CCGGTGGATG TGAAGGTGAT TGCCACCACC    3600

ACCGTCGATC TGGCCAATCT GGTGGAACAG AACCGCTTTA GCCGCCAGCT GTACTATCGG    3660

CTGCACTCCT TTGAGATCGT CATCCCGCCG CTGCGCGCCC GACGCAACAG TATTCCGTCG    3720

CTGGTGCATA ACCGGTTGAA GAGCCTGGAG AAGCGTTTCT CTTCGCGACT GAAAGTGGAC    3780

GATGACGCGC TGGCACAGCT GGTGGCCTAC TCGTGGCCGG GGAATGATTT TGAGCTCAAC    3840

AGCGTCATTG AGAATATCGC CATCAGCAGC GACAACGGCC ACATTCGCCT GAGTAATCTG    3900

CCGGAATATC TCTTTTCCGA GCGGCCGGGC GGGGATAGCG CGTCATCGCT GCTGCCGGCC    3960

AGCCTGACTT TTAGCGCCAT CGAAAAGGAA GCTATTATTC ACGCCGCCCG GGTGACCAGC    4020
```

```
GGGCGGGTGC AGGAGATGTC GCAGCTGCTC AATATCGGCC GCACCACCCT GTGGCGCAAA    4080

ATGAAGCAGT ACGATATTGA CGCCAGCCAG TTCAAGCGCA AGCATCAGGC CTAGTCTCTT    4140

CGATTCGCGC CATGGAGAAC AGGGCATCCG ACAGGCGATT GCTGTAGCGT TTGAGCGCGT    4200

CGCGCAGCGG ATGCGCGCGG TCCATGGCCG TCAGCAGGCG TTCGAGCCGA CGGGACTGGG    4260

TGCGCGCCAC GTGCAGCTGG GCAGAGGCGA GATTCCTCCC CGGGATCACG AACTGTTTTA    4320

ACGGGCCGCT CTCGGCCATA TTGCGGTCGA TAAGCCGCTC CAGGGCGGTG ATCTCCTCTT    4380

CGCCGATCGT CTGGCTCAGG CGGGTCAGGC CCCGCGCATC GCTGGCCAGT TCAGCCCCCA    4440

GCACGAACAG CGTCTGCTGA ATATGGTGCA GGCTTTCCCG CAGCCCGGCG TCGCGGGTCG    4500

TGGCGTAGCA GACGCCCAGC TGGGATATCA GTTCATCGAC GGTGCCGTAG GCCTCGACGC    4560

GAATATGGTC TTTCTCGATG CGGCTGCCGC CGTACAGGGC GGTGGTGCCT TTATCCCCGG    4620

TGCGGGTATA GATACGATAC ATTCAGTTTC TCTCACTTAA CGGCAGGACT TTAACCAGCT    4680

GCCCGGCGTT GGCGCCGAGC GTACGCAGTT GATCGTCGCT ATCGGTGACG TGTCCGGTAG    4740

CCAGCGGCGC GTCCGCCGGC AGCTGGGCAT GAGTGAGGGC TATCTCGCCG GACGCGCTGA    4800

GCCCGATACC CACCCGCAGG GGCGAGCTTC TGGCCGCCAG GGCGCCCAGC GCAGCGGCGT    4860

CACCGCCTCC GTCATAGGTT ATGGTCTGGC AGGGGACCCC CTGCTCCTCC AGCCCCCAGC    4920

ACAGCTCATT GATGGCGCCG GCATGGTGCC CGCGCGGATC GTAAACAGG  CGTACGCCTG    4980

GCGGTGAAAG CGACATGACG GTCCCCTCGT TAACACTCAG AATGCCTGGC GGAAAATCGC    5040

GGCAATCTCC TGCTCGTTGC CTTTACGCGG GTTCGAGAAC GCATTGCCGT CTTTTAGAGC    5100

CATCTCCGCC ATGTAGGGGA AGTCGGCCTC TTTTACCCCC AGATCGCGCA GATGCTGCGG    5160

AATACCGATA TCCATCGACA GACGCGTGAT AGCGGCGATG GCTTTTTCCG CCGCGTCGAG    5220

AGTGGACAGT CCGGTGATAT TTTCGCCCAT CAGTTCAGCG ATATCGGCGA ATTTCTCCGG    5280

GTTGGCGATC AGGTTGTAGC GCGCCACATG CGGCAGCAGG ACAGCGTTGG CCACGCCGTG    5340

CGGCATGTCG TACAGGCCGC CCAGCTGGTG CGCCATGGCG TGCACGTAGC CGAGGTTGGC    5400

GTTATTGAAA GCCATCCCGG CCAGCAGAGA AGCATAGGCC ATGTTTTCCC GCGCCTGCAG    5460

ATTGCTGCCG AGGGCCACGG CCTGGCGCAG GTTGCGGGCG ATGAGGCGGA TCGCCTGCAT    5520

GGCGGCGGCG TCCGTCACCG GGTTAGCGTC TTTGGAGATA TAGGCCTCTA CGGCGTGGGT    5580

CAGGGCATCC ATCCCGGTCG CCGCGGTCAG GGCGGCCGGT TTACCGATCA TCAGCAGTGG    5640

ATCGTTGATA GAGACCGACG GCAGTTTGCG CCAGCTGACG ATCACAAACT TCACTTTGGT    5700

TTCGGTGTTG GTCAGGACGC AGTGGCGGGT GACCTCGCTG GCGGTGCCGG CGGTGGTATT    5760

GACCGCGACG ATAGGCGGCA GCGGGTTGGT CAGGGTCTCG ATTCCGGCAT ACTGGTACAG    5820

ATCGCCCTCA TGGGTGGCGG CGATGCCGAT GCCTTTGCCG CAATCGTGCG GGCTGCCGCC    5880

GCCCACGGTG ACGATGATGT CGCACTGTTC GCGGCGAAAC ACGGCGAGGC CGTCGCGCAC    5940

GTTGGTGTCT TTCGGGTTCG GCTCGACGCC GTCAAAGATC GCCACCTCGA TCCCGGCCTC    6000

CCGCAGATAA TGCAGGGTTT TGTCCACCGC GCCATCTTTA ATTGCCCGCA GGCCTTTGTC    6060

GGTGACCAGC AGGGCTTTTT TCCCCCCCAG CAGCTGGCAG CGTTCGCCGA CTACGGAAAT    6120

GGCGTTGGGC CCAAAAAAGT TAACGTTTGG CACCAGATAA TCAAACATAC GATAGCTCAT    6180

AATATACCTT CTCGCTTCAG GTTATAATGC GGAAAAACAA TCCAGGGCGC ACTGGGCTAA    6240

TAATTGATCC TGCTCGACCG TACCGCCGCT AACGCCGACG GCGCCAATTA CCTGCTCATT    6300

AAAAATAACT GGCAGGCCGC CGCCAAAAAT AATAATTCGC TGTTGGTTGG TTAGCTGCAG    6360

ACCGTACAGA GATTGTCCTG GCTGGACCGC TGACGTAATT TCATGGGTAC CTTGCTTCAG    6420
```

```
GCTGCAGGCG CTCCAGGCTT TATTCAGGGA AATATCGCAG CTGGAGACGA AGGCCTCGTC    6480

CATCCGCTGG ATAAGCAGCG TGTTGCCTCC GCGGTCAACT ACGGAAAACA CCACCGCCAC    6540

GTTGATCTCA GTGGCTTTTT TTTCCACCGC CGCCGCCATT TGCTGGGCGG CGGCCAGGGT    6600

GATTGTCTGA ACTTGTTGGC TCTTGTTCAT CATTCTCTCC CGCACCAGGA TAACGCTGGC    6660

GCGAATAGTC AGTAGGGGGC GATAGTAAAA AACTATTACC ATTCGGTTGG CTTGCTTTAT    6720

TTTTGTCAGC GTTATTTTGT CGCCCGCCAT GATTTAGTCA ATAGGGTTAA AATAGCGTCG    6780

GAAAAACGTA ATTAAGGGCG TTTTTTATTA ATTGATTTAT ATCATTGCGG GCGATCACAT    6840

TTTTTATTTT TGCCGCCGGA GTAAAGTTTC ATAGTGAAAC TGTCGGTAGA TTTCGTGTGC    6900

CAAATTGAAA CGAAATTAAA TTTATTTTTT TCACCACTGG CTCATTTAAA GTTCCGCTAT    6960

TGCCGGTAAT GGCCGGGCGG CAACGACGCT GGCCCGGCGT ATTCGCTACC GTCTGCGGAT    7020

TTCACCTTTT GAGCCGATGA ACAATGAAAA GATCAAAACG ATTTGCAGTA CTGGCCCAGC    7080

GCCCCGTCAA TCAGGACGGG CTGATTGGCG AGTGGCCTGA AGAGGGGCTG ATCGCCATGG    7140

ACAGCCCCTT TGACCCGGTC TCTTCAGTAA AAGTGGACAA CGGTCTGATC GTCGAACTGG    7200

ACGGCAAACG CCGGGACCAG TTTGACATGA TCGACCGATT TATCGCCGAT TACGCGATCA    7260

ACGTTGAGCG CACAGAGCAG GCAATGCGCC TGGAGGCGGT GGAAATAGCC CGTATGCTGG    7320

TGGATATTCA CGTCAGCCGG GAGGAGATCA TTGCCATCAC TACCGCCATC ACGCCGGCCA    7380

AAGCGGTCGA GGTGATGGCG CAGATGAACG TGGTGGAGAT GATGATGCG CTGCAGAAGA    7440

TGCGTGCCCG CCGGACCCCC TCCAACCAGT GCCACGTCAC CAATCTCAAA GATAATCCGG    7500

TGCAGATTGC CGCTGACGCC GCCGAGGCCG GGATCCGCGG CTTCTCAGAA CAGGAGACCA    7560

CGGTCGGTAT CGCGCGCTAC GCGCCGTTTA ACGCCCTGGC GCTGTTGGTC GGTTCGCAGT    7620

GCGGCCGCCC CGGCGTGTTG ACGCAGTGCT CGGTGGAAGA GGCCACCGAG CTGGAGCTGG    7680

GCATGCGTGG CTTAACCAGC TACGCCGAGA CGGTGTCGGT CTACGGCACC GAAGCGGTAT    7740

TTACCGACGG CGATGATACG CCGTGGTCAA AGGCGTTCCT CGCCTCGGCC TACGCCTCCC    7800

GCGGGTTGAA AATGCGCTAC ACCTCCGGCA CCGGATCCGA AGCGCTGATG GGCTATTCGG    7860

AGAGCAAGTC GATGCTCTAC CTCGAATCGC GCTGCATCTT CATTACTAAA GGCGCCGGGG    7920

TTCAGGGACT GCAAAACGGC GCGGTGAGCT GTATCGGCAT GACCGGCGCT GTGCCGTCGG    7980

GCATTCGGGC GGTGCTGGCG GAAAACCTGA TCGCCTCTAT GCTCGACCTC GAAGTGGCGT    8040

CCGCCAACGA CCAGACTTTC TCCCACTCGG ATATTCGCCG CACCGCGCGC ACCCTGATGC    8100

AGATGCTGCC GGGCACCGAC TTTATTTTCT CCGGCTACAG CGCGGTGCCG AACTACGACA    8160

ACATGTTCGC CGGCTCGAAC TTCGATGCGG AAGATTTTGA TGATTACAAC ATCCTGCAGC    8220

GTGACCTGAT GGTTGACGGC GGCCTGCGTC CGGTGACCGA GGCGGAAACC ATTGCCATTC    8280

GCCAGAAAGC GGCGCGGGCG ATCCAGGCGG TTTTCCGCGA GCTGGGGCTG CCGCCAATCG    8340

CCGACGAGGA GGTGGAGGCC GCCACCTACG CGCACGGCAG CAACGAGATG CCGCCGCGTA    8400

ACGTGGTGGA GGATCTGAGT GCGGTGGAAG AGATGATGAA GCGCAACATC ACCGGCCTCG    8460

ATATTGTCGG CGCGCTGAGC CGCAGCGGCT TTGAGGATAT CGCCAGCAAT ATTCTCAATA    8520

TGCTGCGCCA GCGGGTCACC GGCGATTACC TGCAGACCTC GGCCATTCTC GATCGGCAGT    8580

TCGAGGTGGT GAGTGCGGTC AACGACATCA ATGACTATCA GGGGCCGGGC ACCGGCTATC    8640

GCATCTCTGC CGAACGCTGG GCGGAGATCA AAAATATTCC GGGCGTGGTT CAGCCCGACA    8700

CCATTGAATA AGGCGGTATT CCTGTGCAAC AGACAACCCA AATTCAGCCC TCTTTTACCC    8760
```

-continued

```
TGAAAACCCG CGAGGGCGGG GTAGCTTCTG CCGATGAACG CGCCGATGAA GTGGTGATCG    8820
GCGTCGGCCC TGCCTTCGAT AAACACCAGC ATCACACTCT GATCGATATG CCCCATGGCG    8880
CGATCCTCAA AGAGCTGATT GCCGGGGTGG AAGAAGAGGG GCTTCACGCC CGGGTGGTGC    8940
GCATTCTGCG CACGTCCGAC GTCTCCTTTA TGGCCTGGGA TGCGGCCAAC CTGAGCGGCT    9000
CGGGGATCGG CATCGGTATC CAGTCGAAGG GGACCACGGT CATCCATCAG CGCGATCTGC    9060
TGCCGCTCAG CAACCTGGAG CTGTTCTCCC AGGCGCCGCT GCTGACGCTG GAGACCTACC    9120
GGCAGATTGG CAAAAACGCT GCGCGCTATG CGCGCAAAGA GTCACCTTCG CCGGTGCCGG    9180
TGGTGAACGA TCAGATGGTG CGGCCGAAAT TTATGGCCAA AGCCGCGCTA TTTCATATCA    9240
AAGAGACCAA ACATGTGGTG CAGGACGCCG AGCCCGTCAC CCTGCACATC GACTTAGTAA    9300
GGGAGTGACC ATGAGCGAGA AAACCATGCG CGTGCAGGAT TATCCGTTAG CCACCCGCTG    9360
CCCGGAGCAT ATCCTGACGC CTACCGGCAA ACCATTGACC GATATTACCC TCGAGAAGGT    9420
GCTCTCTGGC GAGGTGGGCC CGCAGGATGT GCGGATCTCC CGCCAGACCC TTGAGTACCA    9480
GGCGCAGATT GCCGAGCAGA TGCAGCGCCA TGCGGTGGCG CGCAATTTCC GCCGCGCGGC    9540
GGAGCTTATC GCCATTCCTG ACGAGCGCAT TCTGGCTATC TATAACGCGC TGCGCCCGTT    9600
CCGCTCCTCG CAGGCGGAGC TGCTGGCGAT CGCCGACGAG CTGGAGCACA CCTGGCATGC    9660
GACAGTGAAT GCCGCCTTTG TCCGGGAGTC GGCGGAAGTG TATCAGCAGC GGCATAAGCT    9720
GCGTAAAGGA AGCTAAGCGG AGGTCAGCAT GCCGTTAATA GCCGGGATTG ATATCGGCAA    9780
CGCCACCACC GAGGTGGCGC TGGCGTCCGA CTACCCGCAG GCGAGGGCGT TTGTTGCCAG    9840
CGGGATCGTC GCGACGACGG GCATGAAAGG GACGCGGGAC AATATCGCCG GGACCCTCGC    9900
CGCGCTGGAG CAGGCCCTGG CGAAAACACC GTGGTCGATG AGCGATGTCT CTCGCATCTA    9960
TCTTAACGAA GCCGCGCCGG TGATTGGCGA TGTGGCGATG GAGACCATCA CCGAGACCAT   10020
TATCACCGAA TCGACCATGA TCGGTCATAA CCCGCAGACG CCGGGCGGGG TGGGCGTTGG   10080
CGTGGGGACG ACTATCGCCC TCGGGCGGCT GGCGACGCTG CCGGCGGCGC AGTATGCCGA   10140
GGGGTGGATC GTACTGATTG ACGACGCCGT CGATTTCCTT GACGCCGTGT GGTGGCTCAA   10200
TGAGGCGCTC GACCGGGGGA TCAACGTGGT GGCGGCGATC CTCAAAAAGG ACGACGGCGT   10260
GCTGGTGAAC AACCGCCTGC GTAAAACCCT GCCGGTGGTG GATGAAGTGA CGCTGCTGGA   10320
GCAGGTCCCC GAGGGGGTAA TGGCGGCGGT GGAAGTGGCC GCGCCGGGCC AGGTGGTGCG   10380
GATCCTGTCG AATCCCTACG GGATCGCCAC CTTCTTCGGG CTAAGCCCGG AAGAGACCCA   10440
GGCCATCGTC CCCATCGCCC GCGCCCTGAT TGGCAACCGT TCCGCGGTGG TGCTCAAGAC   10500
CCCGCAGGGG GATGTGCAGT CGCGGGTGAT CCCGGCGGGC AACCTCTACA TTAGCGGCGA   10560
AAAGCGCCGC GGAGAGGCCG ATGTCGCCGA GGGCGCGGAA GCCATCATGC AGGCGATGAG   10620
CGCCTGCGCT CCGGTACGCG ACATCCGCGG CGAACCGGGC ACCCACGCCG GCGGCATGCT   10680
TGAGCGGGTG CGCAAGGTAA TGGCGTCCCT GACCGGCCAT GAGATGAGCG CGATATACAT   10740
CCAGGATCTG CTGGCGGTGG ATACGTTTAT TCCGCGCAAG GTGCAGGGCG GGATGGCCGG   10800
CGAGTGCGCC ATGGAGAATG CCGTCGGGAT GGCGGCGATG GTGAAAGCGG ATCGTCTGCA   10860
AATGCAGGTT ATCGCCCGCG AACTGAGCGC CCGACTGCAG ACCGAGGTGG TGGTGGGCGG   10920
CGTGGAGGCC AACATGGCCA TCGCCGGGGC GTTAACCACT CCCGGCTGTG CGGCGCCGCT   10980
GGCGATCCTC GACCTCGGCG CCGGCTCGAC GGATGCGGCG ATCGTCAACG CGGAGGGGCA   11040
GATAACGGCG GTCCATCTCG CCGGGGCGGG GAATATGGTC AGCCTGTTGA TTAAAACCGA   11100
GCTGGGCCTC GAGGATCTTT CGCTGGCGGA AGCGATAAAA AAATACCCGC TGGCCAAAGT   11160
```

```
GGAAAGCCTG TTCAGTATTC GTCACGAGAA TGGCGCGGTG GAGTTCTTTC GGGAAGCCCT      11220

CAGCCCGGCG GTGTTCGCCA AAGTGGTGTA CATCAAGGAG GGCGAACTGG TGCCGATCGA      11280

TAACGCCAGC CCGCTGGAAA AAATTCGTCT CGTGCGCCGG CAGGCGAAAG AGAAAGTGTT      11340

TGTCACCAAC TGCCTGCGCG CGCTGCGCCA GGTCTCACCC GGCGGTTCCA TTCGCGATAT      11400

CGCCTTTGTG GTGCTGGTGG GCGGCTCATC GCTGGACTTT GAGATCCCGC AGCTTATCAC      11460

GGAAGCCTTG TCGCACTATG GCGTGGTCGC CGGGCAGGGC AATATTCGGG GAACAGAAGG      11520

GCCGCGCAAT GCGGTCGCCA CCGGGCTGCT ACTGGCCGGT CAGGCGAATT AAACGGGCGC      11580

TCGCGCCAGC CTCTCTCTTT AACGTGCTAT TTCAGGATGC CGATAATGAA CCAGACTTCT      11640

ACCTTAACCG GGCAGTGCGT GGCCGAGTTT CTTGGCACCG GATTGCTCAT TTTCTTCGGC      11700

GCGGGCTGCG TCGCTGCGCT GCGGGTCGCC GGGGCCAGCT TTGGTCAGTG GGAGATCAGT      11760

ATTATCTGGG GCCTTGGCGT CGCCATGGCC ATCTACCTGA CGGCCGGTGT CTCCGGCGCG      11820

CACCTAAATC CGGCGGTGAC CATTGCCCTG TGGCTGTTCG CCTGTTTTGA ACGCCGCAAG      11880

GTGCTGCCGT TTATTGTTGC CCAGACGGCC GGGGCCTTCT GCGCCGCCGC GCTGGTGTAT      11940

GGGCTCTATC GCCAGCTGTT TCTCGATCTT GAACAGAGTC AGCATATCGT GCGCGGCACT      12000

GCCGCCAGTC TTAACCTGGC CGGGGTCTTT TCCACGTACC CGCATCCACA TATCACTTTT      12060

ATACAAGCGT TTGCCGTGGA GACCACCATC ACGGCAATCC TGATGGCGAT GATCATGGCC      12120

CTGACCGACG ACGGCAACGG AATTC                                           12145
```

(2) INFORMATION FOR SEQ ID NO:20:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
AGCTTAGGAG TCTAGAATAT TGAGCTCGAA TTCCCGGGCA TGCGGTACCG GATCCAGAAA      60

AAAGCCCGCA CCTGACAGTG CGGGCTTTTT TTTT                                 94
```

(2) INFORMATION FOR SEQ ID NO:21:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
GGAATTCAGA TCTCAGCAAT GAGCGAGAAA ACCATGC                              37
```

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GCTCTAGATT AGCTTCCTTT ACGCAGC                                                    27

(2) INFORMATION FOR SEQ ID NO:23:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:23:

GGCCAAGCTT AAGGAGGTTA ATTAAATGAA AAG                                              33

(2) INFORMATION FOR SEQ ID NO:24:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:24:

GCTCTAGATT ATTCAATGGT GTCGGG                                                     26

(2) INFORMATION FOR SEQ ID NO:25:

(i) SEQUENCE CHARACTERISTICS:
          (A) LENGTH: 42 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:25:

GCGCCGTCTA GAATTATGAG CTATCGTATG TTTGATTATC TG                                   42

(2) INFORMATION FOR SEQ ID NO:26:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:26:

TCTGATACGG GATCCTCAGA ATGCCTGGCG GAAAAT                                           36

(2) INFORMATION FOR SEQ ID NO:27:

(i) SEQUENCE CHARACTERISTICS:
          (A) LENGTH: 51 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:27:

GCGCGGATCC AGGAGTCTAG AATTATGGGA TTGACTACTA AACCTCTATC T                          51
```

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GATACGCCCG GGTTACCATT TCAACAGATC GTCCTT                     36

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

TCGACGAATT CAGGAGGA                                        18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CTAGTCCTCC TGAATTCG                                        18

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CTAGTAAGGA GGACAATTC                                    19

(2) INFORMATION FOR SEQ ID NO:32:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

CATGGAATTG TCCTCCTTA                                    19

(2) INFORMATION FOR SEQ ID NO:33:

(i) SEQUENCE CHARACTERISTICS:
        (A) LENGTH: 271 amino acids (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: GPP1

(xi) SEQUENCE DESCRIPTION: SEQ ID NO:33:

Met Lys Arg Phe Asn Val Leu Lys Tyr Ile Arg Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ile Ser Gln
            35                  40                  45

Pro Ala Ile Ala Ala Phe Trp Arg Asp Phe Gly Lys Asp Lys Pro Tyr
50                  55                  60

Phe Asp Ala Glu His Val Ile His Ile Ser His Gly Trp Arg Thr Tyr
65                  70                  75                  80

Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
                100                 105                 110

Glu Val Pro Gly Ala Val Lys Leu Cys Asn Ala Leu Asn Ala Leu Pro
            115                 120                 125

Lys Glu Lys Trp Ala Val Ala Thr Ser Gly Thr Arg Asp Met Ala Lys
130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
                165                 170                 175

Gly Arg Asn Gly Leu Gly Phe Pro Ile Asn Glu Gln Asp Pro Ser Lys
            180                 185                 190

Ser Lys Val Val Val Phe Glu Asp Ala Pro Ala Gly Ile Ala Ala Gly
            195                 200                 205

Lys Ala Ala Gly Cys Lys Ile Val Gly Ile Ala Thr Thr Phe Asp Leu
210                 215                 220

Asp Phe Leu Lys Glu Lys Gly Cys Asp Ile Ile Val Lys Asn His Glu
225                 230                 235                 240

Ser Ile Arg Val Gly Glu Tyr Asn Ala Glu Thr Asp Glu Val Glu Leu
                245                 250                 255

Ile Phe Asp Asp Tyr Leu Tyr Ala Lys Asp Asp Leu Leu Lys Trp
            260                 265                 270

(2) INFORMATION FOR SEQ ID NO:34:

(i) SEQUENCE CHARACTERISTICS:
        (A) LENGTH: 555 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: DHAB1

(xi) SEQUENCE DESCRIPTION: SEQ ID NO:34:

Met Lys Arg Ser Lys Arg Phe Ala Val Leu Ala Gln Arg Pro Val Asn

```
1               5                   10                  15
Gln Asp Gly Leu Ile Gly Glu Trp Pro Glu Glu Gly Leu Ile Ala Met
                    20                  25                  30

Asp Ser Pro Phe Asp Pro Val Ser Val Lys Val Asp Asn Gly Leu
            35                  40                  45

Ile Val Glu Leu Asp Gly Lys Arg Arg Asp Gln Phe Asp Met Ile Asp
        50                  55                  60

Arg Phe Ile Ala Asp Tyr Ala Ile Asn Val Glu Arg Thr Glu Gln Ala
65                      70                  75                  80

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
                100                 105                 110

Lys Ala Val Glu Val Met Ala Gln Met Asn Val Val Glu Met Met Met
                115                 120                 125

Ala Leu Gln Lys Met Arg Ala Arg Thr Pro Ser Asn Gln Cys His
130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Val Gly Ser Gln
                180                 185                 190

Cys Gly Arg Pro Gly Val Leu Thr Gln Cys Ser Val Glu Glu Ala Thr
                195                 200                 205

Glu Leu Glu Leu Gly Met Arg Gly Leu Thr Ser Tyr Ala Glu Thr Val
        210                 215                 220

Ser Val Tyr Gly Thr Glu Ala Val Phe Thr Asp Gly Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
                260                 265                 270

Glu Ser Lys Ser Met Leu Tyr Leu Glu Ser Arg Cys Ile Phe Ile Thr
                275                 280                 285

Lys Gly Ala Gly Val Gln Gly Leu Gln Asn Gly Ala Val Ser Cys Ile
290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
                340                 345                 350

Gln Met Leu Pro Gly Thr Asp Phe Ile Phe Ser Gly Tyr Ser Ala Val
                355                 360                 365

Pro Asn Tyr Asp Asn Met Phe Ala Gly Ser Asn Phe Asp Ala Glu Asp
            370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
                420                 425                 430
```

```
Ala Asp Glu Glu Val Glu Ala Ala Thr Tyr Ala His Gly Ser Asn Glu
    435                 440                 445

Met Pro Pro Arg Asn Val Val Glu Asp Leu Ser Ala Val Glu Glu Met
    450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
            515                 520                 525

Gly Thr Gly Tyr Arg Ile Ser Ala Glu Arg Trp Ala Glu Ile Lys Asn
    530                 535                 540

Ile Pro Gly Val Val Gln Pro Asp Thr Ile Glu
545                 550                 555

(2) INFORMATION FOR SEQ ID NO:35:

(i) SEQUENCE CHARACTERISTICS:
        (A) LENGTH:  194 amino acids
        (B) TYPE:  amino acid
        (C) STRANDEDNESS:  unknown
        (D) TOPOLOGY:  unknown (ii) MOLECULE TYPE:  protein (vi) ORIGINAL SOURCE:
        (A) ORGANISM:  DHAB2

(xi) SEQUENCE DESCRIPTION:  SEQ ID NO:35:

Met Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
                20                  25                  30

Gly Val Gly Pro Ala Phe Asp Lys His Gln His His Thr Leu Ile Asp
            35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
                100                 105                 110

Leu Pro Leu Ser Asn Leu Glu Leu Phe Ser Gln Ala Pro Leu Leu Thr
            115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Ile Asp Leu Val
            180                 185                 190

Arg Glu
```

(2) INFORMATION FOR SEQ ID NO:36:

(i) SEQUENCE CHARACTERISTICS:
        (A) LENGTH: 140 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: DHAB3

(xi) SEQUENCE DESCRIPTION: SEQ ID NO:36:

```
Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
                20                  25                  30

Thr Leu Glu Lys Val Leu Ser Gly Glu Val Gly Pro Gln Asp Val Arg
            35                  40                  45

Ile Ser Arg Gln Thr Leu Glu Tyr Gln Ala Gln Ile Ala Glu Gln Met
50                  55                  60

Gln His Ala Val Ala Arg Asn Phe Arg Arg Ala Ala Glu Leu Ile Ala
65                  70                  75                  80

Ile Pro Asp Glu Arg Ile Leu Ala Ile Tyr Asn Ala Leu Arg Pro Phe
                85                  90                  95

Arg Ser Ser Gln Ala Glu Leu Leu Ala Ile Ala Asp Glu Leu Glu His
            100                 105                 110

Thr Trp His Ala Thr Val Asn Ala Ala Phe Val Arg Glu Ser Ala Glu
        115                 120                 125

Val Tyr Gln Gln Arg His Lys Leu Arg Lys Gly Ser
        130                 135                 140
```

(2) INFORMATION FOR SEQ ID NO:37:

(i) SEQUENCE CHARACTERISTICS:
        (A) LENGTH: 387 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: DHAT (xi) SEQUENCE DESCRIPTION: SEQ ID NO:37:

```
Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
                20                  25                  30

Gly Lys Lys Ala Leu Leu Val Thr Asp Lys Gly Leu Arg Ala Ile Lys
            35                  40                  45

Asp Gly Ala Val Asp Lys Thr Leu His Tyr Leu Arg Glu Ala Gly Ile
        50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
            100                 105                 110
```

```
Ile Ala Ala Thr His Glu Gly Asp Leu Tyr Gln Tyr Ala Gly Ile Glu
        115                 120                 125

Thr Leu Thr Asn Pro Leu Pro Pro Ile Val Ala Val Asn Thr Thr Ala
130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Lys Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Met Gln Ala Ile
    210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Gln Glu Ile Ala Ala Ile Phe Arg
    370                 375                 380

Gln Ala Phe
385

(2) INFORMATION FOR SEQ ID NO:38:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:38:

GCGAATTCAT GAGCTATCGT ATGTTTG                                    27

(2) INFORMATION FOR SEQ ID NO:39:

(i) SEQUENCE CHARACTERISTICS:
        (A) LENGTH:  28 base pairs
        (B) TYPE:  nucleic acid
        (C) STRANDEDNESS:  single
        (D) TOPOLOGY:  linear
```

(ii) MOLECULE TYPE:  DNA (genomic)

(xi) SEQUENCE DESCRIPTION:  SEQ ID NO:39:

GCGAATTCAG AATGCCTGGC GGAAAATC                                        28

(2) INFORMATION FOR SEQ ID NO:40:

(i) SEQUENCE CHARACTERISTICS:
            (A) LENGTH:  28 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:40:

GGGAATTCAT GAGCGAGAAA ACCATGCG                                        28

(2) INFORMATION FOR SEQ ID NO:41:

(i) SEQUENCE CHARACTERISTICS:
            (A) LENGTH:  27 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:41:

GCGAATTCTT AGCTTCCTTT ACGCAGC                                         27

(2) INFORMATION FOR SEQ ID NO:42:

(i) SEQUENCE CHARACTERISTICS:
            (A) LENGTH:  30 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:42:

GCGAATTCAT GCAACAGACA ACCCAAATTC                                      30

(2) INFORMATION FOR SEQ ID NO:43:

(i) SEQUENCE CHARACTERISTICS:
            (A) LENGTH:  25 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:43:

GCGAATTCAC TCCCTTACTA AGTCG                                           25

(2) INFORMATION FOR SEQ ID NO:44:

(i) SEQUENCE CHARACTERISTICS:
            (A) LENGTH:  30 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:44:

```
GGGAATTCAT GAAAAGATCA AAACGATTTG                                              30

(2) INFORMATION FOR SEQ ID NO:45:

(i) SEQUENCE CHARACTERISTICS:
         (A) LENGTH:  29 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:45:

GCGAATTCTT ATTCAATGGT GTCGGGCTG                                               29

(2) INFORMATION FOR SEQ ID NO:46:

(i) SEQUENCE CHARACTERISTICS:
         (A) LENGTH:  34 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:46:

TTGATAATAT AACCATGGCT GCTGCTGCTG ATAG                                         34

(2) INFORMATION FOR SEQ ID NO:47:

(i) SEQUENCE CHARACTERISTICS:
         (A) LENGTH:  39 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:47:

GTATGATATG TTATCTTGGA TCCAATAAAT CTAATCTTC                                    39

(2) INFORMATION FOR SEQ ID NO:48:

(i) SEQUENCE CHARACTERISTICS:
         (A) LENGTH:  24 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:48:

CATGACTAGT AAGGAGGACA ATTC                                                    24

(2) INFORMATION FOR SEQ ID NO:49:

(i) SEQUENCE CHARACTERISTICS:
         (A) LENGTH:  24 base pairs
         (B) TYPE:  nucleic acid
         (C) STRANDEDNESS:  single
         (D) TOPOLOGY:  linear (ii) MOLECULE TYPE:  DNA (genomic)

(xi) SEQUENCE DESCRIPTION:  SEQ ID NO:49:

CATGGAATTG TCCTCCTTAC TAGT                                                    24

(2) INFORMATION FOR SEQ ID NO:50:
```

(i) SEQUENCE CHARACTERISTICS:
        (A) LENGTH: 94 base pairs
        (B) TYPE: nucleic acid
        (C) STRANDEDNESS: single
        (D) TOPOLOGY: linear (xi) SEQUENCE DESCRIPTION: SEQ ID NO:50:

AGCTTAGGAG TCTAGAATAT TGAGCTCGAA TTCCCGGGCA TGCGGTACCG GATCCAGAAA      60

AAAGCCCGCA CCTGACAGTG CGGGCTTTTT TTTT                                 94

(2) INFORMATION FOR SEQ ID NO:51:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:51:

GGAATTCAGA TCTCAGCAAT GAGCGAGAAA ACCATGC                              37

(2) INFORMATION FOR SEQ ID NO:52:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:52:

GCTCTAGATT AGCTTCCTTT ACGCAGC                                         27

(2) INFORMATION FOR SEQ ID NO:53:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:53:

GGCCAAGCTT AAGGAGGTTA ATTAAATGAA AAG                                  33

(2) INFORMATION FOR SEQ ID NO:54:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:54:

GCTCTAGATT ATTCAATGGT GTCGGG                                          26

(2) INFORMATION FOR SEQ ID NO:55:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:55:

GCGCCGTCTA GAATTATGAG CTATCGTATG TTTGATTATC TG                        42

(2) INFORMATION FOR SEQ ID NO:56:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:56:

```
TCTGATACGG GATCCTCAGA ATGCCTGGCG GAAAAT                              36
```

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:57:

```
TCGACGAATT CAGGAGGA                                                  18
```

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:58:

```
CTAGTCCTCC TGAATTCG                                                  18
```

(2) INFORMATION FOR SEQ ID NO:59:

(i) SEQUENCE CHARACTERISTICS:
        (A) LENGTH: 607 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:59:

```
Met Pro Leu Ile Ala Gly Ile Asp Ile Gly Asn Ala Thr Thr Glu Val
 1               5                  10                  15

Ala Leu Ala Ser Asp Tyr Pro Gln Ala Arg Ala Phe Val Ala Ser Gly
             20                  25                  30

Ile Val Ala Thr Thr Gly Met Lys Gly Thr Arg Asp Asn Ile Ala Gly
         35                  40                  45

Thr Leu Ala Ala Leu Glu Gln Ala Leu Ala Lys Thr Pro Trp Ser Met
     50                  55                  60

Ser Asp Val Ser Arg Ile Tyr Leu Asn Glu Ala Ala Pro Val Ile Gly
 65                  70                  75                  80

Asp Val Ala Met Glu Thr Ile Thr Glu Thr Ile Ile Thr Glu Ser Thr
                 85                  90                  95

Met Ile Gly His Asn Pro Gln Thr Pro Gly Gly Val Gly Val Gly Val
            100                 105                 110

Gly Thr Thr Ile Ala Leu Gly Arg Leu Ala Thr Leu Pro Ala Ala Gln
        115                 120                 125

Tyr Ala Glu Gly Trp Ile Val Leu Ile Asp Asp Ala Val Asp Phe Leu
    130                 135                 140

Asp Ala Val Trp Trp Leu Asn Glu Ala Leu Asp Arg Gly Ile Asn Val
```

```
                145                 150                 155                 160
        Val Ala Ala Ile Leu Lys Lys Asp Asp Gly Val Leu Val Asn Asn Arg
                        165                 170                 175

Leu Arg Lys Thr Leu Pro Val Val Asp Glu Val Thr Leu Leu Glu Gln
                        180                 185                 190

Val Pro Glu Gly Val Met Ala Ala Val Glu Val Ala Ala Pro Gly Gln
                        195                 200                 205

Val Val Arg Ile Leu Ser Asn Pro Tyr Gly Ile Ala Thr Phe Phe Gly
                210                 215                 220

Leu Ser Pro Glu Glu Thr Gln Ala Ile Val Pro Ile Ala Arg Ala Leu
        225                 230                 235                 240

Ile Gly Asn Arg Ser Ala Val Val Leu Lys Thr Pro Gln Gly Asp Val
                        245                 250                 255

Gln Ser Arg Val Ile Pro Ala Gly Asn Leu Tyr Ile Ser Gly Glu Lys
                        260                 265                 270

Arg Arg Gly Glu Ala Asp Val Ala Glu Gly Ala Glu Ala Ile Met Gln
                        275                 280                 285

Ala Met Ser Ala Cys Ala Pro Val Arg Asp Ile Arg Gly Glu Pro Gly
                290                 295                 300

Thr His Ala Gly Gly Met Leu Glu Arg Val Arg Lys Val Met Ala Ser
        305                 310                 315                 320

Leu Thr Gly His Glu Met Ser Ala Ile Tyr Ile Gln Asp Leu Leu Ala
                        325                 330                 335

Val Asp Thr Phe Ile Pro Arg Lys Val Gln Gly Gly Met Ala Gly Glu
                        340                 345                 350

Cys Ala Met Glu Asn Ala Val Gly Met Ala Ala Met Val Lys Ala Asp
                        355                 360                 365

Arg Leu Gln Met Gln Val Ile Ala Arg Glu Leu Ser Ala Arg Leu Gln
                370                 375                 380

Thr Glu Val Val Val Gly Gly Val Glu Ala Asn Met Ala Ile Ala Gly
        385                 390                 395                 400

Ala Leu Thr Thr Pro Gly Cys Ala Ala Pro Leu Ala Ile Leu Asp Leu
                        405                 410                 415

Gly Ala Gly Ser Thr Asp Ala Ala Ile Val Asn Ala Glu Gly Gln Ile
                        420                 425                 430

Thr Ala Val His Leu Ala Gly Ala Gly Asn Met Val Ser Leu Leu Ile
                        435                 440                 445

Lys Thr Glu Leu Gly Leu Glu Asp Leu Ser Leu Ala Glu Ala Ile Lys
        450                 455                 460

Lys Tyr Pro Leu Ala Lys Val Glu Ser Leu Phe Ser Ile Arg His Glu
        465                 470                 475                 480

Asn Gly Ala Val Glu Phe Phe Arg Glu Ala Leu Ser Pro Ala Val Phe
                        485                 490                 495

Ala Lys Val Val Tyr Ile Lys Glu Gly Glu Leu Val Pro Ile Asp Asn
                        500                 505                 510

Ala Ser Pro Leu Glu Lys Ile Arg Leu Val Arg Arg Gln Ala Lys Glu
                        515                 520                 525

Lys Val Phe Val Thr Asn Cys Leu Arg Ala Leu Arg Gln Val Ser Pro
                530                 535                 540

Gly Gly Ser Ile Arg Asp Ile Ala Phe Val Val Leu Val Gly Gly Ser
        545                 550                 555                 560

Ser Leu Asp Phe Glu Ile Pro Gln Leu Ile Thr Glu Ala Leu Ser His
                        565                 570                 575
```

Tyr Gly Val Val Ala Gly Gln Gly Asn Ile Arg Gly Thr Glu Gly Pro
            580                 585                 590

Arg Asn Ala Val Ala Thr Gly Leu Leu Leu Ala Gly Gln Ala Asn
        595                 600                 605

(2) INFORMATION FOR SEQ ID NO:60:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:60:

Met Asn Lys Ser Gln Gln Ile Ala Thr Ile Thr Leu Ala Ala Ala Lys
1               5                   10                  15

Lys Met Ala Gln Ala Val Glu Ala Lys Ala Leu Glu Ile Asn Val Pro
            20                  25                  30

Val Val Phe Ser Val Val Asp His Gly Gly Asn Thr Leu Leu Met Gln
        35                  40                  45

Arg Met Asp Asp Ala Phe Val Thr Ser Cys Asp Ile Ser Leu Asn Lys
    50                  55                  60

Ala Tyr Thr Ala Cys Cys Leu Arg Gln Gly Thr His Glu Ile Thr Asp
65                  70                  75                  80

Ala Val Gln Pro Gly Ala Ser Leu Tyr Gly Leu Gln Leu Thr Asn Gln
                85                  90                  95

Gln Arg Ile Val Ile Phe Gly Gly Leu Pro Val Ile Leu Asn Gly
            100                 105                 110

Lys Val Ile Gly Ala Val Gly Val Ser Gly Gly Thr Val Glu Gln Asp
            115                 120                 125

Arg Leu Leu Ala Glu Thr Ala Leu Asp Cys Phe Ser Glu Leu
            130                 135                 140

(2) INFORMATION FOR SEQ ID NO:61:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:61:

Met Met Asn Lys Ser Gln Gln Val Gln Thr Ile Thr Leu Ala Ala Ala
1               5                   10                  15

Gln Gln Met Ala Ala Val Glu Lys Lys Ala Thr Glu Ile Asn Val
            20                  25                  30

Ala Val Val Phe Ser Val Val Asp Arg Gly Gly Asn Thr Leu Leu Ile
            35                  40                  45

Gln Arg Met Asp Glu Ala Phe Val Ser Ser Cys Asp Ile Ser Leu Asn
    50                  55                  60

Lys Ala Trp Ser Ala Cys Ser Leu Lys Gln Gly Thr His Glu Ile Thr
65                  70                  75                  80

Ser Ala Val Gln Pro Gly Gln Ser Leu Tyr Gly Leu Gln Leu Thr Asn
                85                  90                  95

Gln Gln Arg Ile Ile Ile Phe Gly Gly Gly Leu Pro Val Ile Phe Asn

```
                100                 105                 110
Glu Gln Val Ile Gly Ala Val Gly Val Ser Gly Gly Thr Val Glu Gln
            115                 120                 125
Asp Gln Leu Leu Ala Gln Cys Ala Leu Asp Cys Phe Ser Ala Leu
    130                 135                 140
```

(2) INFORMATION FOR SEQ ID NO:62:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:62:

```
Met Ser Leu Ser Ser Pro Gly Val His Leu Phe Tyr His Ser Arg Trp
1               5                   10                  15

Gln Gly Thr Arg Val Leu Asp Glu Leu Cys Trp Gly Leu Glu Glu Gln
            20                  25                  30

Gly Val Pro Cys Arg Ala Ile Cys Cys Asp His Asp Cys Ala Leu
        35                  40                  45

Ala Leu Gly Lys Leu Ala Ala Lys Ser Ser Thr Leu Arg Val Gly Leu
    50                  55                  60

Gly Leu Asn Ala Thr Gly Asp Ile Ala Leu Thr His Ala Gln Leu Pro
65                  70                  75                  80

Glu Asp Arg Ala Leu Val Cys Gly His Thr Arg Ala Gly Thr Ala Gln
                85                  90                  95

Ile Arg Thr Leu Gly Ala Asn Ala Gly Gln Leu Val Lys Val Leu Pro
                100                 105                 110

Phe Ser Glu Ile Lys
            115
```

(2) INFORMATION FOR SEQ ID NO:63:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:63:

```
Met Ser Leu Ser Pro Pro Gly Val Arg Leu Phe Tyr Asp Pro Arg Gly
1               5                   10                  15

His His Ala Gly Ala Ile Asn Glu Leu Cys Trp Gly Leu Glu Glu Gln
            20                  25                  30

Gly Val Pro Cys Gln Thr Ile Thr Tyr Asp Gly Gly Asp Ala Ala
        35                  40                  45

Ala Leu Gly Ala Leu Ala Ala Arg Ser Ser Pro Leu Arg Val Gly Ile
    50                  55                  60

Gly Leu Ser Ala Ser Gly Glu Ile Ala Leu Thr His Ala Gln Leu Pro
65                  70                  75                  80

Ala Asp Ala Pro Leu Ala Thr Gly His Val Thr Asp Ser Asp Asp Gln
                85                  90                  95

Leu Arg Thr Leu Gly Ala Asn Ala Gly Gln Leu Val Lys Val Leu Pro
                100                 105                 110
```

Leu Ser Glu Arg Asn
        115

(2) INFORMATION FOR SEQ ID NO:64:

(i) SEQUENCE CHARACTERISTICS:
        (A) LENGTH: 176 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:64:

Met Tyr Arg Ile Tyr Thr Arg Thr Gly Asp Lys Gly Thr Thr Ala Leu
1               5                   10                  15

Tyr Gly Gly Ser Arg Ile Glu Lys Asp His Ile Arg Val Glu Ala Tyr
                20                  25                  30

Gly Thr Val Asp Glu Leu Ile Ser Gln Leu Gly Val Cys Tyr Ala Thr
            35                  40                  45

Thr Arg Asp Ala Gly Leu Arg Glu Ser Leu His His Ile Gln Gln Thr
        50                  55                  60

Leu Phe Val Leu Gly Ala Glu Leu Ala Ser Asp Ala Arg Gly Leu Thr
65                  70                  75                  80

Arg Leu Ser Gln Thr Ile Gly Glu Glu Ile Thr Ala Leu Glu Arg
                85                  90                  95

Leu Ile Asp Arg Asn Met Ala Glu Ser Gly Pro Leu Lys Gln Phe Val
                100                 105                 110

Ile Pro Gly Arg Asn Leu Ala Ser Ala Gln Leu His Val Ala Arg Thr
            115                 120                 125

Gln Ser Arg Arg Leu Glu Arg Leu Leu Thr Ala Met Asp Arg Ala His
        130                 135                 140

Pro Leu Arg Asp Ala Leu Lys Arg Tyr Ser Asn Arg Leu Ser Asp Ala
145                 150                 155                 160

Leu Phe Ser Met Ala Arg Ile Glu Glu Thr Arg Pro Asp Ala Cys Ala
                165                 170                 175

(2) INFORMATION FOR SEQ ID NO:65:

(i) SEQUENCE CHARACTERISTICS:
        (A) LENGTH: 176 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:65:

Met Tyr Arg Ile Tyr Thr Arg Thr Gly Asp Asn Gly Thr Thr Ala Leu
1               5                   10                  15

Phe Gly Gly Ser Arg Ile Asp Lys Asp Asp Ile Arg Val Glu Ala Tyr
                20                  25                  30

Gly Thr Val Asp Glu Leu Ile Ser Gln Leu Gly Val Cys Tyr Ala Ser
            35                  40                  45

Thr Arg Gln Ala Glu Leu Arg Gln Glu Leu His Ala Met Gln Lys Met
        50                  55                  60

Leu Phe Val Leu Gly Ala Glu Leu Ala Ser Asp Gln Lys Gly Leu Thr
65                  70                  75                  80

Arg Leu Lys Gln Arg Ile Gly Glu Glu Asp Ile Gln Ala Leu Glu Gln
                85                  90                  95

```
Leu Ile Asp Arg Asn Met Ala Gln Ser Gly Pro Leu Lys Glu Phe Val
            100                 105                 110

Ile Pro Gly Lys Asn Leu Ala Ser Ala Gln Leu His Val Ala Arg Thr
            115                 120                 125

Leu Thr Arg Arg Leu Glu Arg Ile Leu Ile Ala Met Gly Arg Thr Leu
            130                 135                 140

Thr Leu Arg Asp Glu Ala Arg Arg Tyr Ile Asn Arg Leu Ser Asp Ala
145                 150                 155                 160

Leu Phe Ser Met Ala Arg Ile Glu Glu Thr Thr Pro Asp Val Cys Ala
                165                 170                 175

(2) INFORMATION FOR SEQ ID NO:66:

(i) SEQUENCE CHARACTERISTICS:
        (A) LENGTH: 1830 base pairs
        (B) TYPE: nucleic acid
        (C) STRANDEDNESS: single
        (D) TOPOLOGY: linear (xi) SEQUENCE DESCRIPTION: SEQ ID NO:66:

ATGCGCTATA TCGCTGGCAT TGATATTGGC AACTCCTCGA CAGAAGTCGC CCTGGCGACG      60

GTCGATGACG CAGGTGTGCT GAACATTCGC CACAGCGCGT TGGCTGAAAC CACGGGTATA     120

AAAGGCACAT TACGAAATGT GTTCGGTATC CAGGAGGCGC TAACGCAGGC GGCAAAAGCG     180

GCCGGCATTC AGCTCAGCGA TATTTCGCTT ATTCGCATTA ACGAAGCCAC GCCGGTCATT     240

GGCGATGTGG CGATGGAAAC CATCACGGAA ACCATCATCA CCGAGTCCAC CATGATCGGC     300

CATAACCCGA AGACACCCGG CGGCGTCGGA CTGGGGGTCG GCATCACCAT CACACCAGAG     360

GCGCTGCTGT CCTGCTCCGC GGACACTCCC TATATTCTGG TGGTCTCCTC GGCCTTTGAC     420

TTTGCCGATG TCGCCGCGAT GGTCAATGCG GCAACGGCAG CGGGCTATCA GATAACCGGC     480

ATTATTTTGC AGCAGGATGA CGGCGTGCTG GTCAATAACC GGCTACAGCA ACCGCTACCG     540

GTGATCGACG AAGTTCAGCA TATCGACCGG ATTCCACTTG GCATGCTGGC GGCCGTCGAG     600

GTCGCTTTAC CCGGTAAGAT CATCGAAACG CTCTCCAACC CTTACGGTAT TGCGACCGTT     660

TTCGATCTCA ACGCCGAGGA GAGCCAAAAT ATCGTGCCAA TGGCACGGGC GCTGATTGGC     720

AACCGCTCGG CCGTGGTGGT GAAAACCCCC TCCGGCGACG TCAAGGCCCG CGCTATTCCG     780

GCAGGTAATC TGTTGCTCAT CGCTCAGGGG CGCAGCGTAC AGGTTGATGT GGCCGCCGGG     840

GCGGAAGCCA TCATGAAAGC GGTTGACGGC TGCGGCAAAC TGGACAACGT CGCGGGAGAA     900

GCGGGCACCA ATATCGGCGG CATGCTAGAG CACGTGCGCC AGACCATGGC GGAGCTTACC     960

AATAAGCCAG CTCAGGAGAT CCGCATTCAG GATCTGCTGG CCGTTGATAC GGCGGTGCCA    1020

GTCAGCGTGA CCGGCGGTCT TGCGGGGGAG TTCTCGCTGG AGCAGGCGGT GGGTATCGCC    1080

TCGATGGTCA AGTCGGATCG CCTGCAGATG GCCCTCATCG CCCGTGAAAT TGAGCACAAA    1140

CTGCAGATTG CGGTTCAGGT GGGCGGCGCC GAAGCGGAGG CGGCCATTCT TGGGGCGCTC    1200

ACCACTCCCG GCACCACGCG CCCGCTGGCG ATCCTCGATC TGGGCGCCGG GTCGACCGAC    1260

GCCTCCATTA TCAATGCGCA GGGAGAGATC AGCGCCACTC ACCTGGCCGG CGCCGGCGAT    1320

ATGGTCACGA TGATCATCGC CCGCGAGCTG GGGCTTGAGG ACCGCTACCT GGCGGAAGAG    1380

ATCAAAAAAT ATCCGCTGGC AAAAGTCGAA AGCCTGTTTC ATCTGCGTCA TGAAGACGGC    1440

AGCGTCCAGT TTTTTCCGTC GGCCTTACCA CCGACGGTAT TTGCCCGCGT CTGCGTGAAA    1500

CCGGATGAAC TGGTTCCCCT GCCCGGCGAT CTGCCGCTGG AGAAAGTGCG CGCAATTCGC    1560
```

```
CGTAGCGCCA AATCACGCGT CTTTGTCACC AACGCCCTGC GAGCGTTACG CCAGGTGAGC   1620

CCTACCGGCA ACATTCGCGA CATCCCGTTC GTGGTGCTGG TGGGCGGCTC GTCCCTCGAT   1680

TTCGAGATCC CCCAGCTGGT CACCGACGCG CTGGCGCACT ACCGGCTGGT TGCCGGGCGC   1740

GGCAACATCC GCGGCTGTGA AGGCCCACGC AATGCGGTCG CCAGCGGATT ACTCCTTTCC   1800

TGGCAAAAAG GAGGCACACA TGGAGAGTAG                                   1830
```

(2) INFORMATION FOR SEQ ID NO:67:

(i) SEQUENCE CHARACTERISTICS:
        (A) LENGTH: 609 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:67:

```
Met Arg Tyr Ile Ala Gly Ile Asp Ile Gly Asn Ser Ser Thr Glu Val
  1               5                  10                  15

Ala Leu Ala Thr Val Asp Asp Ala Gly Val Leu Asn Ile Arg His Ser
                 20                  25                  30

Ala Leu Ala Glu Thr Thr Gly Ile Lys Gly Thr Leu Arg Asn Val Phe
             35                  40                  45

Gly Ile Gln Glu Ala Leu Thr Gln Ala Ala Lys Ala Ala Gly Ile Gln
         50                  55                  60

Leu Ser Asp Ile Ser Leu Ile Arg Ile Asn Glu Ala Thr Pro Val Ile
 65                  70                  75                  80

Gly Asp Val Ala Met Glu Thr Ile Thr Glu Thr Ile Ile Thr Glu Ser
                 85                  90                  95

Thr Met Ile Gly His Asn Pro Lys Thr Pro Gly Gly Val Gly Leu Gly
            100                 105                 110

Val Gly Ile Thr Ile Thr Pro Glu Ala Leu Leu Ser Cys Ser Ala Asp
        115                 120                 125

Thr Pro Tyr Ile Leu Val Val Ser Ser Ala Phe Asp Phe Ala Asp Val
    130                 135                 140

Ala Ala Met Val Asn Ala Ala Thr Ala Ala Gly Tyr Gln Ile Thr Gly
145                 150                 155                 160

Ile Ile Leu Gln Gln Asp Asp Gly Val Leu Val Asn Asn Arg Leu Gln
                165                 170                 175

Gln Pro Leu Pro Val Ile Asp Glu Val Gln His Ile Asp Arg Ile Pro
            180                 185                 190

Leu Gly Met Leu Ala Ala Val Glu Val Ala Leu Pro Gly Lys Ile Ile
        195                 200                 205

Glu Thr Leu Ser Asn Pro Tyr Gly Ile Ala Thr Val Phe Asp Leu Asn
    210                 215                 220

Ala Glu Glu Ser Gln Asn Ile Val Pro Met Ala Arg Ala Leu Ile Gly
225                 230                 235                 240

Asn Arg Ser Ala Val Val Lys Thr Pro Ser Gly Asp Val Lys Ala
                245                 250                 255

Arg Ala Ile Pro Ala Gly Asn Leu Leu Leu Ile Ala Gln Gly Arg Ser
            260                 265                 270

Val Gln Val Asp Val Ala Ala Gly Ala Glu Ala Ile Met Lys Ala Val
        275                 280                 285

Asp Gly Cys Gly Lys Leu Asp Asn Val Ala Gly Glu Ala Gly Thr Asn
    290                 295                 300
```

```
Ile Gly Gly Met Leu Glu His Val Arg Gln Thr Met Ala Glu Leu Thr
305                 310                 315                 320

Asn Lys Pro Ala Gln Glu Ile Arg Ile Gln Asp Leu Leu Ala Val Asp
                325                 330                 335

Thr Ala Val Pro Val Ser Val Thr Gly Gly Leu Ala Gly Glu Phe Ser
                340                 345                 350

Leu Glu Gln Ala Val Gly Ile Ala Ser Met Val Lys Ser Asp Arg Leu
            355                 360                 365

Gln Met Ala Leu Ile Ala Arg Glu Ile Glu His Lys Leu Gln Ile Ala
        370                 375                 380

Val Gln Val Gly Gly Ala Glu Ala Glu Ala Ile Leu Gly Ala Leu
385                 390                 395                 400

Thr Thr Pro Gly Thr Thr Arg Pro Leu Ala Ile Leu Asp Leu Gly Ala
                405                 410                 415

Gly Ser Thr Asp Ala Ser Ile Ile Asn Ala Gln Gly Glu Ile Ser Ala
                420                 425                 430

Thr His Leu Ala Gly Ala Gly Asp Met Val Thr Met Ile Ile Ala Arg
            435                 440                 445

Glu Leu Gly Leu Glu Asp Arg Tyr Leu Ala Glu Glu Ile Lys Lys Tyr
450                 455                 460

Pro Leu Ala Lys Val Glu Ser Leu Phe His Leu Arg His Glu Asp Gly
465                 470                 475                 480

Ser Val Gln Phe Phe Pro Ser Ala Leu Pro Pro Thr Val Phe Ala Arg
                485                 490                 495

Val Cys Val Lys Pro Asp Glu Leu Val Pro Leu Pro Gly Asp Leu Pro
                500                 505                 510

Leu Glu Lys Val Arg Ala Ile Arg Arg Ser Ala Lys Ser Arg Val Phe
            515                 520                 525

Val Thr Asn Ala Leu Arg Ala Leu Arg Gln Val Ser Pro Thr Gly Asn
        530                 535                 540

Ile Arg Asp Ile Pro Phe Val Val Leu Val Gly Gly Ser Ser Leu Asp
545                 550                 555                 560

Phe Glu Ile Pro Gln Leu Val Thr Asp Ala Leu Ala His Tyr Arg Leu
                565                 570                 575

Val Ala Gly Arg Gly Asn Ile Arg Gly Cys Glu Gly Pro Arg Asn Ala
                580                 585                 590

Val Ala Ser Gly Leu Leu Leu Ser Trp Gln Lys Gly Gly Thr His Gly
            595                 600                 605

Glu (2) INFORMATION FOR SEQ ID NO:68:

(i) SEQUENCE CHARACTERISTICS:
        (A) LENGTH: 1824 base pairs
        (B) TYPE: nucleic acid
        (C) STRANDEDNESS: single
        (D) TOPOLOGY: linear (xi) SEQUENCE DESCRIPTION: SEQ ID NO:68:

ATGCCGTTAA TAGCCGGGAT TGATATCGGC AACGCCACCA CCGAGGTGGC GCTGGCGTCC     60

GACTACCCGC AGGCGAGGGC GTTTGTTGCC AGCGGGATCG TCGCGACGAC GGGCATGAAA    120

GGGACGCGGG ACAATATCGC CGGGACCCTC GCCGCGCTGG AGCAGGCCCT GGCGAAAACA    180

CCGTGGTCGA TGAGCGATGT CTCTCGCATC TATCTTAACG AAGCCGCGCC GGTGATTGGC    240
```

-continued

| | | | | | |
|---|---|---|---|---|---|
| GATGTGGCGA | TGGAGACCAT | CACCGAGACC | ATTATCACCG | AATCGACCAT | GATCGGTCAT | 300 |
| AACCCGCAGA | CGCCGGGCGG | GGTGGGCGTT | GGCGTGGGGA | CGACTATCGC | CCTCGGGCGG | 360 |
| CTGGCGACGC | TGCCGGCGGC | GCAGTATGCC | GAGGGGTGGA | TCGTACTGAT | TGACGACGCC | 420 |
| GTCGATTTCC | TTGACGCCGT | GTGGTGGCTC | AATGAGGCGC | TCGACCGGGG | GATCAACGTG | 480 |
| GTGGCGGCGA | TCCTCAAAAA | GGACGACGGC | GTGCTGGTGA | CAACCGCCT | GCGTAAAACC | 540 |
| CTGCCGGTGG | TGGATGAAGT | GACGCTGCTG | GAGCAGGTCC | CCGAGGGGGT | AATGGCGGCG | 600 |
| GTGGAAGTGG | CCGCGCCGGG | CCAGGTGGTG | CGGATCCTGT | CGAATCCCTA | CGGGATCGCC | 660 |
| ACCTTCTTCG | GGCTAAGCCC | GGAAGAGACC | CAGGCCATCG | TCCCCATCGC | CCGCGCCCTG | 720 |
| ATTGGCAACC | GTTCCGCGGT | GGTGCTCAAG | ACCCCGCAGG | GGGATGTGCA | GTCGCGGGTG | 780 |
| ATCCCGGCGG | GCAACCTCTA | CATTAGCGGC | GAAAAGCGCC | GCGGAGAGGC | CGATGTCGCC | 840 |
| GAGGGCGCGG | AAGCCATCAT | GCAGGCGATG | AGCGCCTGCG | CTCCGGTACG | CGACATCCGC | 900 |
| GGCGAACCGG | GCACCCACGC | CGGCGGCATG | CTTGAGCGGG | TGCGCAAGGT | AATGGCGTCC | 960 |
| CTGACCGGCC | ATGAGATGAG | CGCGATATAC | ATCCAGGATC | TGCTGGCGGT | GGATACGTTT | 1020 |
| ATTCCGCGCA | AGGTGCAGGG | CGGGATGGCC | GGCGAGTGCG | CCATGGAGAA | TGCCGTCGGG | 1080 |
| ATGGCGGCGA | TGGTGAAAGC | GGATCGTCTG | CAAATGCAGG | TTATCGCCCG | CGAACTGAGC | 1140 |
| GCCCGACTGC | AGACCGAGGT | GGTGGTGGGC | GGCGTGGAGG | CCAACATGGC | CATCGCCGGG | 1200 |
| GCGTTAACCA | CTCCCGGCTG | TGCGGCGCCG | CTGGCGATCC | TCGACCTCGG | CGCCGGCTCG | 1260 |
| ACGGATGCGG | CGATCGTCAA | CGCGGAGGGG | CAGATAACGG | CGGTCCATCT | CGCCGGGGCG | 1320 |
| GGGAATATGG | TCAGCCTGTT | GATTAAAACC | GAGCTGGGCC | TCGAGGATCT | TTCGCTGGCG | 1380 |
| GAAGCGATAA | AAAAATACCC | GCTGGCCAAA | GTGGAAAGCC | TGTTCAGTAT | TCGTCACGAG | 1440 |
| AATGGCGCGG | TGGAGTTCTT | TCGGGAAGCC | CTCAGCCCGG | CGGTGTTCGC | CAAAGTGGTG | 1500 |
| TACATCAAGG | AGGGCGAACT | GGTGCCGATC | GATAACGCCA | GCCCGCTGGA | AAAAATTCGT | 1560 |
| CTCGTGCGCC | GGCAGGCGAA | AGAGAAAGTG | TTTGTCACCA | ACTGCCTGCG | CGCGCTGCGC | 1620 |
| CAGGTCTCAC | CCGGCGGTTC | CATTCGCGAT | ATCGCCTTTG | TGGTGCTGGT | GGGCGGCTCA | 1680 |
| TCGCTGGACT | TTGAGATCCC | GCAGCTTATC | ACGGAAGCCT | TGTCGCACTA | TGGCGTGGTC | 1740 |
| GCCGGGCAGG | GCAATATTCG | GGGAACAGAA | GGGCCGCGCA | ATGCGGTCGC | CACCGGGCTG | 1800 |
| CTACTGGCCG | GTCAGGCGAA | TTAA | | | | 1824 |

METHOD FOR THE RECOMBINANT PRODUCTION OF 1,3-PROPANEDIOL

RELATED APPLICATIONS

The present application is a continuation-in-part application of U.S. Provisional Application Ser. No. 60/030,601 filed Nov. 13, 1996, hereby incorporated herein in its entirety.

FIELD OF INVENTION

The present invention relates to the field of molecular biology and specifically to improved methods for the production of 1,3-propanediol in host cells. In particular, the present invention describes components of gene clusters associated with 1,3-propanediol production in host cells, including protein X, and protein 1, protein 2 and protein 3. More specifically the present invention describes the expression of cloned genes encoding protein X, protein 1, protein 2 and protein 3, either separately or together, for the enhanced production of 1,3-propanediol in host cells.

BACKGROUND 1,3-Propanediol is a monomer having potential utility in the production of polyester fibers and the manufacture of polyurethanes and cyclic compounds.

A variety of chemical routes to 1,3-propanediol are known. For example ethylene oxide may be converted to 1,3-propanediol over a catalyst in the presence of phosphine, water, carbon monoxide, hydrogen and an acid, by the catalytic solution phase hydration of acrolein followed by reduction, or from hydrocarbons such as glycerol, reacted in the presence of carbon monoxide and hydrogen over catalysts having atoms from group VIII of the periodic table. Although it is possible to generate 1,3-propanediol by these methods, they are expensive and generate waste streams containing environmental pollutants.

It has been known for over a century that 1,3-propanediol can be produced from the fermentation of glycerol. Bacterial strains able to produce 1,3-propanediol have been found, for example, in the groups Citrobacter, Clostridium, Enterobacter, Ilyobacter, Kiebsiella, Lactobacillus, and Pelobacter. In each case studied, glycerol is converted to 1,3-propanediol in a two step, enzyme catalyzed reaction sequence. In the first step, a dehydratase catalyzes the conversion of glycerol to 3-hydroxypropionaldehyde (3-HP) and water (Equation 1). In the second step, 3-HP is reduced to 1,3-propanediol by a NAD$^+$-linked oxidoreductase (Equation 2).

$$\text{Glycerol} \rightarrow \text{3-HP} + \text{H}_2\text{O} \quad \text{(Equation 1)}$$

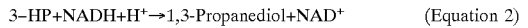

$$\text{3-HP} + \text{NADH} + \text{H}^+ \rightarrow \text{1,3-Propanediol} + \text{NAD}^+ \quad \text{(Equation 2)}$$

The 1,3-propanediol is not metabolized further and, as a result, accumulates in high concentration in the media. The overall reaction consumes a reducing equivalent in the form of a cofactor, reduced b-nicotinamide adenine dinucleotide (NADH), which is oxidized to nicotinamide adenine dinucleotide (NAD$^+$).

The production of 1,3-propanediol from glycerol is generally performed under anaerobic conditions using glycerol as the sole carbon source and in the absence of other exogenous reducing equivalent acceptors. Under these conditions, in for example, strains of Citrobacter, Clostridium, and Klebsiella, a parallel pathway for glycerol operates which first involves oxidation of glycerol to dihydroxyacetone (DHA) by a NAD$^+$- (or NADP$^+$-)linked glycerol dehydrogenase (Equation 3). The DHA, following phosphorylation to dihydroxyacetone phosphate (DHAP) by a DHA kinase (Equation 4), becomes available for biosynthesis and for supporting ATP generation via, for example, glycolysis.

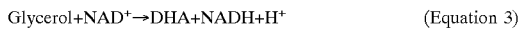

$$\text{Glycerol} + \text{NAD}^+ \rightarrow \text{DHA} + \text{NADH} + \text{H}^+ \quad \text{(Equation 3)}$$

$$\text{DHA} + \text{ATP} \rightarrow \text{DHAP} + \text{ADP} \quad \text{(Equation 4)}$$

In contrast to the 1,3-propanediol pathway, this pathway may provide carbon and energy to the cell and produces rather than consumes NADH.

In *Klebsiella pneumoniae* and *Citrobacter freundii*, the genes encoding the functionally linked activities of glycerol dehydratase (dhaB), 1,3-propanediol oxidoreductase (dhaT), glycerol dehydrogenase (dhaD), and dihydroxyacetone kinase (dhaK) are encompassed by the dha regulon. The dha regulons from Citrobacter and Klebsiella have been expressed in *Escherichia coli* and have been shown to convert glycerol to 1,3-propanediol. Glycerol dehydratase (E.C. 4.2.1.30) and diol [1,2-propanediol] dehydratase (E.C. 4.2.1.28) are related but distinct enzymes that are encoded by distinct genes. In *Salmonella typhimunum* and *Klebsiella pneumoniae*, diol dehydratase is associated with the pdu operon, see Bobik et al., 1992, J. Bacteriol. 174:2253–2266 and U.S. Pat. No. 5,633,362. Tobimatsu, et al., 1996, J. Biol. Chem. 271: 22352–22357 disclose the *K. pneumoniae* gene encoding glycerol dehydratase protein X identified as ORF 4; Segfried et al., 1996, J. Bacteriol. 178: 5793–5796 disclose the *C. freundii* glycerol dehydratase gene encoding protein X identified as ORF Z. Tobimatsu et al., 1995, J. Biol. Chem. 270:7142–7148 disclose the diol dehydratase submits α, β and γ and illustrate the presence of orf 4. Luers (1997, FEMS Microbiology Letters 154:337–345) disclose the amino acid sequence of protein 1, protein 2 and protein 3 of *Clostridium pasteurianum*.

Biological processes for the preparation of glycerol are known. The overwhelming majority of glycerol producers are yeasts, but some bacteria, other fungi and algae are also known to produce glycerol. Both bacteria and yeasts produce glycerol by converting glucose or other carbohydrates through the fructose-1,6-bisphosphate pathway in glycolysis or by the Embden Meyerhof Parnas pathway, whereas, certain algae convert dissolved carbon dioxide or bicarbonate in the chloroplasts into the 3-carbon intermediates of the Calvin cycle. In a series of steps, the 3-carbon intermediate, phosphoglyceric acid, is converted to glyceraldehyde 3-phosphate which can be readily interconverted to its keto isomer dihydroxyacetone phosphate and ultimately to glycerol.

Specifically, the bacteria *Bacillus licheniformis* and *Lactobacillus lycopersica* synthesize glycerol, and glycerol production is found in the halotolerant algae Dunaliella sp. and *Asteromonas gracilis* for protection against high external salt concentrations (Ben-Amotz et al., *Expetientia* 38, 49–52, (1982)). Similarly, various osmotolerant yeasts synthesize glycerol as a protective measure. Most strains of Saccharomyces produce some glycerol during alcoholic fermentation, and this can be increased physiologically by the application of osmotic stress (Albertyn et al., *Mol. Cell. Biol.* 14, 4135–4144, (1994)). Earlier this century commercial glycerol production was achieved by the use of Saccharomyces cultures to which "steering reagents" were added such as sulfites or alkalis. Through the formation of an inactive complex, the steering agents block or inhibit the conversion of acetaldehyde to ethanol; thus, excess reducing equivalents (NADH) are available to or "steered" towards DHAP for reduction to produce glycerol. This method is limited by the partial inhibition of yeast growth that is due to the sulfites. This limitation can be partially overcome by the use of alkalis which create excess NADH equivalents by a different mechanism. In this practice, the alkalis initiated a Cannizarro disproportionation to yield ethanol and acetic acid from two equivalents of acetaldehyde.

The gene encoding glycerol-3-phosphate dehydrogenase (DAR1, GPD1) has been cloned and sequenced from *S. diastaticus* (Wang et al., *J. Bact.* 176, 7091–7095, (1994)). The DAR1 gene was cloned into a shuttle vector and used to transform *E. coli* where expression produced active enzyme. Wang et al. (supra) recognize that DAR1 is regulated by the cellular osmotic environment but do not suggest how the gene might be used to enhance 1,3-propanediol production in a recombinant organism.

Other glycerol-3-phosphate dehydrogenase enzymes have been isolated: for example, sn-glycerol-3-phosphate dehydrogenase has been cloned and sequenced from *S. cerevisiae* (Larason et al., *Mol. Microbiol.* 10, 1101, (1993)) and Albertyn et al., (*Mol. Cell. Biol.* 14, 4135, (1994)) teach the cloning of GPD1 encoding a glycerol-3-phosphate dehydrogenase from *S. cerevisiae*. Like Wang et al. (supra), both Albertyn et al. and Larason et al. recognize the osmo-sensitivity of the regulation of this gene but do not suggest how the gene might be used in the production of 1,3-propanediol in a recombinant organism.

As with G3PDH, glycerol-3-phosphatase has been isolated from *Saccharomyces cerevisiae* and the protein identified as being encoded by the GPP1 and GPP2 genes (Norbeck et al., *J. Biol. Chem.* 271, 13875,(1996)). Like the genes encoding G3PDH, it appears that GPP2 is osmosensitive.

Although biological methods of both glycerol and 1,3-propanediol production are known, it has never been demonstrated that the entire process can be accomplished by a single recombinant organism.

Neither the chemical nor biological methods described above for the production of 1,3-propanediol are well suited for industrial scale production since the chemical processes are energy intensive and the biological processes require the expensive starting material, glycerol. A method requiring low energy input and an inexpensive starting material is needed. A more desirable process would incorporate a microorganism that would have the ability to convert basic carbon sources such as carbohydrates or sugars to the desired 1,3-propanediol end-product.

Although a single organism conversion of fermentable carbon source other than glycerol or dihydroxyacetone to 1,3-propanediol would be desirable, it has been documented that there are significant difficulties to overcome in such an endeavor. For example, Gottschalk et al. (EP 373 230) teach that the growth of most strains useful for the production of 1,3-propanediol, including *Citrobacter freundii, Clostridium autobutylicum, Clostridium butylicum*, and *Klebsiella pneumoniae*, is disturbed by the presence of a hydrogen donor such as fructose or glucose. Strains of *Lactobacillus brevis* and *Lactobacillus buchner*, which produce 1,3-propanediol in co-fermentations of glycerol and fructose or glucose, do not grow when glycerol is provided as the sole carbon source, and, although it has been shown that resting cells can metabolize glucose or fructose, they do not produce 1,3-propanediol. (Veiga DA Cunha et al., *J. Bacteriol.* 174, 1013 (1992)). Similarly, it has been shown that a strain of Ilyobacterpolytropus, which produces 1,3-propanediol when glycerol and acetate are provided, will not produce 1,3-propanediol from carbon substrates other than glycerol, including fructose and glucose. (Steib et al., *Arch. Microbiol.* 140, 139 (1984)). Finally Tong et al. (*Appl. Biochem. Biotech.* 34, 149 (1992)) has taught that recombinant *Escherichia coli* transformed with the dha regulon encoding glycerol dehydratase does not produce 1,3-propanediol from either glucose or xylose in the absence of exogenous glycerol.

Attempts to improve the yield of 1,3-propanediol from glycerol have been reported where co-substrates capable of providing reducing equivalents, typically fermentable sugars, are included in the process. Improvements in yield have been claimed for resting cells of *Citrobacter freundii* and *Klebsiella pneumoniae* DSM 4270 cofermenting glycerol and glucose (Gottschalk et al., supra., and Tran-Dinh et al., DE 3734 764); but not for growing cells of *Klebsiella pneumoniae* ATCC 25955 cofermenting glycerol and glucose, which produced no 1,3-propanediol (I-T. Tong, Ph.D. Thesis, University of Wisconsin-Madison (1992)). Increased yields have been reported for the cofermentation of glycerol and glucose or fructose by a recombinant *Escherichia coli*; however, no 1,3-propanediol is produced in the absence of glycerol (Tong et al., supra.). In these systems, single organisms use the carbohydrate as a source of generating NADH while providing energy and carbon for cell maintenance or growth. These disclosures suggest that sugars do not enter the carbon stream that produces 1,3-propanediol. In no case is 1,3-propanediol produced in the absence of an exogenous source of glycerol. Thus the weight of literature clearly suggests that the production of 1,3-propanediol from a carbohydrate source by a single organism is not possible.

The weight of literature regarding the role of protein X in 1,3-propanediol production by a host cell is at best confusing. Prior to the availability of gene information, McGee et al., 1982, Biochem. Biophys. Res. Comm. 108: 547–551, reported diol dehydratase from *K. pneumoniae* ATCC 8724 to be composed of four subunits identified by size (60 K, 51 K, 29 K, and 15 K daltons) and N-terminal amino acid sequence. In direct contrast to MeGee, Tobimatsu et al. 1995, supra, report the cloning, sequencing and expression of diol dehydratase from the same organism and find no evidence linking the 51 K dalton polypeptide to dehydrase. Tobimatsu et al. 1996, supra, conclude that the protein X polypeptide is not a subunit of glycerol dehydratase, in contrast to GenBank Accession Number U30903 where protein X is described as a large subunit of glycerol dehydratase. Seyfried et al., supra, report that a deletion of 192 bp from the 3' end of orfz (protein X) had no effect on enzyme activity and conclude that orfz does not encode a subunit required for dehydratase activity. Finally, Skraly, F. A. (1997, Thesis entitled "Metabolic Engineering of an Improved 1,3-Propanediol Fermentation") disclose a loss of glycerol dehydratase activity in one experiment where recombinant ORF3 (proteinx) was disrupted creating a large fusion protein but not in another experiment where 1,3-propanediol production from glycerol was diminished compared to a control where ORF3 was intact.

The problem to be solved by the present invention is the biological production of 1,3-propanediol by a single recombinant organism from an inexpensive carbon substrate such as glucose or other sugars in commercially feasible quantities. The biological production of 1,3-propanediol requires glycerol as a substrate for a two step sequential reaction in which a dehydratase enzyme (typically a coenzyme $B_{12}$-dependent dehydratase) converts glycerol to an intermediate, 3-hydroxypropionaldehyde, which is then reduced to 1,3-propanediol by a NADH- (or NADPH) dependent oxidoreductase. The complexity of the cofactor requirements necessitates the use of a whole cell catalyst for an industrial process which utilizes this reaction sequence for the production of 1,3-propanediol. Furthermore, in order to make the process economically viable, a less expensive feedstock than glycerol or dihydroxyacetone is needed and high production levels are desirable. Glucose and other carbohydrates are suitable substrates, but, as discussed above, are known to interfere with 1,3-propanediol production. As a result no single organism has been shown to convert glucose to 1,3-propanediol.

Applicants have solved the stated problem and the present invention provides for bioconverting a fermentable carbon source directly to 1,3-propanediol using a single recombinant organism. Glucose is used as a model substrate and the bioconversion is applicable to any existing microorganism. Microorganisms harboring the genes encoding protein X and protein 1, protein 2 and protein 3 in addition to other proteins associated with the production of 1,3-propanediol, are able to convert glucose and other sugars through the glycerol degradation pathway to 1,3-propanediol with good yields and selectivities. Furthermore, the present invention may be generally applied to include any carbon substrate that is readily converted to 1) glycerol, 2) dihydroxyacetone, or 3) $C_3$ compounds at the oxidation state of glycerol (e.g., glycerol 3-phosphate) or 4) $C_3$ compounds at the oxidation state of dihydroxyacetone (e.g., dihydroxyacetone phosphate or glyceraldehyde 3-phosphate).

SUMMARY OF THE INVENTION

The present invention relates to improved methods for the production of 1,3-propanediol from a single microorganism. The present invention is based, in part, upon the unexpected discovery that the presence of a gene encoding protein X in a microorganism containing at least one gene encoding a dehydratase activity and capable of producing 1,3-propanediol is associated with the in vivo reactivation of dehydratase activity and increased production of 1,3-propanediol in the microorganism. The present invention is also based, in part, upon the unexpected discovery that the presence of a gene encoding protein X and at least one gene encoding a protein selected from the group consisting of protein 1, protein 2 and protein 3 in host cells containing at least one gene encoding a dehydratase activity and capable of producing 1,3-propanediol is associated with in vivo reactivation of the dehydratase activity and increased yields of 1,3-propanediol in the microorganism.

Accordingly, the present invention provides an improved method for the production of 1,3-propanediol from a microorganism capable of producing 1,3-propanediol, said microorganism comprising at least one gene encoding a dehydratase activity, the method comprising the steps of introducing a gene encoding protein X into the organism to create a transformed organism; and culturing the transformed organism in the presence of at least one carbon source capable of being converted to 1,3 propanediol in said transformed host organism and under conditions suitable for the production of 1,3 propanediol wherein the carbon source is selected from the group consisting of monosaccharides, oligosaccharides, polysaccharides, and a one carbon substrate.

In a preferred embodiment, the method for improved production of 1,3-propanediol further comprises introducing at least one gene encoding a protein selected from the group consisting of protein 1, protein 2 and protein 3 into the organism. The microorganism may further comprise at least one of (a) a gene encoding a glycerol-3-phosphate dehydrogenase activity; (b) a gene encoding a glycerol-3-phosphatase activity; and (c) a gene encoding 1,3-propanediol oxidoreductase activity into the microorganism. Gene(s) encoding a dehydratase activity, protein X, proteins 1, 2 or 3 or other genes necessary for the production of 1,3-propanediol may be stably maintained in the host cell genome or may be on replicating plasmids residing in the host microorganism.

The method optionally comprises the step of recovering the 1,3 propanediol. In one aspect of the present invention, the carbon source is glucose.

The microorganism is selected from the group of genera consisting of Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas.

In one aspect, protein X is derived from a glyceol dehydratase gene cluster and in another aspect, protein X is derived from a diol dehydratase gene cluster. The gene encoding the dehydratase activity may be homologous to the microorganism or heterologous to the microorganism. In one embodiment, the glycerol dehydratase gene cluster is derived from an organism selected from the genera consisting of Klebsiella and Citrobactor. In another embodiment, the diol dehydratase gene cluster is derived from an organism selected from the genera consisting of Klebsiella, Clostridium and Salmonella.

In another aspect, the present invention provides a recombinant microorganism comprising at least one gene encoding a dehydratase activity; at least one gene encoding a glycerol-3-phosphatase; and at least one gene encoding protein X, wherein said microorganism is capable of producing 1,3-propanediol from a carbon source. The carbon source may be selected from the group consisting of monosaccharides, oligosaccharides, polysaccharides, and a one carbon substrate. In a further embodiment, the microorganism further comprises a gene encoding a cytosolic glycerol-3-phosphate dehydrogenase. In another embodiment, the recombinant microorganism further comprises at least one gene encoding a protein selected from the group consisting of protein 1, protein 2 and protein 3. The microorganism is selected from the group consisting of Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas. In one aspect, protein X is derived from a glycerol dehydratase gene cluster. In another aspect, protein X is derived from a diol dehydratase gene cluster. In one aspect, the dehydratase activity is heterologous to said microorganism and in another aspect, the dehydratase activity is homologous to said microorganism.

The present invention also provides a method for the in vivo reactivation of a dehydratase activity in a microorganism capable of producing 1,3-propanediol and containing at least one gene encoding a dehydratase activity, comprising the step of introducing a gene encoding protein X into said microorganism. The microorganism is selected from the group consisting of Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas.

In one aspect, the gene encoding the dehydratase activity is heterologous to said microorganism and in another aspect, the gene encoding the dehydratase activity is homologous to said microorganism. In one embodiment, the gene encoding protein X is derived from a glycerol dehydratase gene cluster and in another embodiment, the gene encoding protein X is derived from a diol dehydratase gene cluster.

The present invention also provides expression vectors and host cells containing genes encoding protein X, protein 1, protein 2 and protein 3.

One advantage of the method of production of 1,3-propanediol according to the present invention is the unexpected increased production of 1,3-propanediol in a host cell capable of producing 1,3-propanediol in the presence of nucleic acid encoding protein X as compared to the host cell lacking nucleic acid encoding protein X. As demonstrated infra, a host cell containing nucleic acid encoding dhaB 1, 2 and 3 and protein X is able to produce significanty more 1,3-propanediol than a host cell containing nucleic acid encoding dhaB 1, 2 and 3 and lacking X.

Another advantage of the present invention as demonstrated infra, is that the presence of nucleic acid encoding protein X along with nucleic acid encoding at least one of protein 1, protein 2 and protein 3 in a host cell capable of producing 1,3-propanediol gives the unexpected result of increased production of 1,3-propanediol in the host cell over 1,3-propanediol production in the host cell lacing nucleic acid encoding protein X along with nucleic acid encoding at least one of protein 1, protein 2 and protein 3.

Yet another advantage of the method of production of the present invention as shown infra is the in vivo reactivation of the dehydratase activity in a microorganism that is associated with the presence of nucleic acid encoding protein X in the microorganism.

BRIEF DESCRIPTION OF THE DRAWINGS

FIG. 1 illustrates components of the glycerol dehydratase gene cluster from Klebsiella pneumoniae on plasmid pHK28-26 (SEQ ID NO:19). In this figure, orfY encodes protein 1, orfX encodes protein 2 and orfW encodes protein 3. DhaB-X refers to protein X.

Figure 2E:
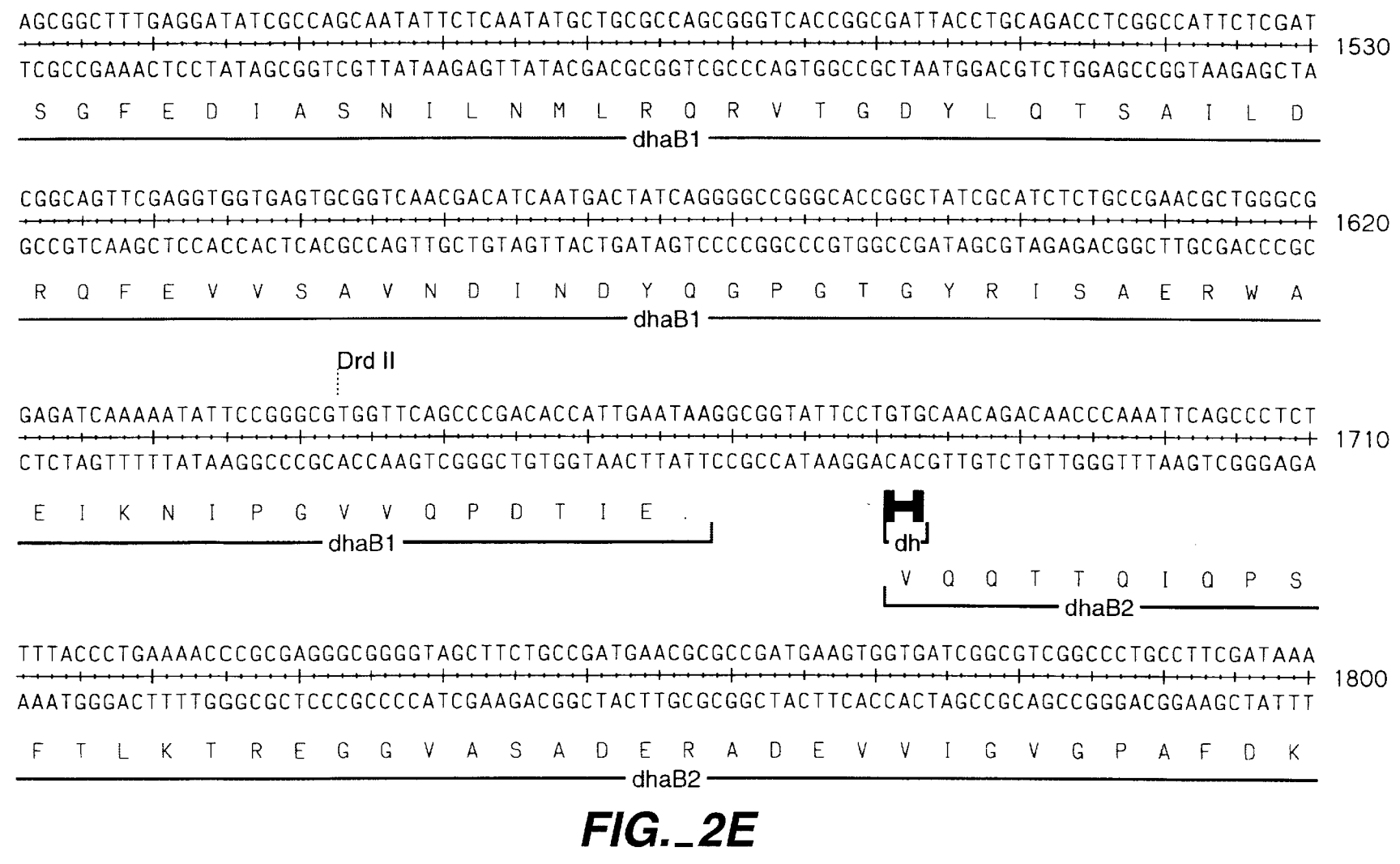

FIGS. 2A–2G illustrates the nucleotide SEQ ID NO:68 and amino acid sequence of Klebsiella pneumoniae glycerol dehydratase protein X (dhab4) (SEQ ID NO:59).

FIG. 3 illustrates the amino acid alignment of *Klebsiella pneumonia* protein 1 (SEQ ID NO:61) and *Citrobacter freundii* protein 1 (SEQ ID NO:60) (designated in FIG. 3 as orfY).

FIG. 4 illustrates the amino acid alignment of *Klebsiella pneumonia* protein 2 (SEQ ID NO:63) and *Citrobacter freundii* protein 2 (SEQ ID NO:62) (designated in FIG. 4 as orfX).

FIG. 5 illustrates the amino acid alignment of *Klebsiella pneumonia* protein 3 (SEQ ID NO:64) and *Citrobacter freundii* protein 3 (SEQ ID NO:65) (designated in FIG. 5 as orfW).

FIG. 6 illustrates the in situ reactivation comparison of plasmids pHK28-26 (which contains dhaB subunits 1, 2 and 3 as well as protein X and the open reading frames encoding protein 1, protein 2 and protein 3) vs. pDT24 (which contains dhaB subunits 1, 2 and 3 as well as protein X) in *E. coli* DH5α cells.

FIG. 7 illustrate the in situ reactivation comparison of plasmids pM7 (containing genes encoding dhaB subunits 1, 2 and 3 and protein X) vs. Plasmid pM11 (containing genes encoding dhaB subunits 1, 2 and 3) in *E. coli* DH5α cells.

FIGS. 8A–8E illustrates the nucleic acid (SEQ ID NO:66) and amino acid (SEQ ID NO:67) sequence of *K. pneumoniae* diol dehydratase gene cluster protein X.

FIG. 9 illustrates a standard 10 liter fermentation for 1,3 propandiol production using *E. coli* FM5/pDT24 (FM5 described in Amgen patent U.S. Pat. No. 5,494,816, ATCC accession No. 53911).

FIG. 10 illustrates a standard 10 liter fermentation for 1,3 propandiol production using *E. coli* DH5alpha/pHK28-26.

BRIEF DESCRIPTION OF BIOLOGICAL DEPOSITS AND SEQUENCE LISTING

The transformed *E. coli* W2042 (comprising the *E. coli* host W1485 and plasmids pDT20 and pAH42) containing the genes encoding glycerol-3-phosphate dehydrogenase (G3PDH) and glycerol-3-phosphatase (G3P phosphatase), glycerol dehydratase (dhaB), and 1,3-propanediol oxidoreductase (dhaT) was deposited on Sep. 26, 1996 with the ATCC under the terms of the Budapest Treaty on the International Recognition of the Deposit of Micro-organisms for the Purpose of Patent Procedure and is designated as ATCC 98188.

*S. cerevisiae* YPH500 harboring plasmids pMCK10, pMCK17, pMCK30 and pMCK35 containing genes encoding glycerol-3-phosphate dehydrogenase (G3PDH) and glycerol-3-phosphatase (G3P phosphatase), glycerol dehydratase (dhaB), and 1,3-propanediol oxidoreductase (dhaT) was deposited on Sep. 26, 1996 with the ATCC under the terms of the Budapest Treaty on the International Recognition of the Deposit of Micro-organisms for the Purpose of Patent Procedure and is designated as ATCC 74392.

*E. coli* DH5α containing pKP1 which has about 35kb of a Klebsiella genome which contains the glycerol dehydratase, protein X and proteins 1, 2 and 3 was deposited on Apr. 18, 1995 with the ATCC under the terms of the Budapest Treaty and was designated ATCC 69789. *E. coli* DH5α containing pKP4 containing a portion of the Klebsiella genome encoding diol dehydratase enzyme, including protein X was deposited on Apr. 18, 1995 with the ATCC under the terms of the Budapest Treaty and was designated ATCC 69790.

"ATCC" refers to the American Type Culture Collection international depository located at 12301 Parklawn Drive, Rockville, Md. 20852 U.S.A. The designations refer to the accession number of the deposited material.

DETAILED DESCRIPTION OF THE INVENTION

The present invention relates to the production of 1,3-propanediol in a single microorganism and provides improved methods for production of 1,3-propanediol from a fermentable carbon source in a single recombinant organism. The method incorporates a microorganism capable of producing 1,3-propanediol comprising either homologous or heterologous genes encoding dehydratase (dhaB), at least one gene encoding protein X and optionally at least one of the genes encoding a protein selected from the group consisting of protein 1, protein 2 and protein 3. Optionally, the microorganism contains at least one gene encoding glycerol-3-phosphate dehydrogenase, glycerol-3-phosphatase and 1,3-propanediol oxidoreductase (dhaT). The recombinant microorganism is contacted with a carbon substrate and 1,3-propanediol is isolated from the growth media.

The present method provides a rapid, inexpensive and environmentally responsible source of 1,3-propanediol monomer useful in the production of polyesters and other polymers.

The following definitions are to be used to interpret the claims and specification.

The term "dehydratase gene cluster" or "gene cluster" refers to the set of genes which are associated with 1,3-propanediol production in a host cell and is intended to encompass glycerol dehydratase gene clusters as well as diol dehydratase gene clusters. The dha regulon refers to a glycerol dehydratase gene cluster, as illustrated in FIG. 1 which includes regulatory regions.

The term "regenerating the dehydratase activity" or "reactivating the dehydratase activity" refers to the phenomenon of converting a dehydratase not capable of catalysis of a substrate to one capable of catalysis of a substrate or to the phenomenon of inhibiting the inactivation of a dehydratase or the phenomenon of extending the useful halflife of the dehydratase enzyme in vivo.

The terms "glycerol dehydratase" or "dehydratase enzyme" or "dehydratase activity" refer to the polypeptide (s) responsible for an enzyme activity that is capable of isomerizing or converting a glycerol molecule to the product 3-hydroxypropionaldehyde. For the purposes of the present invention the dehydratase enzymes include a glycerol dehydratase (GenBank U09771, U30903) and a diol dehydratase (GenBank D45071) having preferred substrates of glycerol and 1,2-propanediol, respectively. Glycerol dehydratase of K. pneumoniae ATCC 25955 is encoded by the genes dhaB1, dhaB2, and dhaB3 identified as SEQ ID NOS:1, 2 and 3, respectively. The dhaB1, dhaB2, and dhaB3 genes code for the a, b, and c subunits of the glycerol dehydratase enzyme, respectively.

Figure 8C:
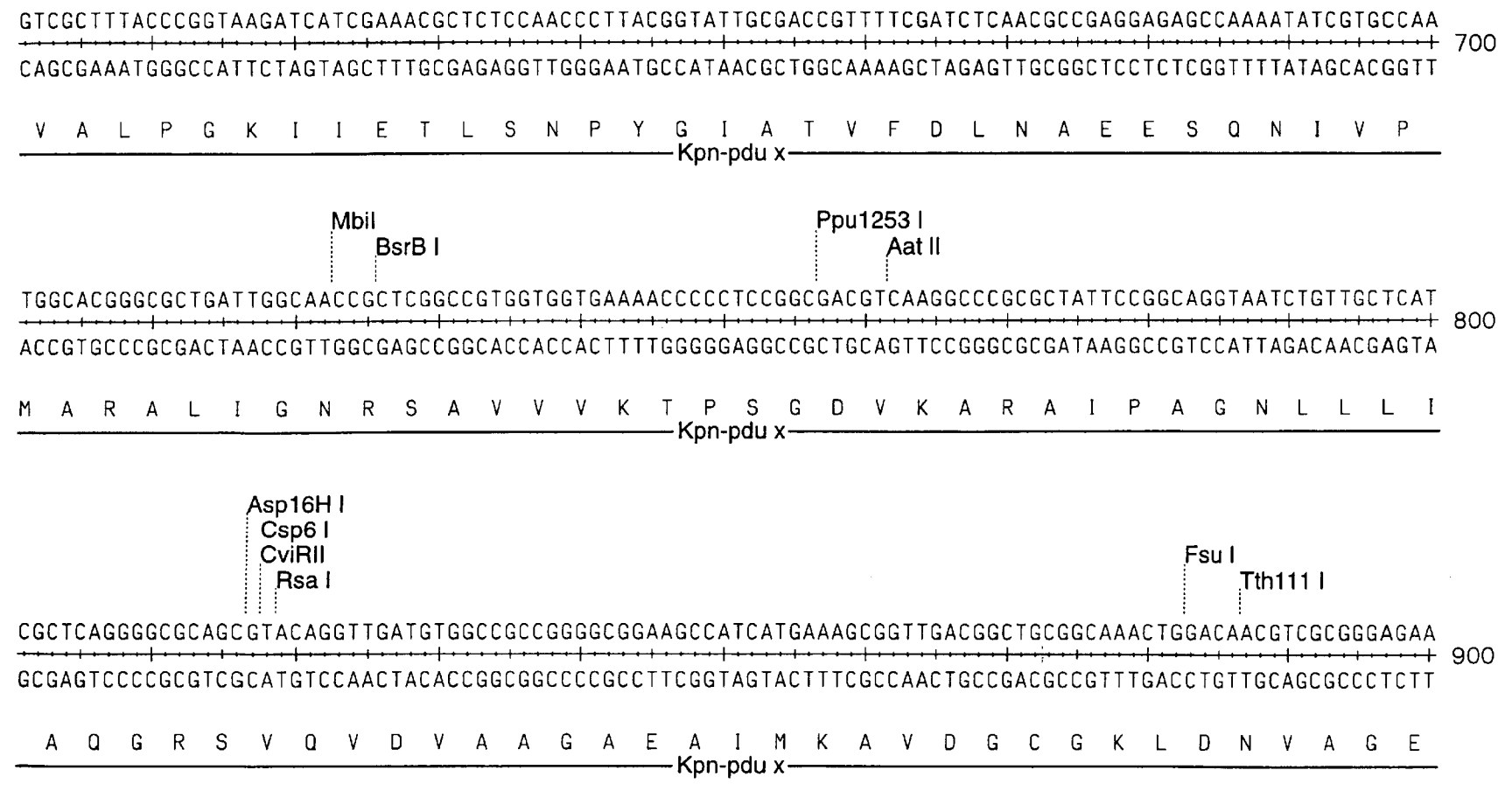

The phrase "protein X of a dehydratase gene cluster" or "dhaB protein X" or "protein X" refers to a protein that is comparable to protein X of the Klebsiella pneumoniae dehydratase gene cluster as shown in FIG. 2 or alternatively comparable to protein X of Klebsiella pneumoniae diol dehydratase gene cluster as shown in FIG. 8. Preferably protein X is capable of increasing the production of 1,3-propanediol in a host organism over the production of 1,3-propanediol in the absence of protein X in the host organism. Being comparable means that DNA encoding the protein is either in the same structural location as DNA encoding Klebsiella protein X with respect to Klebsiella dhaB1, dhaB2 and dhaB3, i.e., DNA encoding protein X is 3' to nucleic acid encoding dhaB1–B3, or that protein X has overall amino acid similarity to either Klebsiella diol or glycerol dehydratase protein X. The present invention encompasses protein X molecules having at least 50%; or at least 65%; or at least 80%; or at least 90% or at least 95% similarity to the protein X of K. pneumoniae glycerol or diol dehydratase or the C. freundii protein X.

Included within the term "protein X" is protein X, also referred to as ORF Z, from Citrobacterdha regulon (Segfried M. 1996, J. Bacteriol. 178: 5793:5796). The present invention also encompasses amino acid variations of protein X from any microorganism as long as the protein X variant retains its essential functional characteristics of increasing the production of 1,3-propanediol in a host organism over the production of 1,3-propanediol in the host organism in the absence of protein X.

A portion of the Klebsiella genome encoding the glycerol dehydratase enzyme activity as well as protein X was transformed into E. coli and the transformed E. coli was deposited on Apr. 18, 1995 with the ATCC under the terms of the Budapest Treaty and was designated as ATCC accession number 69789. A portion of the Klebsiella genome encoding the diol dehydratase enzyme activity as well as protein X was transformed into E. coli and the transformed E. coli was deposited on Apr. 18, 1995 with the ATCC under the terms of the Budapest Treaty and was designated as ATCC accession number 69790.

Klebsiella glycerol dehydratase protein X is found at bases 9749–11572 of SEQ ID NO:19, counting the first base of dhaK as position number 1. Citrobacter freundii (ATCC accession number CFU09771) nucleic acid encoding protein X is found between positions 11261 and 13072.

The present invention encompasses genes encoding dehydratase protein X that are recombinantly introduced and replicate on a plasmid in the host organism as well as genes that are stably maintained in the host genome. The present invention encompasses a method for enhanced production of 1,3-propanediol wherein the gene encoding protein X is transformed in a host cell together with genes encoding the dehydratase activity and/or other genes necessary for the production of 1,3-propanediol. The gene encoding protein X, dehydratase activity and/or other genes may be on the same or different expression cassettes. Alternatively, the gene encoding protein X may be transformed separately, either before or after genes encoding the dehydratase activity and/or other activities. The present invention encompasses host cell having endogenous nucleic acid encoding protein X as well as host cell lacking endogenous nucleic acid encoding protein X.

The terms "protein 1", "protein 2" and "protein 3" refer to the proteins encoded in a microorganism that are comparable to protein 1 (SEQ ID NO: 60 or SEQ ID NO: 61)(also referred to as orfY), protein 2 (SEQ ID NO: 62 or SEQ ID NO: 63) (also referred to as orfX) and protein 3 (SEQ ID NO: 64 or SEQ ID NO: 65) (also referred to as orfW), respectively.

Preferably, in the presence of protein X, at least one of proteins 1, 2 and 3 is capable of increasing the production of 1,3-propanediol in a host organism over the production of 1,3-propanediol in the absence of protein X and at least one of proteins 1, 2 and 3 in the host organism. Being comparable means that DNA encoding the protein is either in the same structural location as DNA encoding the respective proteins, as shown in FIG. 1, or that the respective proteins have overall amino acid similarity to the respective SEQ ID NOS shown in FIGS. 3, 4 and 5.

The present invention encompasses protein 1 molecules having at least 50%; or at least 65%; or at least 80%; or at least 90% or at least 95% similarity to SEQ ID NO: 60 or SEQ ID NO: 61. The present invention encompasses protein 2 molecules having at least 50%; or at least 65 %; or at least 80%; or at least 90% or at least 95% similarity to SEQ ID NO: 62 or SEQ ID NO: 63. The present invention encompasses protein 3 molecules having at least 50%; or at least 65 %; or at least 80%; or at least 90% or at least 95% similarity to SEQ ID NO: 64 or SEQ ID NO: 65.

Included within the terms "protein 1", "protein 2" and "protein 3", respectively, are orfY, orfX and orfW from Clostridium pasteurianum (Luers, et al., supra) as well as molecules having at least 50%; or at least 65%; or at least 80%; or at least 90% or at least 95% similarity to C. pasterurianum orfY, orfX or orfW. The present invention also encompasses amino acid variations of proteins 1, 2 and 3 from any microorganism as long as the protein variant, in combination with protein X, retains its essential functional characteristics of increasing the production of 1,3-propanediol in a host organism over the production of 1,3-propanediol in the host organism in their absence.

The present invention encompasses a method for enhanced production of 1,3-propanediol wherein the gene(s) encoding at least one of protein 1, protein 2 and protein 3 is transformed in a host cell together with genes encoding protein X, the dehydratase activity and/or other genes necessary for the production of 1,3-propanediol. The gene(s) encoding at least on of proteins 1, 2 and 3, protein X, dehydratase activity and/or other genes may be on the same or different expression cassettes. Alternatively, the gene(s) encoding at least one of proteins 1, 2 and 3 may be transformed separately, either before or after genes encoding the dehydratase activity and/or other activities. The present invention encompasses host cell having endogenous nucleic acid encoding protein 1, protein 2 or protein 3 as well as host cell lacking endogenous nucleic acid encoding the proteins.

The terms "oxidoreductase" or "1,3-propanediol oxidoreductase" refer to the polypeptide(s) responsible for an enzyme activity that is capable of catalyzing the reduction of 3-hydroxypropionaldehyde to 1,3-propanediol. 1,3-Propanediol oxidoreductase includes, for example, the polypeptide encoded by the dhaT gene (GenBank U09771, U30903) and is identified as SEQ ID NO:4.

The terms "glycerol-3-phosphate dehydrogenase" or "G3PDH" refer to the polypeptide(s) responsible for an enzyme activity capable of catalyzing the conversion of dihydroxyacetone phosphate (DHAP) to glycerol-3-phosphate (G3P). In vivo G3PDH may be NADH-, NADPH-, or FAD-dependent. Examples of this enzyme activity include the following: NADH-dependent enzymes (EC 1.1.1.8) are encoded by several genes including GPD1 (GenBank Z74071×2) or GPD2 (GenBank Z351691×1) or GPD3 (GenBank G984182) or DAR1 (GenBank Z74071× 2); a NADPH-dependent enzyme (EC 1.1.1.94) is encoded by gpsA (GenBank U32164, G466746 (cds 197911-196892), and L45246); and FAD-dependent enzymes (EC 1.1.99.5) are encoded by GUT2 (GenBank Z47047×23) or glpD (GenBank G147838) or glpABC (GenBank M20938).

The terms "glycerol-3-phosphatase" or "sn-glycerol-3-phosphatase" or "d,l-glycerol phosphatase" or "G3P phosphatase" refer to the polypeptide(s) responsible for an enzyme activity that is capable of catalyzing the conversion of glycerol-3-phosphate to glycerol. G3P phosphatase includes, for example, the polypeptides encoded by GPP1 (GenBank Z47047×125) or GPP2 (GenBank UI8813×11).

The term "glycerol kinase" refers to the polypeptide(s) responsible for an enzyme activity capable of catalyzing the conversion of glycerol to glycerol-3-phosphate or glycerol-3-phosphate to glycerol, depending on reaction conditions. Glycerol kinase includes, for example, the polypeptide encoded by GUT1 (GenBank U11583×19).

The terms "GPD1", "DAR1", "OSGI", "D2830", and "YDL022W" will be used interchangeably and refer to a gene that encodes a cytosolic glycerol-3-phosphate dehydrogenase and characterized by the base sequence given as SEQ ID NO:5.

The term "GPD2" refers to a gene that encodes a cytosolic glycerol-3-phosphate dehydrogenase and characterized by the base sequence given as SEQ ID NO:6.

The terms "GUT2" and "YIL155C" are used interchangably and refer to a gene that encodes a mitochondrial glycerol-3-phosphate dehydrogenase and characterized by the base sequence given in SEQ ID NO:7.

The terms "GPP1", "RHR2" and "YIL053W" are used interchangably and refer to a gene that encodes a cytosolic glycerol-3-phosphatase and characterized by the base sequence given as SEQ ID NO:8.

The terms "GPP2", "HOR2" and "YER062C" are used interchangably and refer to a gene that encodes a cytosolic glycerol-3-phosphatase and characterized by the base sequence given as SEQ ID NO:9.

The term "GUT1" refers to a gene that encodes a cytosolic glycerol kinase and characterized by the base sequence given as SEQ ID NO:10.

The terms "function" or "enzyme function" refer to the catalytic activity of an enzyme in altering the energy required to perform a specific chemical reaction. It is understood that such an activity may apply to a reaction in equilibrium where the production of either product or substrate may be accomplished under suitable conditions.

The terms "polypeptide" and "protein" are used interchangeably.

The terms "carbon substrate" and "carbon source" refer to a carbon source capable of being metabolized by host organisms of the present invention and particularly carbon sources selected from the group consisting of monosaccharides, oligosaccharides, polysaccharides, and one-carbon substrates or mixtures thereof.

The terms "host cell" or "host organism" refer to a microorganism capable of receiving foreign or heterologous genes and of expressing those genes to produce an active gene product. The terms "foreign gene", "foreign DNA", "heterologous gene" and "heterologous DNA" refer to genetic material native to one organism that has been placed within a host organism by various means. The gene of interest may be a naturally occurring gene, a mutated gene or a synthetic gene.

The terms "recombinant organism" and "transformed host" refer to any organism having been transformed with heterologous or foreign genes or extra copies of homologous genes. The recombinant organisms of the present invention express foreign genes encoding glycerol-3-phosphate dehydrogenase (G3PDH) and glycerol-3-phosphatase (G3P phosphatase), glycerol dehydratase (dhaB), and 1,3-propanediol oxidoreductase (dhaT) for the production of 1,3-propanediol from suitable carbon substrates.

"Gene" refers to a nucleic acid fragment that expresses a specific protein, including regulatory sequences preceding (5' non-coding) and following (3' non-coding) the coding region. The terms "native" and "wild-type" refer to a gene as found in nature with its own regulatory sequences.

The terms "encoding" and "coding" refer to the process by which a gene, through the mechanisms of transcription and translation, produces an amino acid sequence. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1× SSC, 0.1% SDS, 65° C.), with the sequences exemplified herein.

The term "expression" refers to the transcription and translation to gene product from a gene coding for the sequence of the gene product.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the product of a transformation.

The term "genetically altered" refers to the process of changing hereditary material by transformation or mutation.

The term "isolated" refers to a protein or DNA sequence that is removed from at least one component with which it is naturally associated. The term "homologous" refers to a protein or polypeptide native or naturally occurring in a gram-positive host cell. The invention includes microorganisms producing the homologous protein via recombinant DNA technology.

Construction of Recombinant Organisms

Recombinant organisms containing the necessary genes that will encode the enzymatic pathway for the conversion of a carbon substrate to 1,3-propanediol may be constructed using techniques well known in the art. As discussed in Example 9, genes encoding Klebsiella dhaB1, dhaB2, dhaB3 and protein X were used to transform E. coli DH5α and in Example 10, genes encoding at least one of Klebsiella proteins 1, 2 and 3 as well as at least one gene encoding protein X was used to transform E. coli.

Genes encoding glycerol-3-phosphate dehydrogenase (G3PDH), glycerol-3-phosphatase (G3P phosphatase), glycerol dehydratase (dhaB), and 1,3-propanediol oxidoreductase (dhaT) were isolated from a native host such as Klebsiella or Saccharomyces and used to transform host strains such as E. coli DH5a, ECL707, AA200, or W1485; the Saccharomyces cerevisiae strain YPH500; or the Klebsiella pneumoniae strains ATCC 25955 or ECL 2106.

Isolation of Genes

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Alternatively, cosmid libraries may be created where large segments of genomic DNA (35–45 kb) may be packaged into vectors and used to transform appropriate hosts. Cosmid vectors are unique in being able to accommodate large quantities of DNA. Generally, cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. Methods of using cosmid vectors for the transformation of suitable bacterial hosts are well described in Sambrook et al., *Molecular Cloning: A Laboratory Manual*, Second Edition (1989) Cold Spring Harbor Laboratory Press, Cold Spring Harbon, N.Y. (1989).

Typically to clone cosmids, foreign DNA is isolated and ligated, using the appropriate restriction endonucleases, adjacent to the cos region of the cosmid vector. Cosmid vectors containing the linearized foreign DNA is then reacted with a DNA packaging vehicle such as bacteriophage 1. During the packaging process the cos sites are cleaved and the foreign DNA is packaged into the head portion of the bacterial viral particle. These particles are then used to transfect suitable host cells such as E. coli. Once injected into the cell, the foreign DNA circularizes under the influence of the cos sticky ends. In this manner large segments of foreign DNA can be introduced and expressed in recombinant host cells.

Isolation and cloning of genes encoding glycerol dehydratase (dhaB) and 1,3-propanediol oxido-reductase (dhaT)

Cosmid vectors and cosmid transformation methods were used within the context of the present invention to clone large segments of genomic DNA from bacterial genera known to possess genes capable of processing glycerol to 1,3-propanediol. Specifically, genomic DNA from K. pneumoniae ATCC 25955 was isolated by methods well known in the art and digested with the restriction enzyme Sau3A for insertion into a cosmid vector Supercos 1 and packaged using Gigapackli packaging extracts. Following construction of the vector E. coli XL1-Blue MR cells were transformed with the cosmid DNA. Transformants were screened for the ability to convert glycerol to 1,3-propanediol by growing the cells in the presence of glycerol and analyzing the media for 1,3-propanediol formation.

Two of the 1,3-propanediol positive transformants were analyzed and the cosmids were named pKP1 and pKP2.

DNA sequencing revealed extensive homology to the glycerol dehydratase gene (dhaB) from *C. freundii*, demonstrating that these transformants contained DNA encoding the glycerol dehydratase gene. Other 1,3-propanediol positive transformants were analyzed and the cosmids were named pKP4 and pKP5. DNA sequencing revealed that these cosmids carried DNA encoding a diol dehydratase gene.

Isolation of genes encoding protein X, protein 1, protein 2 and protein 3

Although the instant invention utilizes the isolated genes from within a Klebsiella cosmid, alternate sources of dehydratase genes and protein X and protein 1, protein 2 and protein 3 include, but are not limited to, Citrobacter, Clostridia, and Salmonella. Tobimatsu, et al., 1996, J. Biol. Chem. 271: 22352–22357 disclose the *K. pneumoniae* glycerol dehydratase operon where protein X is identified as ORF 4; Segfried et al., 1996, J. Bacteriol. 178: 5793–5796 disclose the *C. freundii* glycerol dehydratase operon where protein X is identified as ORF Z. FIG. 8 discloses Klebsiella diol dehydratase protein X and FIGS. 3, 4 and 5 disclose amino acid sequences of proteins 1, 2 and 3 from Klebsiella and Citrobacter.

Genes encoding G3PDH and G3P phosphatase

The present invention provides genes suitable for the expression of G3PDH and G3P phosphatase activities in a host cell.

Genes encoding G3PDH are known. For example, GPD1 has been isolated from Saccharomyces and has the base sequence given by SEQ ID NO:5, encoding the amino acid sequence given in SEQ ID NO:11 (Wang et al., supra). Similarly, G3PDH activity is has also been isolated from Saccharomyces encoded by GPD2 having the base sequence given in SEQ ID NO:6, encoding the amino acid sequence given in SEQ ID NO:12 (Eriksson et al., *Mol. Microbiol.* 17, 95, (1995).

It is contemplated that any gene encoding a polypeptide responsible for G3PDH activity is suitable for the purposes of the present invention wherein that activity is capable of catalyzing the conversion of dihydroxyacetone phosphate (DHAP) to glycerol-3-phosphate (G3P). Further, it is contemplated that any gene encoding the amino acid sequence of G3PDH as given by any one of SEQ ID NOS:11, 12, 13, 14, 15 and 16 corresponding to the genes GPD1, GPD2, GUT2, gpsA, glpD, and the a subunit of glpABC, respectively, will be functional in the present invention wherein that amino acid sequence encompasses amino acid substitutions, deletions or additions that do not alter the function of the enzyme. It will be appreciated by the skilled person that genes encoding G3PDH isolated from other sources are also be suitable for use in the present invention. For example, genes isolated from prokaryotes include GenBank accessions M34393, M20938, L06231, U12567, L45246, L45323, L45324, L45325, U32164, and U39682; genes isolated from fungi include GenBank accessions U30625, U30876 and X56162; genes isolated from insects include GenBank accessions X61223 and X14179; and genes isolated from mammalian sources include GenBank accessions U12424, M25558 and X78593.

Genes encoding G3P phosphatase are known. For example, GPP2 has been isolated from *Saccharomyces cerevisiae* and has the base sequence given by SEQ ID NO:9 which encodes the amino acid sequence given in SEQ ID NO:17 (Norbeck et al., *J. Biol. Chem.* 271, p. 13875, 1996).

It is contemplated that any gene encoding a G3P phosphatase activity is suitable for the purposes of the present invention wherein that activity is capable of catalyzing the conversion of glycerol-3-phosphate to glycerol. Further, it is contemplated that any gene encoding the amino acid sequence of G3P phosphatase as given by SEQ ID NOS:33 and 17 will be functional in the present invention wherein that amino acid sequence encompasses amino acid substitutions, deletions or additions that do not alter the function of the enzyme. It will be appreciated by the skilled person that genes encoding G3P phosphatase isolated from other sources are also suitable for use in the present invention. For example, the dephosphorylation of glycerol-3-phosphate to yield glycerol may be achieved with one or more of the following general or specific phosphatases: alkaline phosphatase (EC 3.1.3.1) [GenBank M19159, M29663, U02550 or M33965]; acid phosphatase (EC 3.1.3.2) [GenBank U51210, U19789, U28658 or L20566]; glycerol-3-phosphatase (EC 3.1.3.-) [GenBank Z38060 or U18813×11]; glucose-1-phosphatase (EC 3.1.3.10) [GenBank M33807]; glucose-6-phosphatase (EC 3.1.3.9) [GenBank U00445]; fructose-1,6-bisphosphatase (EC 3.1.3.11) [GenBank X12545 or J03207] or phosphotidyl glycero phosphate phosphatase (EC 3.1.3.27) [GenBank M23546 and M23628].

Genes encoding glycerol kinase are known. For example, GUT1 encoding the glycerol kinase from Saccharomyces has been isolated and sequenced (Pavlik et al., *Curr. Genet.* 24, 21, (1993)) and the base sequence is given by SEQ ID NO:10 which encodes the amino acid sequence given in SEQ ID NO:18. It will be appreciated by the skilled artisan that although glycerol kinase catalyzes the degradation of glycerol in nature the same enzyme will be able to function in the synthesis of glycerol to convert glycerol-3-phosphate to glycerol under the appropriate reaction energy conditions. Evidence exists for glycerol production through a glycerol kinase. Under anaerobic or respiration-inhibited conditions, *Trypanosoma brucei* gives rise to glycerol in the presence of Glycerol-3-P and ADP. The reaction occurs in the glycosome compartment (D. Hammond, *J. Biol. Chem.* 260, 15646–15654, (1985)).

Host cells

Suitable host cells for the recombinant production of 1,3-propanediol may be either prokaryotic or eukaryotic and will be limited only by the host cell ability to express active enzymes. Preferred hosts will be those typically useful for production of glycerol or 1,3-propanediol such as Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas. Most preferred in the present invention are *E. coli*, Klebsiella species and Saccharomyces species.

Adenosyl-cobalamin (coenzyme $B_{12}$) is an essential cofactor for glycerol dehydratase activity. The coenzyme is the most complex non-polymeric natural product known, and its synthesis in vivo is directed using the products of about 30 genes. Synthesis of coenzyme $B_{12}$ is found in prokaryotes, some of which are able to synthesize the compound de novo, while others can perform partial reactions. *E. coli*, for example, cannot fabricate the corrin ring structure, but is able to catalyze the conversion of cobinamide to corrinoid and can introduce the 5'-deoxyadenosyl group.

Eukaryotes are unable to synthesize coenzyme $B_{12}$ de novo and instead transport vitamin $B_{12}$ from the extracellular milieu with subsequent conversion of the compound to its functional form of the compound by cellular enzymes. Three enzyme activities have been described for this series of reactions. 1) aquacobalamin reductase (EC 1.6.99.8) reduces Co(III) to Co(II); 2) cob(II)alamin reductase (EC 1.6.99.9) reduces Co(II) to Co(I); and 3) cob(I)alamin adenosyltransferase (EC 2.5.1.17) transfers a 5'deoxyadenosine moiety from ATP to the reduced corrinoid. This last enzyme activity is the best characterized of the three, and is encoded by cobA in *S. typhimufum*, btuR in *E. coli* and cobO in *P. denitrificans*. These three cob(I)alamin adenosyltransferase genes have been cloned and sequenced. Cob(I)alamin adenosyltransferase activity has been detected in human fibroblasts and in isolated rat mitochondria (Fenton et al., *Biochem. Biophys. Res. Commun.* 98, 283–9, (1981)). The two enzymes involved in cobalt reduction are poorly characterized and gene sequences are not available. There are reports of an aquacobalamin reductase from *Euglena gracilis* (Watanabe et al., *Arch. Biochem. Biophys.* 305, 421–7, (1993)) and a microsomal cob(III)alamin reductase is present in the microsomal and mitochondrial inner membrane fractions from rat fibroblasts (Pezacka, *Biochim. Biophys. Acta,* 1157, 167–77, (1993)).

Supplementing culture media with vitamin $B_{12}$ may satisfy the need to produce coenzyme $B_{12}$ for glycerol dehydratase activity in many microorganisms, but in some cases additional catalytic activities may have to be added or increased in vivo. Enhanced synthesis of coenzyme $B_{12}$ in eukaryotes may be particularly desirable. Given the published sequences for genes encoding cob(I)alamin adenosyltransferase, the cloning and expression of this gene could be accomplished by one skilled in the art. For example, it is contemplated that yeast, such as Saccharomyces, could be constructed so as to contain genes encoding cob(I)alamin adenosyltransferase in addition to the genes necessary to effect conversion of a carbon substrate such as glucose to 1,3-propanediol. Cloning and expression of the genes for cobalt reduction requires a different approach. This could be based on a selection in *E. coli* for growth on ethanolamine as sole $N_2$ source. In the presence of coenzyme $B_{12}$ ethanolamine ammonia-lyase enables growth of cells in the absence of other $N_2$ sources. If *E. coli* cells contain a cloned gene for cob(I)alamin adenosyltransferase and random cloned DNA from another organism, growth on ethanolamine in the presence of aquacobalamin should be enhanced and selected for if the random cloned DNA encodes cobalt reduction properties to facilitate adenosylation of aquacobalamin.

Glycerol dehydratase is a multi-subunit enzyme consisting of three protein components which are arranged in an $a_2b_2g_2$ configuration (M. Seyfried et al, *J. Bacteriol.,* 5793–5796 (1996)). This configuration is an inactive apoenzyme which binds one molecule of coenzyme $B_{12}$ to become the catalytically active holo-enzyme. During catalysis, the holo-enzyme undergoes rapid, first order inactivation, to become an inactive complex in which the coenzyme $B_{12}$ has been converted to hydroxycobalamin (Z. Schneider and J. Pawelkiewicz, *ACTA Biochim. Pol.* 311–328 (1966)). Stoichiometric analysis of the reaction of glycerol dehydratase with glycerol as substrate revealed that each molecule of enzyme catalyzes 100,000 reactions before inactivation (Z. Schneider and J. Pawelkiewicz, *ACTA Biochim. Pol.* 311–328 (1966)). In vitro, this inactive complex can only be reactivated by removal of the hydroxycobalamin, by strong chemical treatment with magnesium and sulfite, and replacement with additional coenzyme $B_{12}$ (Z. Schneider et al., *J. Biol. Chem.* 3388–3396 (1970)). Inactivated glycerol dehydratase in wild type *Klebsiella pneumoniae* can be reactivated in situ (toluenized cells) in the presence of coenzyme $B_{12}$, adenosine 5'-triphosphate (ATP), and manganese (S. Honda et al, *J. Bacteriol.* 1458–1465 (1980)). This reactivation was shown to be due to the ATP dependent replacement of the inactivated cobalamin with coenzyme $B_{12}$ (K. Ushio et al.,*J. Nutr. Sci. Vitaminol.* 225–236 (1982)). Cell extract from toluenized cells which in situ catalyze the ATP, manganese, and coenzyme $B_{12}$ dependent reactivation are inactive with respect to this reactivation. Thus, without strong chemical reductive treatment or cell mediated replacement of the inactivated cofactor, glycerol dehydratase can only catalyzed 100,000 reactions per molecule.

The present invention demonstrates that the presence of protein X is important for in vivo reactivation of the dehydratase and the production of 1,3-propanediol is increased in a host cell capable of producing 1,3-propanediol in the presence of protein X. The present invention also discloses that the presence of protein 1, protein 2 and protein 3, in combination with protein X, also increased the production of 1,3-propanediol in a host cell capable of producing 1,3-propanediol.

In addition to *E. coli* and Saccharomyces, Klebsiella is a particularly preferred host. Strains of *Klebsiella pneumoniae* are known to produce 1,3-propanediol when grown on glycerol as the sole carbon. It is contemplated that Klebsiella can be genetically altered to produce 1,3-propanediol from monosaccharides, oligosaccharides, polysaccharides, or one-carbon substrates.

In order to engineer such strains, it will be advantageous to provide the Klebsiella host with the genes facilitating conversion of dihydroxyacetone phosphate to glycerol and conversion of glycerol to 1,3-propanediol either separately or together, under the transcriptional control of one or more constitutive or inducible promoters. The introduction of the DAR1 and GPP2 genes encoding glycerol-3-phosphate dehydrogenase and glycerol-3-phosphatase, respectively, will provide Klebsiella with genetic machinery to produce 1,3-propanediol from an appropriate carbon substrate.

The genes encoding protein X, protein 1, protein 2 and protein 3 or other enzymes associated with 1,3-propanediol production (e.g., G3PDH, G3P phosphatase, dhaB and/or dhaT) may be introduced on any plasmid vector capable of replication in *K. pneumoniae* or they may be integrated into the *K. pneumoniae* genome. For example, *K. pneumoniae* ATCC 25955 and *K. pneumoniae* ECL 2106 are known to be sensitive to tetracycline or chloramphenicol; thus plasmid vectors which are both capable of replicating in *K. pneumoniae* and encoding resistance to either or both of these antibiotics may be used to introduce these genes into *K. pneumoniae*. Methods of transforming Klebsiella with genes of interest are common and well known in the art and suitable protocols, including appropriate vectors and expression techniques may be found in Sambrook, supra.

Vectors and expression cassettes

The present invention provides a variety of vectors and transformation and expression cassettes suitable for the cloning, transformation and expression of protein X, protein 1, protein 2 and protein 3 as well as other proteins associated with 1,3-propanediol production, e.g., G3PDH and G3P phosphatase into a suitable host cell. Suitable vectors will be those which are compatible with the bacterium employed. Suitable vectors can be derived, for example, from a bacteria, a virus (such as bacteriophage T7 or a M-13 derived phage), a cosmid, a yeast or a plant. Protocols for obtaining and using such vectors are known to those in the art. (Sambrook et al., Molecular Cloning: A Laboratory Manual—volumes 1,2,3 (Cold Spring Harbor Laboratory, Cold Spring Harbor, N.Y., (1989)).

Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell although it is to be understood that such control regions need not be derived from the genes native to the specific species chosen as a production host.

Initiation control regions or promoters, which are useful to drive expression of the protein x and protein 1, protein 2 or protein 3 in the desired host cell, are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $IP_L$, $IP_R$, T7, tac, and trc (useful for expression in E. coli).

Termination control regions may also be derived from various genes native to the preferred hosts. Optionally, a termination site may be unnecessary, however, it is most preferred if included.

For effective expression of the instant enzymes, DNA encoding the enzymes are linked operably through initiation codons to selected expression control regions such that expression results in the formation of the appropriate messenger RNA.

Transformation of suitable hosts and expression of genes for the production of 1,3-propanediol Once suitable cassettes are constructed they are used to transform appropriate host cells. Introduction of the cassette containing dhaB activity, dhaB protein X and at least one of protein 1, protein 2 and protein 3 and optionally 1,3-propanediol oxidoreductase (dhaT), either separately or together, into the host cell may be accomplished by known procedures such as by transformation (e.g., using calcium-permeabilized cells, electroporation) or by transfection using a recombinant phage virus. (Sambrook et al., supra.). In the present invention, E. coli DH5a was transformed with dhaB subunits 1, 2 and 3 and dha protein X.

Additionally, E. coli W2042 (ATCC 98188) containing the genes encoding glycerol-3-phosphate dehydrogenase (G3PDH) and glycerol-3-phosphatase (G3P phosphatase), glycerol dehydratase (dhaB), and 1,3-propanediol oxidoreductase (dhaT) was created. Additionally, S. cerevisiae YPH500 (ATCC 74392) harboring plasmids pMCK10, pMCK17, pMCK30 and pMCK35 containing genes encoding glycerol-3-phosphate dehydrogenase (G3PDH) and glycerol-3-phosphatase (G3P phosphatase), glycerol dehydratase (dhaB), and 1,3-propanediol oxidoreductase (dhaT) was constructed. Both the above-mentioned transformed E. coli and Saccharomyces represent preferred embodiments of the invention.

Media and Carbon Substrates:

Fermentation media in the present invention must contain suitable carbon substrates. Suitable substrates may include but are not limited to monosaccharides such as glucose and fructose, oligosaccharides such as lactose or sucrose, polysaccharides such as starch or cellulose, or mixtures thereof, and unpurified mixtures from renewable feedstocks such as cheese whey permeate, cornsteep liquor, sugar beet molasses, and barley malt. Additionally, the carbon substrate may also be one-carbon substrates such as carbon dioxide, or methanol for which metabolic conversion into key biochemical intermediates has been demonstrated.

Glycerol production from single carbon sources (e.g., methanol, formaldehyde, or formate) has been reported in methylotrophic yeasts (Yamada et al., *Agric. Biol. Chem.*, 53(2) 541–543, (1989)) and in bacteria (Hunter et.al., *Biochemistry*, 24, 4148–4155, (1985)). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York (1986)). The ribulose monophosphate pathway involves the condensation of formate with ribulose-5-phosphate to form a 6 carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to utilization of one and two carbon substrates, methylotrophic organisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd..*, [Int. Symp.], 7th (1993), 415–32. Editor(s): Murrell, J. Collin; Kelly, Don P. Publisher: Intercept, Andover, UK). Similarly, various species of Candida will metabolize alanine or oleic acid (Sulter et al., *Arch. Microbiol.*, 153(5), 485–9 (1990)). Hence, the source of carbon utilized in the present invention may encompass a wide variety of carbon-containing substrates and will only be limited by the requirements of the host organism.

Although it is contemplated that all of the above mentioned carbon substrates and mixtures thereof are suitable in the present invention, preferred carbon substrates are monosaccharides, oligosaccharides, polysaccharides, and one-carbon substrates. More preferred are sugars such as glucose, fructose, sucrose and single carbon substrates such as methanol and carbon dioxide. Most preferred is glucose.

In addition to an appropriate carbon source, fermentation media must contain suitable minerals, salts, cofactors, buffers and other components, known to those skilled in the art, suitable for the growth of the cultures and promotion of the enzymatic pathway necessary for glycerol production. Particular attention is given to Co(II) salts and/or vitamin $B_{12}$ or precursors thereof.

Culture Conditions:

Typically, cells are grown at 30° C. in appropriate media. Preferred growth media in the present invention are common commercially prepared media such as Luria Bertani (LB) broth, Sabouraud Dextrose (SD) broth or Yeast Malt Extract (YM) broth. Other defined or synthetic growth media may also be used and the appropriate medium for growth of the particular microorganism will be known by someone skilled in the art of microbiology or fermentation science. The use of agents known to modulate catabolite repression directly or indirectly, e.g., cyclic adenosine 2':3'-monophosphate or cyclic adenosine 2':5'-monophosphate, may also be incorporated into the reaction media. Similarly, the use of agents known to modulate enzymatic activities (e.g., sulphites, bisulphites and alkalis) that lead to enhancement of glycerol production may be used in conjunction with or as an alternative to genetic manipulations.

Suitable pH ranges for the fermentation are between pH 5.0 to pH 9.0, where pH 6.0 to pH 8.0 is preferred as range for the initial condition.

Reactions may be performed under aerobic or anaerobic conditions where anaerobic or microaerobic conditions are preferred.

Batch and Continuous Fermentations:

The present process uses a batch method of fermentation. A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a batch fermentation is "batch" with respect to the addition of the carbon source and attempts are often made at controlling factors such as pH and oxygen concentration. The metabolite and biomass compositions of the batch system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch fermentation system which is also suitable in the present invention. In this variation of a typical batch system, the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

It is also contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

The present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1,3-propanediol production.

Alterations in the 1.3-propanediol production pathway:

Representative enzyme pathway. The production of 1,3-propanediol from glucose can be accomplished by the following series of steps. This series is representative of a number of pathways known to those skilled in the art. Glucose is converted in a series of steps by enzymes of the glycolytic pathway to dihydroxyacetone phosphate (DHAP) and 3-phosphoglyceraldehyde (3-PG). Glycerol is then formed by either hydrolysis of DHAP to dihydroxyacetone (DHA) followed by reduction, or reduction of DHAP to glycerol 3-phosphate (G3P) followed by hydrolysis. The hydrolysis step can be catalyzed by any number of cellular phosphatases which are known to be specific or non-specific with respect to their substrates or the activity can be introduced into the host by recombination. The reduction step can be catalyzed by a $NAD^+$ (or $NADP^+$) linked host enzyme or the activity can be introduced into the host by recombination. It is notable that the dha regulon contains a glycerol dehydrogenase (E.C. 1.1.1.6) which catalyzes the reversible reaction of Equation 3.

$$\text{Glycerol} \rightarrow \text{3-HP} + H_2O \quad \text{(Equation 1)}$$

$$\text{3-HP} + NADH + H^+ \rightarrow (\text{1,3-Propanediol}) + NAD^+ \quad \text{(Equation 2)}$$

$$\text{Glycerol} + NAD^+ \rightarrow \text{DHA} + NADH + H^+ \quad \text{(Equation 3)}$$

Glycerol is converted to 1,3-propanediol via the intermediate 3-hydroxypropionaldehye (3-HP) as has been described in detail above. The intermediate 3-HP is produced from glycerol (Equation 1) by a dehydratase enzyme which can be encoded by the host or can introduced into the host by recombination. This dehydratase can be glycerol dehydratase (E.C. 4.2.1.30), diol dehydratase (E.C. 4.2.1.28), or any other enzyme able to catalyze this transformation. Glycerol dehydratase, but not diol dehydratase, is encoded by the dha regulon. 1,3-Propanediol is produced from 3-HP (Equation 2) by a $NAD^+$- (or $NADP^+$) linked host enzyme or the activity can introduced into the host by recombination. This final reaction in the production of 1,3-propanediol can be catalyzed by 1,3-propanediol dehydrogenase (E.C. 1.1.1.202) or other alcohol dehydrogenases.

Mutations and transformations that affect carbon channeling. A variety of mutant organisms comprising variations in the 1,3-propanediol production pathway will be useful in the present invention. The introduction of a triosephosphate isomerase mutation (tpi-) into the microorganism is an example of the use of a mutation to improve the performance by carbon channeling. Alternatively, mutations which diminish the production of ethanol (adh) or lactate (ldh) will increase the availability of NADH for the production of 1,3-propanediol. Additional mutations in steps of glycolysis after glyceraldehyde-3-phosphate such as phosphoglycerate mutase (pgm) would be useful to increase the flow of carbon to the 1,3-propanediol production pathway. Mutations that effect glucose transport such as PTS which would prevent loss of PEP may also prove useful. Mutations which block alternate pathways for intermediates of the 1,3-propanediol production pathway such as the glycerol catabolic pathway (glp) would also be useful to the present invention. The mutation can be directed toward a structural gene so as to impair or improve the activity of an enzymatic activity or can be directed toward a regulatory gene so as to modulate the expression level of an enzymatic activity.

Alternatively, transformations and mutations can be combined so as to control particular enzyme activities for the enhancement of 1,3-propanediol production. Thus it is within the scope of the present invention to anticipate modifications of a whole cell catalyst which lead to an increased production of 1,3-propanediol.

Identification and purification of 1.3-propanediol:

Methods for the purification of 1,3-propanediol from fermentation media are known in the art. For example, propanediols can be obtained from cell media by subjecting the reaction mixture to extraction with an organic solvent, distillation and column chromatography (U.S. Pat. No. 5,356,812). A particularly good organic solvent for this process is cyclohexane (U.S. Pat. No. 5,008,473).

1,3-Propanediol may be identified directly by submitting the media to high pressure liquid chromatography (HPLC) analysis. Preferred in the present invention is a method where fermentation media is analyzed on an analytical ion exchange column using a mobile phase of 0.01 N sulfuric acid in an isocratic fashion.

Identification and purification of G3PDH and G3P phosphatase:

The levels of expression of the proteins G3PDH and G3P phosphatase are measured by enzyme assays, G3PDH activity assay relied on the spectral properties of the cosubstrate, NADH, in the DHAP conversion to G-3-P. NADH has intrinsic UV/vis absorption and its consumption can be monitored spectrophotometrically at 340 nm. G3P phosphatase activity can be measured by any method of measuring the inorganic phosphate liberated in the reaction. The most commonly used detection method used the visible spectroscopic determination of a blue-colored phosphomolybdate ammonium complex.

EXAMPLES

General Methods

Procedures for phosphorylations, ligations and transformations are well known in the art. Techniques suitable for use in the following examples may be found in Sambrook, J. et al., *Molecular Cloning: A Laboratory Manual*, Second Edition, Cold Spring Harbor Laboratory Press, Cold Spring Harbor, N.Y. (1989). Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC. (1994)) or by Thomas D. Brock in *Biotechnology: A Textbook of Industrial Microbiology*, Second Edition, Sinauer Associates, Inc., Sunderland, Mass. (1989). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Enzyme Assays

Glycerol dehydratase activity in cell-free extracts was determined using 1,2-propanediol as substrate. The assay, based on the reaction of aldehydes with methylbenzo-2-thiazolone hydrazone, has been described by Forage and Foster (*Biochim. Biophys. Acta,* 569, 249 (1979)). The activity of 1,3-propanediol oxidoreductase, sometimes referred to as 1,3-propanediol dehydrogenase, was determined in solution or in slab gels using 1,3-propanediol and $NAD^+$ as substrates as has also been described. Johnson and Lin, *J. Bacteriol.,* 169, 2050 (1987). NADH or NADPH dependent glycerol 3-phosphate dehydrogenase (G3PDH) activity was determined spectrophotometrically, following the disappearance of NADH or NADPH as has been described. (R. M. Bell and J. E. Cronan, Jr., *J. Biol. Chem.* 250:7153–8 (1975)).

Honda et al. (1980, In Situ Reactivation of Glycerol-Inactivated Coenzyme $B_{12}$-Dependent Enzymes, Glycerol Dehydratase and Diol Dehydratase. Journal of Bacteriology 143:1458–1465) disclose an assay that measures the reactivation of dehydratases.

Assay for glycerol-3-phosphatase, GPP

The assay for enzyme activity was performed by incubating the extract with an organic phosphate substrate in a bis-Tris or MES and magnesium buffer, pH 6.5. The substrate used was l-a-glycerol phosphate; d,l-a-glycerol phosphate. The final concentrations of the reagents in the assay are: buffer (20 mM, bis-Tris or 50 mM MES); $MgCl_2$ (10 mM); and substrate (20 mM). If the total protein in the sample was low and no visible precipitation occurs with an acid quench, the sample was conveniently assayed in the cuvette. This method involved incubating an enzyme sample in a cuvette that contained 20 mM substrate (50 mL, 200 mM), 50 mM MES, 10 mM $MgCl_2$, pH 6.5 buffer. The final phosphatase assay volume was 0.5 mL. The enzyme-containing sample was added to the reaction mixture; the contents of the cuvette were mixed and then the cuvette was placed in a circulating water bath at T=37° C. for 5 to 120 min—depending on whether the phosphatase activity in the enzyme sample ranged from 2 to 0.02 U/mL. The enzymatic reaction was quenched by the addition of the acid molybdate reagent (0.4 mL). After the Fiske SubbaRow reagent (0.1 mL) and distilled water (1.5 mL) were added, the solution was mixed and allowed to develop. After 10 min, the absorbance of the samples was read at 660 nm using a Cary 219 UV/Vis spectophotometer. The amount of inorganic phosphate released was compared to a standard curve that was prepared by using a stock inorganic phosphate solution (0.65 mM) and preparing 6 standards with final inorganic phosphate concentrations ranging from 0.026 to 0.130 mmol/mL.

Isolation and Identification 1,3-Propanediol

The conversion of glycerol to 1,3-propanediol was monitored by HPLC. Analyses were performed using standard techniques and materials available to one skilled in the art of chromatography. One suitable method utilized a Waters Maxima 820 HPLC system using UV (210 nm) and RI detection. Samples were injected onto a Shodex SH-1011 column (8 mm'300 mm, purchased from Waters, Milford, Mass.) equipped with a Shodex SH-1011 P precolumn (6 mm×50 mm), temperature controlled at 50° C., using 0.01 N $H_2SO_4$ as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of 1,3-propanediol was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated were compared to that of authentic 1,3-propanediol (m/e: 57, 58).

An alternative method for GC/MS involved derivatization of the sample. To 1.0 mL of sample (e.g., culture supernatant) was added 30 uL of concentrated (70% v/v) perchloric acid. After mixing, the sample was frozen and lyophilized. A 1:1 mixture of bis(trimethylsilyl) trifluoroacetamide:pyridine (300 uL) was added to the lyophilized material, mixed vigorously and placed at 65° C. for one h. The sample was clarified of insoluble material by centrifugation. The resulting liquid partitioned into two phases, the upper of which was used for analysis. The sample was chromatographed on a DB-5 column (48 m, 0.25 mm I.D., 0.25 urn film thickness; from J&W Scientific) and the retention time and mass spectrum of the 1,3-propanediol derivative obtained from culture supernatants were compared to that obtained from authentic standards. The mass spectrum of TMS-derivatized 1,3-propanediol contains the characteristic ions of 205, 177, 130 and 115 AMU.

Example 1

Cloning and Transformation of E. Coli Host Cells with Cosmid DNA for the Expression of 1.3-Propanediol Media Synthetic S12 medium was used in the screening of bacterial transformants for the ability to make 1,3-propanediol. S12 medium contains: 10 mM ammonium sulfate, 50 mM potassium phosphate buffer, pH 7.0, 2 mM $MgCl_2$, 0.7 mM $CaCl_2$, 50 uM $MnCl_2$, 1 uM $FeCl_3$, 1 uM ZnCl, 1.7 uM $CuSO_4$, 2.5 uM $CoCl_2$, 2.4 uM $Na_2MoO_4$, and 2 uM thiamine hydrochloride.

Medium A used for growth and fermentation consisted of: 10 mM ammonium sulfate; 50 mM MOPS/KOH buffer, pH 7.5; 5 mM potassium phosphate buffer, pH 7.5; 2 mM $MgCl_2$; 0.7 mM $CaCl_2$; 50 uM $MnCl_2$; 1 uM $FeCl_3$; 1 uM ZnCl; 1.72 uM $CuSO_4$; 2.53 uM $COCl_2$; 2.42 uM $Na_2MoO_4$; 2 uM thiamine hydrochloride; 0.01% yeast extract; 0.01% casamino acids; 0.8 ug/mL vitamin $B_{12}$; and 50 ug/mL amp. Medium A was supplemented with either 0.2% glycerol or 0.2% glycerol plus 0.2% D-glucose as required.

Cells:

Klebsiella pneumoniae ECL2106 (Ruch et al., J. Bacteriol., 124, 348 (1975)), also known in the literature as K. aerogenes or Aerobacter aerogenes, was obtained from E. C. C. Lin (Harvard Medical School, Cambridge, Mass.) and was maintained as a laboratory culture.

Klebsiella pneumoniae ATCC 25955 was purchased from American Type Culture Collection (Rockville, Md.).

E. coli DH5a was purchased from Gibco/BRL and was transformed with the cosmid DNA isolated from Klebsiella pneumoniae ATCC 25955 containing a gene coding for either a glycerol or diol dehydratase enzyme. Cosmids containing the glycerol dehydratase were identified as pKP1 and pKP2 and cosmid containing the diol dehydratase enzyme were identified as pKP4. Transformed DH5a cells were identified as DH5a-pKP1, DH5a-pKP2, and DH5a-pKP4.

E. coli ECL707 (Sprenger et al., J. Gen. Microbiol., 135, 1255 (1989)) was obtained from E. C. C. Lin (Harvard Medical School, Cambridge, Mass.) and was similarly transformed with cosmid DNA from Klebsiella pneumoniae. These transformants were identified as ECL707-pKP1 and ECL707-pKP2, containing the glycerol dehydratase gene and ECL707-pKP4 containing the diol dehydratase gene.

E. coli M200 containing a mutation in the tpi gene (Anderson et al., J. Gen Microbiol., 62, 329 (1970)) was purchased from the E. coli Genetic Stock Center, Yale University (New Haven, Conn.) and was transformed with Klebsiella cosmid DNA to give the recombinant organisms AA200-pKPI and AA200-pKP2, containing the glycerol dehydratase gene, and AA200-pKP4, containing the diol dehydratase gene.

DH5a:

Six transformation plates containing approximately 1,000 colonies of E. coli XL1-Blue MR transfected with K. pneumoniae DNA were washed with 5 mL LB medium and centrifuged. The bacteria were pelleted and resuspended in 5 mL LB medium+glycerol. An aliquot (50 uL) was inoculated into a 15 mL tube containing S12 synthetic medium with 0.2% glycerol+400 ng per mL of vitamin $B_{12}$+0.001% yeast extract +50amp. The tube was filled with the medium to the top and wrapped with parafilm and incubated at 30° C. A slight turbidity was observed after 48 h. Aliquots, analyzed for product distribution as described above at 78 h and 132 h, were positive for 1,3-propanediol, the later time points containing increased amounts of 1,3-propanediol.

The bacteria, testing positive for 1,3-propanediol production, were serially diluted and plated onto LB-50amp plates in order to isolate single colonies. Forty-eight single colonies were isolated and checked again for the production of 1,3-propanediol. Cosmid DNA was isolated from 6 independent clones and transformed into E. coli strain DH5a. The transformants were again checked for the production of 1,3-propanediol. Two transformants were characterized further and designated as DH5a-pKP1 and DH5a-pKP2.

A 12.1 kb EcoRI-SalI fragment from pKP1, subcloned into pIBI31 (IBI Biosystem, New Haven, Conn.), was sequenced and termed pHK28-26 (SEQ ID NO:19). Sequencing revealed the loci of the relevant open reading frames of the dha operon encoding glycerol dehydratase and genes necessary for regulation. Referring to SEQ ID NO:19, a fragment of the open reading frame for dhaK encoding dihydroxyacetone kinase is found at bases 1–399; the open reading frame dhaD encoding glycerol dehydrogenase is found at bases 983–2107; the open reading frame dhaR encoding the repressor is found at bases 2209–4134; the open reading frame dhaT encoding 1,3-propanediol oxidoreductase is found at bases 5017–6180; the open reading frame dhaB1 encoding the alpha subunit glycerol dehydratase is found at bases 7044–8711; the open reading frame dhaB2 encoding the beta subunit glycerol dehydratase is found at bases 8724–9308; the open reading frame dhaB3 encoding the gamma subunit glycerol dehydratase is found at bases 9311–9736; and the open reading frame dhaBX, encoding a protein of unknown function is found at bases 9749–11572.

Single colonies of E. coli XL1-Blue MR transfected with packaged cosmid DNA from K pneumoniae were inoculated into microtiter wells containing 200 uL of S15 medium (ammonium sulfate, 10 mM; potassium phosphate buffer, pH 7.0, 1 mM; MOPS/KOH buffer, pH 7.0, 50 mM; $MgCl_2$, 2 mM; $CaCl_2$, 0.7 mM; $MnCl_2$, 50 uM; $FeCl_3$, 1 uM; ZnCl, 1 uM; $CuSO_4$, 1.72 uM; $CoCl_2$, 2.53 uM; $Na_2MoO_4$, 2.42 uM; and thiamine hydrochloride, 2 uM)+0.2% glycerol+400 ng/mL of vitamin $B_{12}$+0.001% yeast extract +50 ug/mL ampicillin. In addition to the microtiter wells, a master plate containing LB-50 amp was also inoculated. After 96 h, 100 uL was withdrawn and centrifuged in a Rainin microfuge tube containing a 0.2 micron nylon membrane filter. Bacteria were retained and the filtrate was processed for HPLC analysis. Positive clones demonstrating 1,3-propanediol production were identified after screening approximately 240 colonies. Three positive clones were identified, two of which had grown on LB-50 amp and one of which had not. A single colony, isolated from one of the two positive clones grown on LB-50 amp and verified for the production of 1,3-propanediol, was designated as pKP4. Cosmid DNA was isolated from E. coli strains containing pKP4 and E. coli strain DH5a was transformed. An independent transformant, designated as DH5a-pKP4, was verified for the production of 1,3-propanediol.

ECL707:

E. coli strain ECL707 was transformed with cosmid K. pneumoniae DNA corresponding to one of pKP1, pKP2, pKP4 or the Supercos vector alone and named ECL707-pKP1, ECL707-pKP2, ECL707-pKP4, and ECL707-sc, respectively. ECL707 is defective in gipK, gld, and ptsD which encode the ATP-dependent glycerol kinase, NAD$^+$-linked glycerol dehydrogenase, and enzyme II for dihydroxyacetone of the phosphoenolpyruvate-dependent phosphotransferase system, respectively.

Twenty single colonies of each cosmid transformation and five of the Supercos vector alone (negative control) transformation, isolated from LB-50 amp plates, were transferred to a master LB-50 amp plate. These isolates were also tested for their ability to convert glycerol to 1,3-propanediol in order to determine if they contained dehydratase activity. The transformants were transferred with a sterile toothpick to microtiter plates containing 200 uL of Medium A supplemented with either 0.2% glycerol or 0.2% glycerol plus 0.2% D-glucose. After incubation for 48 hr at 30° C., the contents of the microtiter plate wells were filtered through an 0.45 micron nylon filter and chromatographed by HPLC. The results of these tests are given in Table 1.

TABLE 1

Conversion of glycerol to 1,3-propanediol by transformed ECL707

| Transformant | Glycerol* | Glycerol plus Glucose* |
|---|---|---|
| ECL707-pKP1 | 19/20 | 19/20 |
| ECL707-pKP2 | 18/20 | 20/20 |
| ECL707-pKP4 | 0/20 | 20/20 |
| ECL707-sc | 0/5 | 0/5 |

*(Number of positive isolates/number of isolates tested)

AA200:

E. coli strain AA200 was transformed with cosmid K. pneumoniae DNA corresponding to one of pKP1, pKP2, pKP4 and the Supercos vector alone and named AA200-pKP1, AA200-pKP2, AA200-pKP4, and AA200-sc, respectively. Strain AA200 is defective in triosephosphate isomerase (tpi$^-$).

Twenty single colonies of each cosmid transformation and five of the empty vector transformation were isolated and tested for their ability to convert glycerol to 1,3-propanediol as described for E. coli strain ECL707. The results of these tests are given in Table 2.

TABLE 2

Conversion of glycerol to 1,3-propanediol by transformed AA200

| Transformant | Glycerol* | Glycerol plus Glucose* |
|---|---|---|
| AA200-pKP1 | 17/20 | 17/20 |
| AA200-pKP2 | 17/20 | 17/20 |
| AA200-pKP4 | 2/20 | 16/20 |
| AA200-sc | 0/5 | 0/5 |

*(Number of positive isolates/number of isolates tested)

Example 2

Conversion of D-Glucose to 1,3-Propanediol by Recombinant E. coli Using DAR1, GPP2, dhaB, and dhaT Construction of general Purpose expression plasmids for use in transformation of Escherichia coli The expression vector pTacIQ The E. coli expression vector, pTacIQ, contains the lacIq gene (Farabaugh, Nature 274, 5673 (1978)) and tac promoter (Amann et al., Gene 25, 167 (1983)) inserted into the EcoRI of pBR322 (Sutcliffe et al., Cold Spring Harb. Symp. Quant. Biol. 43, 77 (1979)). A multiple cloning site and terminator sequence (SEQ ID NO:20) replaces the pBR322 sequence from EcoRI to SphI.

Subcloning the glycerol dehydratase genes (dhaB1, 2, 3)

The open reading frame for dhaB3 gene (incorporating an EcoRI site at the 5' end and a XbaI site at the 3' end) was amplified from pHK28-26 by PCR using primers (SEQ ID NOS:21 and 22). The product was subcloned into pLitmus29 (New England Biolab, Inc., Beverly, Mass.) to generate the plasmid pDHAB3 containing dhaB3.

The region containing the entire coding region for the four genes of the dhaB operon from pHK28-26 was cloned into pBluescriptII KS+ (Stratagene, La Jolla, Calif.) using the restriction enzymes KpnI and EcoRI to create the plasmid pM7.

The dhaBX gene was removed by digesting the plasmid pM7, which contains dhaB(1,2,3,4), with ApaI and XbaI (deleting part of dhaB3 and all of dhaBX). The resulting 5.9 kb fragment was purified and ligated with the 325-bp ApaI-XbaI fragment from plasmid pDHAB3 (restoring the dhaB3 gene) to create pM11, which contains dhaB(1,2,3).

The open reading frame for the dhaB1 gene (incorporating a HindIII site and a consensus RBS ribosome binding site at the 5' end and a XbaI site at the 3' end) was amplified from pHK28-26 by PCR using primers (SEQ ID NO:23 and SEQ ID NO:24). The product was subcloned into pLitmus28 (New England Biolab, Inc.) to generate the plasmid pDT1 containing dhaB1.

A NotI-XbaI fragment from pM11 containing part of the dhaB1 gene, the dhaB2 gene and the dhaB3 gene was inserted into pDT1 to create the dhaB expression plasmid, pDT2. The HindIII-XbaI fragment containing the dhaB(1, 2,3) genes from pDT2 was inserted into pTacIQ to create pDT3.

Subcloninq the 1,3-propanediol dehydrogenase gene (dhaT)

The KpnI-SacI fragment of pHK28-26, containing the complete 1,3-propanediol dehydrogenase (dhaT) gene, was subcloned into pBluescriptII KS+ creating plasmid pAH1. The dhaT gene (incorporating an XbaI site at the 5' end and a BamHI site at the 3' end) was amplified by PCR from pAH1 as template DNA using synthetic primers (SEQ ID NO:25 with SEQ ID NO:26). The product was subcloned into pCR-Script (Stratagene) at the SrfI site to generate the plasmids pAH4 and pAH5 containing dhaT. The plasmid pAH4 contains the dhaT gene in the correct orientation for expression from the lac promoter in pCR-Script and pAH5 contains the dhaT gene in the opposite orientation. The XbaI-BamHI fragment from pAH4 containing the dhaT gene was inserted into pTacIQ to generate plasmid pAH8. The HindIII-BamHI fragment from pAH8 containing the RBS and dhaT gene was inserted into pBluescriptII KS+ to create pAH11. The HindIII-SalI fragment from pAH8 containing the RBS, dhaT gene and terminator was inserted into pBluescriptII SK+ to create pAH12.

Construction of an expression cassette for dhaB(1,2,3) and dhaT

An expression cassette for the dhaB(1,2,3) and dhaT was assembled from the individual dhaB(1,2,3) and dhaT subclones described above using standard molecular biology methods. The SpeI-KpnI fragment from pAH8 containing the RBS, dhaT gene and terminator was inserted into the XbaI-KpnI sites of pDT3 to create pAH23. The SmaI-EcoRI fragment between the dhaB3 and dhaT gene of pAH23 was removed to create pAH26. The SpeI-NotI fragment containing an EcoRI site from pDT2 was used to replace the SpeI-NotI fragment of pAH26 to generate pAH27.

Construction of expression cassette for dhaT and dhaB(1,2,3)

An expression cassette for dhaT and dhaB(1,2,3) was assembled from the individual dhaB(1,2,3) and dhaT subclones described previously using standard molecular biology methods. A SpeI-SacI fragment containing the dhaB(1,2,3) genes from pDT3 was inserted into pAH11 at the SpeI-SacI sites to create pAH24.

Cloning and expression of glycerol 3-phosphatase for increased glycerol production in E. coli The Saccharomyces cerevisiae chromosome V lamda clone 6592 (Gene Bank, accession # U18813×11) was obtained from ATCC. The glycerol 3-phosphate phosphatase (GPP2) gene (incorporating an BamHI-RBS-XbaI site at the 5' end and a SmaI site at the 3' end) was cloned by PCR cloning from the lamda clone as target DNA using synthetic primers (SEQ ID NO:27 with SEQ ID NO:28). The product was subcloned into pCR-Script (Stratagene) at the SrfI site to generate the plasmids pAH15 containing GPP2. The plasmid pAH15 contains the GPP2 gene in the inactive orientation for expression from the lac promoter in pCR-Script SK+. The BamHI-SmaI fragment from pAH15 containing the GPP2 gene was inserted into pBlueScriptII SK+ to generate plasmid pAH19. The pAH19 contains the GPP2 gene in the correct orientation for expression from the lac promoter. The XbaI-PstI fragment from pAH19 containing the GPP2 gene was inserted into pPHOX2 to create plasmid pAH21.

Plasmids for the expression of dhaT, dhaB(1,2,3) and GPP2 genes

A SalI-EcoRI-XbaI linker (SEQ ID NOS:29 and 30) was inserted into pAH5 which was digested with the restriction enzymes, SalI-XbaI to create pDT16. The linker destroys the XbaI site. The 1 kb SalI-MluI fragment from pDT16 was then inserted into pAH24 replacing the existing SalI-MluI fragment to create pDT18.

The 4.1 kb EcoRI-XbaI fragment containing the expression cassette for dhaT and dhaB(1,2,3) from pDT18 and the 1.0 kb XbaI-SalI fragment containing the GPP2 gene from pAH21 was inserted into the vector pMMB66EH (Fuste et al., GENE, 48, 119 (1986)) digested with the restriction enzymes EcoRI and SalI to create pDT20.

Plasmids for the over-expression of DAR1 in E. coli

DAR1 was isolated by PCR cloning from genomic S. cerevisiae DNA using synthetic primers (SEQ ID NO:46 with SEQ ID NO:47). Successful PCR cloning places an NcoI site at the 5' end of DAR1 where the ATG within NcoI is the DAR1 initiator methionine. At the 3' end of DAR1 a BamHI site is introduced following the translation terminator. The PCR fragments were digested with NcoI+BamHI and cloned into the same sites within the expression plasmid pTrc99A (Pharmacia, Piscataway, N.J.) to give pDAR1A.

In order to create a better ribosome binding site at the 5' end of DAR1, a SpeI-RBS-NcoI linker obtained by annealing synthetic primers (SEQ ID NO:48 with SEQ ID NO:49) was inserted into the NcoI site of pDAR1A to create pAH40. Plasmid pAH40 contains the new RBS and DAR1 gene in the correct orientation for expression from the trc promoter of Trc99A (Pharmacia). The NcoI-BamHI fragment from pDAR1A and a second set of SpeI-RBS-NcoI linker obtained by annealing synthetic primers (SEQ ID NO:31 with SEQ ID NO:32) was inserted into the SpeI-BamHI site of pBluescript II-SK+(Stratagene) to create pAH41. The construct pAH41 contains an ampicillin resistance gene. The NcoI-BamHI fragment from pDAR1A and a second set of SpeI-RBS-NcoI linker obtained by annealing synthetic primers (SEQ ID NO:31 with SEQ ID NO:32) was inserted into the SpeI-BamHI site of pBC-SK+(Stratagene) to create pAH42. The construct pAH42 contains a chloroamphenicol resistance gene.

Construction of an expression cassette for DAR1 and GPP2

An expression cassette for DAR1 and GPP2 was assembled from the individual DAR1 and GPP2 subcdones described above using standard molecular biology methods. The BamHI-Pst1 fragment from pAH19 containing the RBS and GPP2 gene was inserted into pAH40 to create pAH43. The BamHI-Pst1 fragment from pAH19 containing the RBS and GPP2 gene was inserted into pAH41 to create pAH44. The same BamHI-PstI fragment from pAH19 containing the RBS and GPP2 gene was also inserted into pAH42 to create pAH45.

The ribosome binding site at the 5' end of GPP2 was modified as follows. A BamHI-RBS-SpeI linker, obtained by annealing synthetic primers GATCCAGGAAACAGA with CTAGTCTGTTTCCTG to the XbaI-PstI fragment from pAH19 containing the GPP2 gene, was inserted into the BamHI-PstI site of pAH40 to create pAH48. Plasmid pAH48 contains the DAR1 gene, the modified RBS, and the GPP2 gene in the correct orientation for expression from the trc promoter of pTrc99A (Pharmacia, Piscataway, N.J.).

E. coli strain construction

E. coli W1485 is a wild-type K-12 strain (ATCC 12435). This strain was transformed with the plasmids pDT20 and pAH42 and selected on LA (Luria Agar, Difco) plates supplemented with 50 mg/mL carbencillim and 10 mg/mL chloramphenicol.

Production of 1,3-propanediol from glucose

E. coli W1485/pDT20/pAH42 was transferred from a plate to 50 mL of a medium containing per liter: 22.5 g glucose, 6.85 g $K_2HPO_4$, 6.3 g $(NH_4)_2SO_4$, 0.5 g $NaHCO_3$, 2.5 g NaCl, 8 g yeast extract, 8 g tryptone, 2.5 mg vitamin $B_{12}$, 2.5 mL modified Balch's trace-element solution, 50 mg carbencillim and 10 mg chloramphenicol, final pH 6.8 (HCl), then filter sterilized. The composition of modified Balch's trace-element solution can be found in Methods for General and Molecular Bacteriology (P. Gerhardt et al., eds, p. 158, American Society for Microbiology, Washington, DC (1994)). After incubating at 37° C., 300 rpm for 6 h, 0.5 g glucose and IPTG (final concentration=0.2 mM) were added and shaking was reduced to 100 rpm. Samples were analyzed by GC/MS. After 24 h, W1485/pDT20/pAH42 produced 1.1 g/L glycerol and 195 mg/L 1,3-propanediol.

Example 3

Cloning and Expression of dhaB and dhaT in Saccharomyces cerevisiae

Expression plasmids that could exist as replicating episomal elements were constructed for each of the four dha genes. For all expression plasmids a yeast ADH1 promoter was present and separated from a yeast ADH1 transcription terminator by fragments of DNA containing recognition sites for one or more restriction endonucleases. Each expression plasmid also contained the gene for b-lactamase for selection in E. coli on media containing ampicillin, an origin of replication for plasmid maintenance in E. coli, and a 2 micron origin of replication for maintenance in S. cerevisiae. The selectable nutritional markers used for yeast and present on the expression plasmids were one of the following: HIS3 gene encoding imidazoleglycerolphosphate dehydratase, URA3 gene encoding orotidine 5'-phosphate decarboxylase, TRP1 gene encoding N-(5'-phosphoribosyl)-anthranilate isomerase, and LEU2 encoding b-isopropylmalate dehydrogenase.

The open reading frames for dhaT, dhaB3, dhaB2 and dhaB1 were amplified from pHK28-26 (SEQ ID NO:19) by PCR using primers (SEQ ID NO:38 with SEQ ID NO:39, SEQ ID NO:40 with SEQ ID NO:41, SEQ ID NO:42 with SEQ ID NO:43, and SEQ ID NO:44 with SEQ ID NO:45 for dhaT, dhaB3, dhaB2 and dhaB1, respectively) incorporating EcoR1 sites at the 5' ends (10 mM Tris pH 8.3, 50 mM KCl, 1.5 mM $MgCl_2$, 0.0001% gelatin, 200 mM dATP, 200 mM dCTP, 200 mM dGTP, 200 mM dTTP, 1 mM each primer, 1–10 ng target DNA, 25 units/mL Amplitaqa DNA polymerase (Perkin-Elmer Cetus, Norwalk Conn.)). PCR parameters were 1 min at 94° C., 1 min at 55° C., 1 min at 72° C., 35 cycles. The products were subcloned into the EcoR1 site of pHIL-D4 (Phillips Petroleum, Bartlesville, Okla.) to generate the plasmids pMP13, pMP14, pMP20 and pMP15 containing dhaT, dhaB3, dhaB2 and dhaB1, respectively.

Construction of dhaB1 expression plasmid pMCK10

The 7.8 kb replicating plasmid pGADGH (Clontech, Palo Alto, Calif.) was digested with HindIII, dephosphorylated, and ligated to the dhaB1 HindIII fragment from pMP15. The resulting plasmid (pMCK10) had dhaB1 correctly oriented for transcription from the ADH1 promoter and contained a LEU2 marker.

Construction of dhaB2 expression plasmid PMCK17

Plasmid pGADGH (Clontech, Palo Alto, Calif.) was digested with HindIII and the single-strand ends converted to EcoRI ends by ligation with HindIII-XmnI and EcoRI-XmnI adaptors (New England Biolabs, Beverly, Mass.). Selection for plasmids with correct EcoRI ends was achieved by ligation to a kanamycin resistance gene on an EcoRI fragment from plasmid pUC4K (Pharmacia Biotech, Uppsala), transformation into *E. coli* strain DH5a and selection on LB plates containing 25 mg/mL kanamycin. The resulting plasmid (pGAD/KAN2) was digested with SnaBI and EcoRI and a 1.8 kb fragment with the ADHI promoter was isolated. Plasmid pGBT9 (Clontech, Palo Alto, Calif.) was digested with SnaBI and EcoRI, and the 1.5 kb ADH1/GAL4 fragment replaced by the 1.8 kb ADH1 promoter fragment isolated from pGAD/KAN2 by digestion with SnaBI and EcoRI. The resulting vector (pMCK1 1) is a replicating plasmid in yeast with an ADHI promoter and terminator and a TRP1 marker. Plasmid pMCK1 1 was digested with EcoRI, dephosphorylated, and ligated to the dhaB2 EcoRI fragment from pMP20. The resulting plasmid (pMCK1 7) had dhaB2 correctly oriented for transcription from the ADH 1 promoter and contained a TRP1 marker.

Construction of dhaB3 expression plasmid pMCK30

Plasmid pGBT9 (Clontech) was digested with NaeI and PvuII and the 1 kb TRP1 gene removed from this vector. The TRPI gene was replaced by a URA3 gene donated as a 1.7 kb AatII/NaeI fragment from plasmid pRS406 (Stratagene) to give the intermediary vector pMCK32. The truncated ADH1 promoter present on pMCK32 was removed on a 1.5 kb SnaBI/EcoRI fragment, and replaced with a full-length ADH1 promoter on a 1.8 kb SnaBI/EcoRI fragment from plasmid pGAD/KAN2 to yield the vector pMCK26. The unique EcoRI site on pMCK26 was used to insert an EcoRI fragment with dhaB3 from plasmid pMP14 to yield pMCK30. The pMCK30 replicating expression plasmid has dhaB3 orientated for expression from the ADH1 promoter, and has a URA3 marker.

Construction of dhaT expression plasmid pMCK35

Plasmid pGBT9 (Clontech) was digested with NaeI and PvuII and the 1 kb TRP1 gene removed from this vector. The TRPI gene was replaced by a HIS3 gene donated as an XmnI/NaeI fragment from plasmid pRS403 (Stratagene) to give the intermediary vector pMCK33. The truncated ADH1 promoter present on pMCK33 was removed on a 1.5 kb SnaBI/EcoRI fragment, and replaced with a full-length ADH1 promoter on a 1.8 kb SnaBI/EcoRI fragment from plasmid pGAD/KAN2 to yield the vector pMCK31. The unique EcoRI site on pMCK31 was used to insert an EcoRI fragment with dhaT from plasmid pMP13 to yield pMCK35. The pMCK35 replicating expression plasmid has dhaT orientated for expression from the ADH1 promoter, and has a HIS3 marker.

Transformation of *S. cerevisiae* with dha expression plasmids

*S. cerevisiae* strain YPH500 (ura3-52 lys2-801 ade2-101 trp1-D63 his3-D200 leu2-D1) (Sikorski R. S. and Hieter P., *Genetics* 122, 19–27, (1989)) purchased from Stratagene (La Jolla, Calif.) was transformed with 1–2 mg of plasmid DNA using a Frozen-EZ Yeast Transformation Kit (Catalog #T2001) (Zymo Research, Orange, Calif.). Colonies were grown on Supplemented Minimal Medium (SMM—0.67% yeast nitrogen base without amino acids, 2% glucose) for 3–4 d at 29° C. with one or more of the following additions: adenine sulfate (20 mg/L), uracil (20 mg/L), L-tryptophan (20 mg/L), L-histidine (20 mg/L), L-leucine (30 mg/L), L-lysine (30 mg/L). Colonies were streaked on selective plates and used to inoculate liquid media.

Screening of *S. cerevisiae* transformants for dha genes

Chromosomal DNA from $URA^+$, $HIS^+$, $TRP^+$, $LEU^+$ transformants was analyzed by PCR using primers specific for each gene (SEQ ID NOS:38–45). The presence of all four open reading frames was confirmed.

Expression of dhaB and dhaT activity in transformed *S. cerevisiae*

The presence of active glycerol dehydratase (dhaB) and 1,3-propanediol oxido-reductase (dhaT) was demonstrated using in vitro enzyme assays. Additionally, western blot analysis confirmed protein expression from all four open reading frames.

Strain YPH500, transformed with the group of plasmids pMCK10, pMCK17, pMCK30 and pMCK35, was grown on Supplemented Minimal Medium containing 0.67% yeast nitrogen base without amino acids 2% glucose 20 mg/L adenine sulfate, and 30 mg/L L-lysine. Cells were homogenized and extracts assayed for dhaB activity. A specific activity of 0.12 units per mg protein was obtained for glycerol dehydratase, and 0.024 units per mg protein for 1,3-propanediol oxido-reductase.

Example 4

Production of 1,3-Propanediol from D-Glucose Using Recombinant *Saccharomyces cerevisiae*

*S. cerevisiae* YPH500, harboring the groups of plasmids pMCK10, pMCK17, pMCK30 and pMCK35, was grown in a BiostatB fermenter (B Braun Biotech, Inc.) in 1.0 L of minimal medium initially containing 20 g/L glucose, 6.7 g/L yeast nitrogen base without amino acids, 40 mg/L adenine sulfate and 60 mg/L L-lysine.HCl. During the course of the growth, an additional equivalent of yeast nitrogen base, adenine and lysine was added. The fermenter was controlled at pH 5.5 with addition of 10% phosphoric acid and 2 M NaOH, 30° C., and 40% dissolved oxygen tension through agitation control. After 38 h, the cells ($OD_{600}$=5.8 AU) were harvested by centrifugation and resuspended in base medium (6.7 g/L yeast nitrogen base without amino acids, 20 mg/L adenine sulfate, 30 mg/L L-lysine.HCl, and 50 mM potassium phosphate buffer, pH 7.0).

Reaction mixtures containing cells ($OD_{600}$=20 AU) in a total volume of 4 mL of base media supplemented with 0.5% glucose, 5 ug/mL coenzyme $B_{12}$ and 0, 10, 20, or 40 mM chloroquine were prepared, in the absence of light and oxygen (nitrogen sparging), in 10 mL crimp sealed serum bottles and incubated at 30° C. with shaking. After 30 h, aliquots were withdrawn and analyzed by HPLC. The results are shown in the Table 3.

TABLE 3

Production of 1,3-propanediol using recombinant S. cerevisiae

| reaction | chloroquine (mM) | 1,3-propanediol (mM) |
| --- | --- | --- |
| 1 | 0 | 0.2 |
| 2 | 10 | 0.2 |
| 3 | 20 | 0.3 |
| 4 | 40 | 0.7 |

Example 5

Use of a S. cerevisiae Double Transformant for Production of 1,3-Propanediol From D-Glucose where dhaB and dhaT are Integrated into the Genome Example 5 prophetically demonstrates the transformation of S. cerevisiae with dhaB1, dhaB2, dhaB3, and dhaT and the stable integration of the genes into the yeast genome for the production of 1,3-propanediol from glucose.
Construction of expression cassettes Four expression cassettes (dhaB1, dhaB2, dhaB3, and dhaT) are constructed for glucose-induced and high-level constitutive expression of these genes in yeast, Saccharomyces cerevisiae. These cassettes consist of: (i) the phosphoglycerate kinase (PGK) promoter from S. cerevisiae strain S288C; (ii) one of the genes dhaB1, dhaB2, dhaB3, or dhaT, and (iii) the PGK terminator from S. cerevisiae strain S288C. The PCR-based technique of gene splicing by overlap extension (Horton et al., BioTechniques, 8:528–535, (1990)) is used to recombine DNA sequences to generate these cassettes with seamless joints for optimal expression of each gene. These cassettes are cloned individually into a suitable vector (pLITMUS 39) with restriction sites amenable to multi-cassette cloning in yeast expression plasmids.
Construction of yeast integration vectors Vectors used to effect the integration of expression cassettes into the yeast genome are constructed. These vectors contain the following elements: (i) a polycloning region into which expression cassettes are subcloned; (ii) a unique marker used to select for stable yeast transformants; (iii) replication origin and selectable marker allowing gene manipulation in E. coli prior to transforming yeast. One integration vector contains the URA3 auxotrophic marker (Ylp352b), and a second integration vector contains the LYS2 auxotrophic marker (pKP7).
Construction of yeast expression plasmids Expression cassettes for dhaB1 and dhaB2 are subcloned into the polycloning region of the Ylp352b (expression plasmid #1), and expression cassettes for dhaB3 and dhaT are subcloned into the polycloning region of pKP7 (expression plasmid #2).
Transformation of yeast with expression plasmids S. cerevisiae (ura3, lys2) is transformed with expression plasmid #1 using Frozen-EZ Yeast Transformation kit (Zymo Research, Orange, Calif.), and transformants selected on plates lacking uracil. Integration of expression cassettes for dhaB1 and dhaB2 is confirmed by PCR analysis of chromosomal DNA. Selected transformants are re-transformed with expression plasmid #2 using Frozen-EZ Yeast Transformation kit, and double transformants selected on plates lacking lysine. Integration of expression cassettes for dhaB3 and dhaT is confirmed by PCR analysis of chromosomal DNA. The presence of all four expression cassettes (dhaB1, dhaB2, dhaB3, dhaT) in double transformants is confirmed by PCR analysis of chromosomal DNA.
Protein production from double-transformed yeast Production of proteins encoded by dhaB1, dhaB2, dhaB3 and dhaT from double-transformed yeast is confirmed by Western blot analysis.
Enzyme activity from double-transformed yeast Active glycerol dehydratase and active 1,3-propanediol dehydrogenase from double-transformed yeast is confirmed by enzyme assay as described in General Methods above.
Production of 1,3-propanediol from double-transformed yeast Production of 1,3-propanediol from glucose in double-transformed yeast is demonstrated essentially as described in Example 4.

Example 6

Construction of Plasmids Containing DAR1/GPP2 or dhaT/dhaB1–3 and Transformation into Klebsiella Species K. pneumoniae (ATCC 25955), K. pneumoniae (ECL2106), and K. oxytoca (ATCC 8724) are naturally resistant to ampicillin (up to 150 ug/mL) and kanamycin (up to 50 ug/mL), but sensitive to tetracycline (10 ug/mL) and chloramphenicol (25 ug/mL). Consequently, replicating plasmids which encode resistance to these latter two antibiotics are potentially useful as cloning vectors for these Klebsiella strains. The wild-type K. pneumoniae (ATCC 25955), the glucose-derepressed K. pneumonia (ECL2106), and K. oxytoca (ATCC 8724) were successfully transformed to tetracycline resistance by electroporation with the moderate-copy-number plasmid, pBR322 (New England Biolabs, Beverly, Mass.). This was accomplished by the following procedure: Ten mL of an overnight culture was inoculated into 1 L LB (1% (w/v) Bacto-tryptone (Difco, Detroit, Mich.), 0.5% (w/v) Bacto-yeast extract (Difco) and 0.5% (w/v) NaCl (Sigma, St. Louis, Mo.) and the culture was incubated at 37° C. to an $OD_{600}$ of 0.5–0.7. The cells were chilled on ice, harvested by centrifugation at 4000× g for 15 min, and resuspended in 1 L ice-cold sterile 10% glycerol. The cells were repeatedly harvested by centrifugation and progressively resuspended in 500 mL, 20 mL and, finally, 2 mL ice-cold sterile 10% glycerol. For electroporation, 40 uL of cells were mixed with 1–2 uL DNA in a chilled 0.2 cm cuvette and were pulsed at 200 Ω, 2.5 kV for 4–5 msec using a BioRad Gene Pulser (BioRad, Richmond, Calif.). One mL of SOC medium (2% (w/v) Bacto-tryptone (Difco), 0.5% (w/v) Bacto-yeast extract (Difco), 10 mM NaCl, 10 mM $MgCl_2$, 10 mM $MgSO_4$, 2.5 mM KCl and 20 mM glucose) was added to the cells and, after the suspension was transferred to a 17×100 mm sterile polypropylene tube, the culture was incubated for 1 hr at 37° C., 225 rpm. Aliquots were plated on selective medium, as indicated. Analyses of the plasmid DNA from independent tetracycline-resistant transformants showed the restriction endonuclease digestion patterns typical of pBR322, indicating that the vector was stably maintained after overnight culture at 37° C. in LB containing tetracycline (10 ug/mL). Thus, this vector, and derivatives such as pBR329 (ATCC 37264) which encodes resistance to ampicillin, tetracycline and chloramphenicol, may be used to introduce the DAR1/GPP2 and dhaT/dhaB1–3 expression cassettes into K. pneumoniae and K. oxytoca.

The DAR1 and GPP2 genes may be obtained by PCR-mediated amplification from the Saccharomyces cerevisiae genome, based on their known DNA sequence. The genes are then transformed into K. pneumoniae or K. oxytoca under the control of one or more promoters that may be used to direct their expression in media containing glucose. For convenience, the genes were obtained on a 2.4 kb DNA fragment obtained by digestion of plasmid pAH44 with the PvuII restriction endonuclease, whereby the genes are already arranged in an expression cassette under the control of the E. coli lac promoter. This DNA fragment was ligated to PvuII-digested pBR329, producing the insertional inactivation of its chloramphenicol resistance gene. The ligated DNA was used to transform E. coli DH5α (Gibco, Gaithersberg, Md.). Transformants were selected by their resistance to tetracycline (10 ug/mL) and were screened for their sensitivity to chloramphenicol (25 ug/mL). Analysis of the plasmid DNA from tetracycline-resistant, chloramphenicol-sensitive transformants confirmed the presence of the expected plasmids, in which the $P_{lac}$-dar1-gpp$^2$ expression cassette was subcloned in either orientation into the pBR329 PvuII site. These plasmids, designated pJSP1A (clockwise orientation) and pJSP1B (counterclockwise orientation), were separately transformed by electroporation into K. pneumonia (ATCC 25955), K. pneumonia (ECL2106) and K. oxytoca (ATCC 8724) as described. Transformants were selected by their resistance to tetracycline (10 ug/mL) and were screened for their sensitivity to chloramphenicol (25 ug/mL). Restriction analysis of the plasmids isolated from independent transformants showed only the expected digestion patterns, and confirmed that they were stably maintained at 37° C. with antibiotic selection. The expression of the DAR1 and GPP2 genes may be enhanced by the addition of IPTG (0.2–2.0 mM) to the growth medium.

The four K. pneumoniae dhaB(1–3) and dhaT genes may be obtained by PCR-mediated amplification from the K. pneumoniae genome, based on their known DNA sequence. These genes are then transformed into K. pneumoniae under the control of one or more promoters that may be used to direct their expression in media containing glucose. For convenience, the genes were obtained on an approximately 4.0 kb DNA fragment obtained by digestion of plasmid pAH24 with the KpnI/SacI restriction endonucleases, whereby the genes are already arranged in an expression cassette under the control of the E. coli lac promoter. This DNA fragment was ligated to similarly digested pBC-KS+ (Stratagene, La Jolla, Calif.) and used to transform E. coli DH5α. Transformants were selected by their resistance to chloramphenicol (25 ug/mL) and were screened for a white colony phenotype on LB agar containing X-gal. Restriction analysis of the plasmid DNA from chloramphenicol-resistant transformants demonstrating the white colony phenotype confirmed the presence of the expected plasmid, designated pJSP2, in which the dhaT-dhaB(1-3) genes were subcloned under the control of the E. coli lac promoter.

To enhance the conversion of glucose to 1,3-propanediol, this plasmid was separately transformed by electroporation into K. pneumoniae (ATCC 25955) (pJSP1A), K. pneumoniae (ECL2106) (pJSP1A) and K oxytoca (ATCC 8724) (pJSP1A) already containing the $P_{lac}$-dar1-gpp2 expression cassette. Cotransformants were selected by their resistance to both tetracycline (10 ug/mL) and chloramphenicol (25 ug/mL). Restriction analysis of the plasmids isolated from independent cotransformants showed the digestion patterns expected for both pJSP1A and pJSP2. The expression of the DAR1, GPP2, dhaB(1–3), and dhaT genes may be enhanced by the addition of IPTG (0.2–2.0 mM) to the medium.

Example 7

Production of 1,3 Propanediol from Glucose by K. pneumoniae

Klebsiella pneumoniae strains ECL 2106 and 2106-47, both transformed with pJSP1A, and ATCC 25955, transformed with pJSP1A and pJSP2, were grown in a 5 L Applikon fermenter under various conditions (see Table 4) for the production of 1,3-propanediol from glucose. Strain 2104-47 is a fluoroacetate-tolerant derivative of ECL 2106 which was obtained from a fluoroacetate/lactate selection plate as described in Bauer et al., Appl. Environ. Microbiol. 56, 1296 (1990). In each case, the medium used contained 50–100 mM potassium phosphate buffer, pH 7.5, 40 mM $(NH_4)_2SO_4$, 0.1% (w/v) yeast extract, 10 $\mu$M $CoCl_2$, 6.5 $\mu$M $CuCl_2$, 100 $\mu$M $FeCl_3$, 18 $\mu$M $FeSO_4$, 5 $\mu$M $H_3BO_3$, 50 $\mu$M $MnCl_2$, 0.1 $\mu$M $Na_2MoO_4$, 25 $\mu$M $ZnCl_2$, 0.82 mM $MgSO_4$, 0.9 mM $CaCl_2$, and 10–20 g/L glucose. Additional glucose was fed, with residual glucose maintained in excess. Temperature was controlled at 37° C. and pH controlled at 7.5 with 5N KOH or NaOH. Appropriate antibiotics were included for plasmid maintenance; IPTG (isopropyl-b-D-thiogalactopyranoside) was added at the indicated concentrations as well. For anaerobic fermentations, 0.1 vvm nitrogen was sparged through the reactor; when the dO setpoint was 5%, 1 vvm air was sparged through the reactor and the medium was supplemented with vitamin B12. Final concentrations and overall yields (g/g) are shown in Table 4.

TABLE 4

Production of 1,3 propanediol from glucose by K. pneumoniae

| Organism | dO | IPTG, mM | vitamin B12, mg/L | Titer, g/L | Yield, g/g |
|---|---|---|---|---|---|
| 25955[pJSP1A/pJSP2] | 0 | 0.5 | 0 | 8.1 | 16% |
| 25955[pJSP1A/pJSP2] | 5% | 0.2 | 0.5 | 5.2 | 4% |
| 2106[pJSP1A] | 0 | 0 | 0 | 4.9 | 17% |
| 2106[pJSP1A] | 5% | 0 | 5 | 6.5 | 12% |
| 2106-47[pJSP1A] | 5% | 0.2 | 0.5 | 10.9 | 12% |

Example 8

Conversion of Carbon Substrates to 1,3-Propanediol by Recombinant K. pneumoniae containing dar1, gpp2, dhaB, and dhaT A. Conversion of D-fructose to 1,3-propanediol by various K. pneumoniae recombinant strains:

Single colonies of K. pneumoniae (ATCC 25955 pJSP1A), K. pneumoniae (ATCC 25955 pJSP1A/pJSP2), K. pneumoniae (ATCC 2106 pJSP1A), and K. pneumoniae (ATCC 2106 pJSP1A/pJSP2) were transferred from agar plates and in separate culture tubes were subcultured overnight in Luria-Bertani (LB) broth containing the appropriate antibiotic agent(s). A 50-mL flask containing 45 mL of a steri-filtered minimal medium defined as LLMM/F which contains per liter: 10 g fructose; 1 g yeast extract; 50 mmoles potassium phosphate, pH 7.5; 40 mmoles $(NH_4)_2SO_4$; 0.09 mmoles calcium chloride; 2.38 mg $CoCl_2.6H_2O$; 0.88 mg CuCl$_2$.2H$_2$O; 27 mg FeCl$_3$.6H$_2$O; 5 mg FeSO$_4$.7H$_2$O; 0.31 mg H$_3$BO$_3$; 10 mg MnCl$_2$.4H$_2$O; 0.023 mg Na$_2$MoO$_4$.2H$_2$O; 3.4 mg ZnCl$_2$; 0.2 g MgSO4.7H$_2$O. Tetracycline at 10 ug/mL was added to medium for reactions using either of the single plasmid recombinants; 10 ug/mL tetracycline and 25 ug/mL chloramphenicol for reactions using either of the double plasmid recombinants. The medium was thoroughly sparged with nitrogen prior to inoculation with 2 mL of the subculture. IPTG (I) at final concentration of 0.5 mM was added to some flasks. The flasks were capped, then incubated at 37° C., 100 rpm in a New Brunswick Series 25 incubator/shaker. Reactions were run for at least 24 hours or until most of the carbon substrate was converted into products. Samples were analyzed by HPLC. Table 5 describes the yields of 1,3-propanediol (3G) produced from fructose by the various Klebsiella recombinants.

TABLE 5

Production of 1,3-propanediol from D-fructose using recombinant Klebsiella

| Klebsiella Strain | Medium | Conversion | [3G] (g/L) | Yield Carbon (%) |
|---|---|---|---|---|
| 2106 pBR329 | LLMM/F | 100 | 0 | 0 |
| 2106 pJSP1A | LLMM/F | 50 | 0.66 | 15.5 |
| 2106 pJSP1A | LLMM/F + I | 100 | 0.11 | 1.4 |
| 2106 pJSP1A/pJSP2 | LLMM/F | 58 | 0.26 | 5 |
| 25955 pBR329 | LLMM/F | 100 | 0 | 0 |
| 25955 pJSP1A | LLMM/F | 100 | 0.3 | 4 |
| 25955 pJSP1A | LLMM/F + I | 100 | 0.15 | 2 |
| 25955 pJSP1A/pJSP2 | LLMM/F | 100 | 0.9 | 11 |
| 25955 pJSP1A/pJSP2 | LLMM/F + I | 62 | 1.0 | 20 |

B. Conversion of various carbon substrates to 1,3-propanediol by *K. pneumoniae* (ATCC 25955 pJSP1A/pJSP2):

An aliquot (0.1 mL) of frozen stock cultures of *K. pneumoniae* (ATCC 25955 pJSP1A/pJSP2) was transferred to 50 mL Seed medium in a 250 mL baffled flask. The Seed medium contained per liter: 0.1 molar NaK/PO$_4$ buffer, pH 7.0; 3 g (NH$_4$)$_2$SO$_4$; 5 g glucose, is 0.15 g MgSO$_4$.7H$_2$O, 10 mL 100× Trace Element solution, 25 mg chloramphenicol, 10 mg tetracycline, and 1 g yeast extract. The 100× Trace Element contained per liter: 10 g citric acid, 1.5 g CaCl$_2$.2H$_2$O, 2.8 g FeSO$_4$.7H$_2$O, 0.39 g ZnSO$_4$.7H$_2$O, 0.38 g CuSO$_4$.5H$_2$O, 0.2 g CoCl$_2$.6H$_2$O, and 0.3 g MnCl$_2$.4H$_2$O. The resulting solution was titrated to pH 7.0 with either KOH or H$_2$SO$_4$. The glucose, trace elements, antibiotics and yeast extracts were sterilized separately. The seed inoculum was grown overnight at 35° C. and 250 rpm.

The reaction design was semi-aerobic. The system consisted of 130 mL Reaction medium in 125 mL sealed flasks that were left partially open with aluminum foil strip. The Reaction Medium contained per liter: 3 g (NH$_4$)$_2$SO$_4$; g carbon substrate; 0.15 molar NaK/PO$_4$ buffer, pH 7.5; 1 g yeast extract; 0.15 g MgSO$_4$.7H$_2$O; 0.5 mmoles IPTG; 10 mL 100× Trace Element solution; 25 mg chloramphenicol; and 10 mg tetracycline. The resulting solution was titrated to pH 7.5 with KOH or H$_2$SO$_4$. The carbon sources were: D-glucose (Glc); D-fructose (Frc); D-lactose (Lac); D-sucrose (Suc); D-maltose (Mal); and D-mannitol (Man). A few glass beads were included in the medium to improve mixing. The reactions were initiated by addition of seed inoculum so that the optical density of the cell suspension started at 0.1 AU as measured at 1600 nm. The flasks were incubated at 35 OC: 250 rpm. 3G production was measured by HPLC after 24 hr. Table 6 describes the yields of 1,3-propanediol produced from the various carbon substrates.

TABLE 6

Production of 1,3-propanediol from various carbon substrates using recombinant Klebsiella 25955 pJSP1A/pJSP2

| Carbon Substrate | 1,3-Propanediol (g/L) | | |
|---|---|---|---|
| | Expt. 1 | Expt. 2 | Expt 3 |
| Glc | 0.89 | 1 | 1.6 |
| Frc | 0.19 | 0.23 | 0.24 |
| Lac | 0.15 | 0.58 | 0.56 |
| Suc | 0.88 | 0.62 | |
| Mal | 0.05 | 0.03 | 0.02 |
| Man | 0.03 | 0.05 | 0.04 |

Example 9

Improvement of 1,3-Propanediol Production Using dhaBX Gene

Example 9 demonstrates the improved production of 1,3-propanediol in *E. coli* when a gene encoding a protein X is introduced.

Construction of expression vector pTacIQ

The *E. coli* expression vector, pTacIQ containing the lacIq gene (Farabaugh, P. J. 1978, Nature 274 (5673) 765–769) and tac promoter (Amann et al, 1983, Gene 25, 167–178) was inserted into the restriction endonuclease site EcoRI of pBR322 (Sutcliffe, 1979, Cold Spring Harb. Symp. Quant. Biol. 43, 77–90). A multiple cloning site and terminator sequence (SEQ ID NO:50) replaces the pBR322 sequence from EcoRI to SphI.

Subcloning the glycerol dehydratase genes (dhaB1, 2, 3, X)

The region containing the entire coding region for Klebsiella dhaB1, dhaB2, dhaB3 and dhaBX of the dhaB operon from pHK28-26 was cloning into pBluescriptIIKS+ (Stratagene) using the restriction enzymes KpnI and EcoRI to create the plasmid pM7.

The open reading frame for dhaB3 gene was amplified from pHK 28-26 by PCR using primers (SEQ ID NO:51 and SEQ ID NO:52) incorporating an EcoRI site at the 5' end and a XbaI site at the 3' end. The product was subcloned into pLitmus29(NEB) to generate the plasmid pDHAB3 containing dhaB3.

The dhaBXgene was removed by digesting plasmid pM7 with ApaI and XbaI, purifying the 5.9 kb fragment and ligating it with the 325-bp ApaI-XbaI fragment from plasmid pDHAB3 to create pM11 containing dhaB1, dhaB2 and dhaB3.

The open reading frame for the dhaB1 gene was amplified from pHK28-26 by PCR using primers (SEQ ID NO:53 and SEQ ID NO:54) incorporating HindIII site and a consensus ribosome binding site at the 5' end and a XbaI site at the 3' end. The product was subcloned into pLitmus28(NEB) to generate the plasmids pDT1 containing dhaB1.

A NotI-XbaI fragment from pM11 containing part of the dhaB1 gene, the dhaB2 gene and the dhaB3 gene with inserted into pDT1 to create the dhaB expression plasmid, pDT2. The HinDIII-XbaI fragment containing the dhaB(1,2,3) genes from pDT2 was inserted into pTacIQ to create pDT3.

Subcloning the TMG dehydrogenase gene (dhaT)

The KpnI-SacI fragment of pHK28-26, containing the TMG dehydrogenase (dhaT) gene, was subcloned into pBluescriptII KS+ creating plasmid pAH1. The dhaT gene was cloned by PCR from pAH1 as template DNA and synthetic primers (SEQ ID NO:55 with SEQ ID NO:56) incorporating an XbaI site at the 5' end and a BamHI site at the 3' end. The product was subcloned into pCR-Script (Stratagene) at the SrfI site to generate the plasmids pAH4 and pAH5 containing dhaT. The pAH4 contains the dhaT gene in the right orientation for expression from the lac promoter in pCR-Script and pAH5 contains dhaT gene in the opposite orientation. The XbaI-BamHI fragment from pHA4 containing the dhaT gene was inserted into pTacIQ to generate plasmid, pAH8. The HindII-BamHI fragment from pAH8 containing the RBS and dhaT gene was inserted into pBluescriptII KS+to create pAHII.

Construction of an expression cassette for dhaT and dhaB (1,2,3)

An expression cassette for dhaT and dhaB(1,2,3) was assembled from the individual dhaB(1,2,3) and dhaT subclones described previously using standard molecular biology methods. A SpeI-SacI fragment containing the dhaB(1, Z3) genes from pDT3 was inserted into pAH 11 at the SpeI-SacI sites to create pAH24. A SalI-XbaI linker (SEQ ID NO 57and SEQ ID NO 58) was inserted into pAH5 which was digested with the restriction enzymes SalI-XbaI to create pDT16. The linker destroys the XbaI site. The 1 kb SalI-MluI fragment from pDT16 was then inserted into pAH24 replacing the existing SalI-MluI fragment to create pDT18.

Plasmid for the over-expression of dhaT and dhaB(1, 2, 3, X) in *E. coli*

The 4.4 kb NotI-XbaI fragment containing part of the dhaB1 gene, dhaB2, dhaB3 and dhaBX from plasmid pM7 was purified and ligated with the 4.1 Kb NotI-XbaI fragment from plasmid pDT18 (restoring dhaB1) to create pM33 containing the dhaB1, dhaB2, dhaB3 and dhaBX.

*E. coli* strain

*E. coli* DH5a was obtained from BRL (Difco). This strain was transformed with the plasmids pM7, pM11, pM33 or pDT18 and selected on LA plates containing 100 ug/ml carbenicillin.

Production of 1,3-propanediol

*E. coli* DH5a, containing plasmid pM7, pM11, pM33 or pDT18 was grown on LA plates plus 100 ug/ml carbenicillin overnight at 37° C. One colony from each was used to inoculate 25 ml of media (0.2 M $KH_2PO_4$, citric acid 2.0 g/L, MgSO4*7H2O 2.0 g/L, H2SO4 (98%) 1.2 ml/L, Ferric ammonium citrate 0.3 g/L, CaCl2*2H2O 0.2 gram, yeast extract 5 g/L, glucose 10 g/L, glycerol 30 g/L,) plus Vitamine B12 0.005 g/L, 0.2 mM IPTG, 200 ug/ml carbenicillin and 5 ml modified Balch's trace-element solution (the composition of which can be found in Methods for General and Molecular Bacteriology (P. Gerhardt el el., eds, p 158, American Society for Microbiology, Washington, DC 1994), final pH 6.8 (NH4OH), then filter-sterilized in 250 ml erlenmeyers flasks. The shake flasks were incubated at 37° C. with shaking (300 rpm) for several days, during which they were sampled for HPLC analysis by standard procedures. Final yields are shown in Table 4.

Overall, as shown in Table 7, the results indicate that the expression of dhaBX in plasmids expressing dhaB(1,2,3) or dhaT-dhaB(1,2,3) greatly enhances the production of 1,3-propanediol.

TABLE 7

Effect of dhaBX expression on the production of 1,3-propanediol by *E. coli*

| Strain | Time (days) | 1,3-propanediol (mg/L)* |
|---|---|---|
| DH5a/pM7 (dhaB1,2,3,X) | 1 | 1500 |
|  | 2 | 2700 |
| DH5a/pM11 (dhaB1,2,3) | 1 | <200 μg |
|  | 2 | <200 μg |
| DH5a/pM33 (dhaT-dhaB1,2,3,X) | 2 | 1200 |
| DH5a/pDT18 (dhaT-dhaB1,2,3) | 2 | 88 |

*Expressed as an average from several experiments.

Primers:
SEQ ID NO:50—MCS—TERMINATOR:
5 AGCTTAGGAGTCTAGAATATTGAGCTC-GAATTCCCGGGGCATGCGGTACCGGATC-CAGAAA AAGCCCGCACCTGACAG-GCGGGCTTTTTTTTT3'
SEQ ID NO:51—dhaB3-5' end. EcoRI
GGAATTCAGATCTCAGCAATGAGCGAG-MAACCATGC
SEQ ID NO 52: dhaB3-3' end XbaI
GCTCTAGATTAGCTTCCTTTACGCAGC
SEQ ID NO 53: dhaB1 5' end-HindII-SD
5' GGCCAAGCTTMGGAGGTTATTAAATGAAAAG 3'
SEQ ID NO 54: dhaB1 3'end-XbaI
5' GCTCTAGATTATTCAATGGTGTCGGG 3'
SEQ ID NO 55: dhaT5' end-XbaI
5' GCGCCGTCTAGAATTATGAGCTATCG-TATGTTTGATTATCTG 3'
SEQ ID NO 56: dhaT3' end-BamHI
5'TCTGATACGGGATCCTCAGAATGCCTG-GCGGAAAAT 3'
SEQ ID NO 57: pUSH Linker1:
5' TCGACGAATTCAGGAGGA 3'
SEQ ID NO 58: pUSH Linker2:
5' TAGTCCTCCTGMTTCG 3'

Example 10

Reactivation of the Glycerol Dehydratase Activity

Example 10 demonstrates the in vivo reactivation of the glycerol dehydratase activity in microorganisms containing at least one gene encoding protein X.

Plasmids pM7 and pM11 were constructed as described in Example 9 and transformed into *E. coli* DH5α cells. The transformed cells were cultured and assayed for the production of 1,3-propanediol according to the method of Honda et al. (1980, In Situ Reactivation of Glycerol-Inactivated Coenzyme $B_{12}$-Dependent Enzymes, Glycerol Dehydratase and Diol Dehydratase. Journal of Bacteriology 143:1458–1465).

Materials and methods

Toluenization of Cells

The cells were grown to mid-log phase and were harvested by centrifugation at room temperature early in growth, i.e. 0.2>OD600<0.8. The harvested cells were washed 2× in 50 mM $KPO_4$ pH8.0 at room temperature. The cells were resuspended to $OD_{600}$ 20–30 in 50 mM $KPO_4$ pH8.0. The absolute OD is not critical. A lower cell mass is resuspend in less volume. If coenzyme B12 is added at this point, the remainder of the steps are performed in the dark. Toluene is added to 1% final volume of cell suspension and the suspension is shaked vigorously for 5 minutes at room temperature. The suspension is centrifuged to pellet the cells. The cells are washed 2× in 50 mM $KPO_4$ pH8.0 at room temperature (25 mls each). The cell pellet is resuspended in the same volume as was used prior to toluene addition and transfer to fresh tubes. The $OD_{600}$ for the toluenized cells was measured and recorded and stored at 4 degrees C.

Whole Cell Glycerol Dehydratase Assay The toluene treated cells were assayed at 37 degrees C for the presence of dehydratase activity. Three sets of reactions were carried out as shown below: no ATP, ATP added at 0 time, and ATP added at 10 minutes.

| | | |
|---|---|---|
| No ATP: | 100 ul | 2M Glycerol |
| | 100 ul | 150 uM $CoB_{12}$ |
| | 700 ul | Buffer (0.03M $KPO_4$/0.5M KCl, pH 8.0) |
| T = 0 minute ATP | 100 ul | 2M Glycerol |
| | 100 ul | 150 uM $CoB_{12}$ |
| | 600 ul | Buffer (0.03M $KPO_4$/0.5M KCl, pH 8.0) |
| | 100 ul | 30 mM ATP/30 mM $MnCl_2$ |
| T = 10 minute ATP | 100 ul | 2M Glycerol |
| | 100 ul | 150 uM $CoB_{12}$ |
| | 700 ul | Buffer (0.03M $KPO_4$/0.5M KCl, pH 8.0) |

Controls were prepared for each of the above conditions by adding 100uls buffer instead of $CoB_{12}$. The tubes were mixed. 50 uls MBTH (3-Methyl-2-Benzo-Thiazolinone Hydrazone) (6 mg/ml in 375mM Glycine /HCl pH2.7) was added to each of these tubes and continue incubation in ice water. The reaction tubes were placed in a 37 degree C water bath for a few minutes to equilibrate to 37 degree C. A tube containing enough toluenized cells for all assay tubes was placed into the 37 degree C water bath for a few minutes to equilibrate to 37 degree C. A tube containing 2.5 fold diluted (in assay buffer) 30 mM ATP/30 mM $MnCl_2$(12mM each) was placed into the 37 degree C water bath for a few minutes to equilibrate to 37 degree C. A 100ul cell suspension was added to all tubes and samples were taken at 0,1,2,3,4,5,10, 15,20 and 30 minutes. At every timepoint, 100 uls of reaction was withdrawn and immediately added to 50 uls ice cold MBTH, vortexed, and placed in an ice water bath. At T=10 minutes, a sample was withdrawn and added to MBTH, then 100uls of the 2.5 fold diluted ATP/Mn was added as fast as is possible. When all samples were collected, the sample tube rack was added to a boiling water bath and boiled for three minutes. The tubes were chilled in an ice water bath for 30 seconds. 500 uls of freshly prepared 3.3 mg/ml FeCl3.6H2O, was added to the tubes and the tubes vortexed. The tubes were incubated at room temperature for 30 minutes, diluted 10× in H2O, and then centrifuged to collect the cells and particulates. The absorbance was measured at 670nM and the cells were diluted to keep OD under 1.0.

Example of Calculation of Activity

The observed OD670 was multiplied by the dilution factor to determine absorbance. The blank absorbance was substracted for that reaction series and the T0 A67OnM was substracted. The absolute A670 nM was divided by 53.4 (mM extinction coefficient for 3OH-propioaldehyde) and the mM concentration was multiplied by any dilution of reaction during timecourse. Because 1 ml reaction was used, the concentration (umoles/ml) of 3OH-propionaldehyde was divided by the mgs dry weight used in the assay (calculated via OD600 and 1OD 600=0.436 mgs dry weight) to get umoles aldehyde per mg dry weight cells.

Results

As shown in FIG. 6, whole E. coli cells were assayed for reactivation of glycerol dehydratase in the absence and presence of added ATP and Mn++. The results indicate that cells containing a plasmid carrying dhaB 1, 2 and 3 as well as protein X have the ability to reactivate catalytically inactivated glycerol dehydrogenase. Cells containing protein 1, protein 2 and protein 3 have increased ability to reactivate the catalytically inactivated glycerol dehydratase.

As shown in FIG. 7, whole E. coli cells were assayed for reactivation of glycerol-inactivated glycerol dehydratase in the absence and in the presence of added ATP and Mn++. The results show that cells containing dhaB subunits 1, 2 and 3 and X have the ability to reactivate catalytically inactivated glycerol dehydratase. Cell lacking the protein X gene do not have the ability to reactivate the catalytically inactivated glycerol dehydratase.

FIGS. 9 and 10 illustrate that host cells containing plasmid pHK 28-26 (FIG. 1), when cultured under conditions suitable for the production of 1,3-propanediol, produced more 1,3-propanediol than host cells transformed with pDT24 and cultured under conditions suitable for the production of 1,3-propanediol. Plasmid pDT24 is a derivative of pDT18 (described in Example 9) and contains dhaT, dhaB 1, 2, 3 and protein X, but lacks proteins 1, 2 and 3.

What is claimed is:

1. A method for the production of 1,3-propanediol from a recombinant microorganism comprising the step of culturing a recombinant microorganism capable of producing 1,3 propanediol and comprising at least nucleic acid encoding a dehydratase activity and a nucleic acid encoding protein X in the presence of at least one carbon source capable of being converted to 1,3 propanediol in said recombinant microorganism and under conditions suitable for the production of 1,3 propanediol, wherein the gene encoding protein X is isolated from a glycerol dehydratase gene cluster from an organism selected from the group of genera consisting of Klebsiella and Citrobacter or wherein the gene encoding protein X is isolated from a diol dehydratase gene cluster from an organism selected from the group of genera consisting of Klebsiella Clostridium and Salmonella, wherein production of 1,3-propanediol is greater in the microorganism than in the absence of said nucleic acid encoding protein X and wherein-protein X has no enzymatic activity, and wherein the carbon source is selected from the group consisting of monosaccharides, oligosaccharides, polysaccharides, and a one carbon substrate.

2. The method of claim 1 further comprising the step of introducing at least one gene encoding a protein selected from the group consisting of protein 1, protein 2 and protein 3 into the microorganism, wherein said protein 1 has an amino acid sequence corresponding to SEQ ID NO:60 or SEQ ID NO:61, wherein protein 2 has an amino acid sequence corresponding to SEQ ID NO:62 or SEQ ID NO:63, and wherein protein 3 has an amino acid sequence corresponding to SEQ ID NO:64 or SEQ ID NO:65 and, wherein the production of 1,3-propanediol is higher in the microorganism than in the absence of said gene.

3. The method of claim 1 further comprising the step of recovering the 1,3 propanediol.

4. The method of claim 1 wherein the gene encoding a dehydratase activity is heterologous to the microorganism.

5. The method of claim 1 wherein the gene encoding a dehydratase activity is homologous to the microorganism.

6. The method of claim 1 wherein the microorganism is selected from the group of genera consisting of Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas.

7. The method of claim 6 wherein the microorganism is selected from the group consisting of *E. coli* and Klebsiella ssp.

8. The method of claim 1 wherein the gene encoding protein X is integrated into the chromosomal DNA of the host genome.

9. The method of claim 2 wherein at least one gene encoding a protein selected from protein 1, protein 2 and protein 3 is integrated into the chromosomal DNA of the host genome.

10. The method of claim 1 wherein the carbon source is glucose.

11. The method of claim 1 wherein the gene encoding protein X has the sequence as shown in SEQ ID NO:59.

12. The method of claim 2 wherein protein 1 has the sequence as shown in SEQ ID NO: 60 or SEQ ID NO: 61.

13. The method of claim 2 wherein protein 2 has the sequence as shown in SEQ ID NO: 62 or SEQ ID NO: 63.

14. The method of claim 2 wherein protein 3 has the sequence as shown in SEQ ID NO: 64 or SEQ ID NO: 65.

15. The method of claim 1, wherein said protein X of *K. pneumoniae* glycerol dehydratase is encoded by the nucleic acid sequence of residues 9749–11572 of SEQ ID NO: 19.

16. The method of claim 1, wherein said protein X is from *C. freundii*.

17. The method of claim 1, wherein said protein X is encoded by the ORF Z of the dha regulon of the genus Citrobacter.

* * * * *